US008771698B2

(12) United States Patent
Pearson et al.

(10) Patent No.: US 8,771,698 B2
(45) Date of Patent: Jul. 8, 2014

(54) MODULATION OF UL24 INTERACTIONS WITH PROTEIN TARGETS AND USES THEREOF FOR INHIBITION OF HERPESVIRUS INFECTION

(71) Applicant: Institut National de la Recherche Scientifique, Quebec (CA)

(72) Inventors: Angela Pearson, Mont-Royal (CA); Luc Bertrand, Laval (CA)

(73) Assignee: Institut National de la Recherche Scientifique, Quebec (CA)

( * ) Notice: Subject to any disclaimer, the term of this patent is extended or adjusted under 35 U.S.C. 154(b) by 0 days.

(21) Appl. No.: 13/661,212

(22) Filed: Oct. 26, 2012

(65) Prior Publication Data

US 2013/0108649 A1    May 2, 2013

Related U.S. Application Data

(60) Provisional application No. 61/552,110, filed on Oct. 27, 2011.

(51) Int. Cl.
| | | |
|---|---|---|
| *C12Q 1/70* | (2006.01) |
| *A61K 39/00* | (2006.01) |
| *A61K 39/395* | (2006.01) |
| *G01N 33/569* | (2006.01) |
| *A61K 38/17* | (2006.01) |
| *A61P 31/22* | (2006.01) |
| *A61K 38/16* | (2006.01) |
| *C07K 16/08* | (2006.01) |

(52) U.S. Cl.
CPC ........... *A61K 38/162* (2013.01); *A61K 38/1709* (2013.01); *C07K 16/087* (2013.01); *G01N 33/569* (2013.01); *A61K 2039/505* (2013.01)
USPC ...... 424/159.1; 435/5; 424/130.1; 424/184.1; 424/94.1; 424/172.1; 436/501; 514/4.2

(58) Field of Classification Search
CPC ............ A61K 38/162; A61K 38/1709; A61K 2039/505; A61K 35/763; A61K 39/245; C07K 16/087; C07K 14/005; C07K 14/035; C07K 16/085; C07K 16/088; G01N 33/569; C12N 7/00; C12N 2710/16161; C12N 2710/16611; C12Q 1/705; C12Q 1/18
USPC ................. 424/159.1, 130.1, 172.1; 436/501; 514/4.2

See application file for complete search history.

(56) References Cited

U.S. PATENT DOCUMENTS

| | | | | |
|---|---|---|---|---|
| 6,054,265 | A * | 4/2000 | Barney et al. ...................... 435/5 |
| 2004/0228876 | A1 * | 11/2004 | Nishiyama .................. 424/199.1 |
| 2008/0069837 | A1 * | 3/2008 | Nishiyama .................. 424/199.1 |
| 2010/0272706 | A1 * | 10/2010 | Mercer et al. .............. 424/130.1 |
| 2013/0115589 | A1 * | 5/2013 | Kawaguchi et al. ................ 435/5 |

OTHER PUBLICATIONS

Ben Abdeljelil N, Rochette PA, Pearson A. The UL24 protein of herpes simplex virus 1 affects the sub-cellular distribution of viral glycoproteins involved in fusion. Virology. Sep. 2013;444(1-2):263-73.*
Arii J, Goto H, Suenaga T, Oyama M, Kozuka-Hata H, Imai T, Minowa A, Akashi H, Arase H, Kawaoka Y, Kawaguchi Y. Non-muscle myosin IIA is a functional entry receptor for herpes simplex virus-1. Nature. Oct. 14, 2010;467(7317):859-62.*
Heldwein EE, Krummenacher C. Entry of herpesviruses into mammalian cells. Cell Mol Life Sci. Jun. 2008;65(11):1653-68.*
Bertrand L, Leiva-Torres GA, Hyjazie H, Pearson A. Conserved residues in the UL24 protein of herpes simplex virus 1 are important for dispersal of the nucleolar protein nucleolin. J Virol. Jan. 2010;84(1):109-18. Epub . Erratum in: J Virol. Oct. 2010;84(19):10436.*
Lymberopoulos MH, Bourget A, Ben Abdeljelil N, Pearson A. Involvement of the UL24 protein in herpes simplex virus 1-induced dispersal of B23 and in nuclear egress. Virology. Apr. 10, 2011;412(2):341-8. Epub Feb. 12, 2011.*
Grinham,J.A., Collins,J.E., Matthews,N., Wright,C.L., Taylor,C., Beare,D.M. and Dunham,I. NCBI Direct Submission. Myosin-9. Submitted (Jun. 21, 2006) Sanger Institute, Hinxton, Cambridgeshire.*
McGeoch,D.J.. NCBI Direct Submission. HSV UL24. Submitted (Jan. 17, 1989) McGeoch D.J., MRC Virology Institute,Institute of Virology, Church Street, Glasgow GII 5JR, GB.*
Coleman JL, Shukla D. Recent advances in vaccine development for herpes simplex virus types I and II. Hum Vaccin Immunother. Feb. 26, 2013;9(4).).*
De Clercq E. Antivirals: past, present and future. Biochem Pharmacol. Mar. 15, 2013;85(6):727-44. doi: 10.1016/j.bcp.2012.12.011. Epub Dec. 24, 2012.*
van Leeuwen H, Elliott G, O'Hare P. Evidence of a role for nonmuscle myosin II in herpes simplex virus type 1 egress. J Virol. Apr. 2002;76(7):3471-81.*
Arii et al. "Non-muscle myosin IIA is a functional entry receptor for herpes simplex virus-1" Nature vol. 467:859-62, Oct. 14, 2010.
Bertrand et al. "Conserved residues in the UL24 protein of herpes simplex virus 1 are important for dispersal of the nucleolar protein nucleolin", Journal of Virology, vol. 84, No. 1, Jan. 2010, p. 109-18.
Bertrand et al. "The conserved N-terminal domain of herpes simplex virus 1 UL24 protein is sufficient to induce the spatial redistribution of nucleolin", Journal of General Virology (2008) 89, 1142-51.
Blakeney et al. "Herpes simplex virus type 2 UL24 gene is a virulence determinant in murine and guinea pig disease models", Journal of Virology, vol. 79, No. 16, Aug. 2005, p. 10498-10506.
Diefenbach et al. "Herpes simplex virus tegument protein US11 interacts with conventional kinesin heavy chain", Journal of Virology, vol. 76, No. 7, Apr. 2002, p. 3282-9291.
Ikonen et al. "Myosin II is associated with Golgi membranes: identification of p200 as nonmuscle myosin II on Golgi-derived vesicles" Journal of Cell Science, 110, p. 2155-64, 1997.

(Continued)

*Primary Examiner* — Benjamin P Blumel
*Assistant Examiner* — Rachel Gill
(74) *Attorney, Agent, or Firm* — Goudreau Gage Dubuc; Alain Dumont

(57) ABSTRACT

Methods and uses for the treatment of herpesvirus infection based on the inhibition of the interaction between herpesvirus UL24 and non-muscle myosin type IIa (NM2a) are described.

3 Claims, 23 Drawing Sheets

(56) References Cited

OTHER PUBLICATIONS

Jacobson et al. "Importance of the herpes simplex virus UL24 gene for productive ganglionic infection in mice", Virology, 242, p. 161-169, 1998.

Jacobson et al. "A conserved open reading frame that overlaps the herpes simplex virus thymidine kinase gene is important for viral growth in cell culture" Journal of Virology, vol. 63, No. 4, p. 1839-1843, 1989.

Johnson et al. "Herpesviruses remodel host membranes for virus egress", Nature, vol. 9, p. 382-394, May 2011.

Knizewski et al. "Human herpesvirus 1 UL24 gene encodes a potential PD-(D/E)XK endonuclease", Journal of Virology, vol. 80, No. 5, p. 2575-2577, Mar. 2006.

Leiva-Torres et al. "Differential importance of highly conserved residues in UL24 for herpes simplex virus 1 replication in vivo and reactivation", Journal of General Virology (2010), 91, p. 1109-1116.

Lymberopoulos et al. "Involvement of UL24 in herpes-simplex-virus-1-induced dispersal of nucleolin", Virology 363 (2007) p. 397-409.

\* cited by examiner

| Protein | MS Score | Peptides identified |
|---|---|---|
| Non-muscle myosin type IIA | 1652 | EQADFAIEALAK (SEQ ID NO:5)<br>LRLEVNLQAMK (SEQ ID NO:6)<br>LDPHLVLDQLR (SEQ ID NO:7)<br>VIQYLAYVASSHK (SEQ ID NO:8)<br>VISGVLQLGNIVFK (SEQ ID NO:9)<br>VISGVLQLGNIVFKK (SEQ ID NO:10)<br>IMGIPEEEQMGLLR (SEQ ID NO:11)<br>IAEFTTNLTEEEEK (SEQ ID NO:12)<br>NFINNPLAQADWAAK (SEQ ID NO:13)<br>QLLQANPILEAFGNAK (SEQ ID NO:14)<br>LTEMETLQSQLMAEK (SEQ ID NO:15)<br>IAEFTTNLTEEEEKSK (SEQ ID NO:16)<br>ANLQIDQINTDLNLER (SEQ ID NO:17)<br>(SEQ ID NO:18) LQVELDNVTGLLSQSDSK<br>(SEQ ID NO:19) LQQELDDLLVDLDHQR<br>(SEQ ID NO:20) TQLEELEDELLQATEDAK<br>(SEQ ID NO:21) KANLQIDQINTDLNLER<br>(SEQ ID NO:22) IIGLDQVAGMSETALPGAFK<br>(SEQ ID NO:23) TLEEEAKTHEAQIQEMR<br>(SEQ ID NO:24) SMEAEMIQLQEELAAAER<br>(SEQ ID NO:25) IRELESQISELQEDLESER<br>(SEQ ID NO:26) MQQNIQELEEQLEEEESAR<br>(SEQ ID NO:27) INFDVNGYIVGANIETYLLEK<br>(SEQ ID NO:28) LQQLFNHTMFILEQEEYQR<br>(SEQ ID NO:29) DFSALESQLQDTQELLQEENR<br>(SEQ ID NO:30) ALEQQVEEMKTQLEELEDELQATEDAK |

FIG. 2B

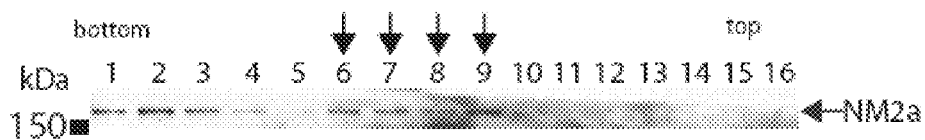

FIG. 2C

```
  1 MAARTRSLVE RRRVLMAGVR SHTRFYKALA EEVREFHATK ICGTLLTLLS GSLQGRSVFE
 61 ATRVTLICEV DLGPRRPDCI CVFEFANDKT LGGVCVIIEL KTCKYISSGD TASKREQRAT
121 GMKQLRHSLK LLQSLAPPGD KIVYLCPVLV FVAQRTLRVS RVTRLVPQKV SGNITAVVRM
181 LQSLSTYTVP IEPRTQRARR RRGGAARGSA SRPKRSHSGA RDPPESAARQ LPPADQTPTS
241 TEGGGVLKRI AALFCVPVAT KTKPRAASE  269
```

FIG. 6A

```
   atgg ccgcgagaac gcgcagcctg gtcgaacgca gacgcgtgtt gatggcaggg
gtacgaagcc atacgcgctt ctacaaggcg ctggccgaag aggtgcggga gtttcacgcc accaagatct
gcggcacgct gttgacgctg ttaagcgggt cgctgcaggg tcgctcggta ttcgaggcca cacgcgtcac
cttaatatgc gaagtggacc tgggaccgcg ccgccccgac tgcatctgcg tgttcgaatt cgccaatgac
aagacgctgg cggggtttg tgtcatcata gaactaaaga catgcaaata tatttcttcc ggggacaccg
ccagcaaacg cgagcaacgg gccacgggga tgaagcagct cgccactcc ctgaagctcc tgcagtccct
cgcgcctccg ggtgacaaga tagtgtacct gtgccccgtc ctggtgtttg tcgccaacg gacgctccgc
gtcagccgcg tgaccggct cgtcccgcag aaggtctccg gtaatatcac cgcagtcgtg cggatgctcc
agagcctgtc cacgtatacg gtccccattg agcctaggac ccagcgagcc cgtcgccgc gcggcggcgc
cgcccggggg tctgcgagca gaccgaaaag gtcacactct ggggcgcgcg accgcccga gtcagcggcc
cgccagttac cacccgccga ccaaacccc acctccacgg aggggcgggg ggtgcttaag aggatcgcgg
cgctcttctg cgtgcccgtg ccaccaaga ccaaacccg agccgcctcc gaatga
```

FIG. 6B

```
   1 MAQQAADKYL YVDKNFINNP LAQADWAAKK LVWVPSDKSG FEPASLKEEV GEEAIVELVE
  61 NGKKVKVNKD DIQKMNPPKF SKVEDMAELT CLNEASVLHN LKERYYSGLI YTYSGLFCVV
 121 INPYKNLPIY SEEIVEMYKG KKRHEMPPHI YAITDTAYRS MMQDREDQSI LCTGESGAGK
 181 TENTKKVIQY LAYVASSHKS KKDQGELERQ LLQANPILEA FGNAKTVKND NSSRFGKFIR
 241 INFDVNGYIV GANIETYLLE KSRAIRQAKE ERTFHIFYYL LSGAGEHLKT DLLLEPYNKY
 301 RFLSNGHVTI PGQQDKDMFQ ETMEAMRIMC IPEEEQMGLL RVISGVLQLG NIVFKKERNT
 361 DQASMPDNTA AQKVSHLLGI NVTDFTRGIL TPRIKVGRDY VQKAQTKEQA DFAIEALAKA
 421 TYERMFRWLV LRINKALDKT KRQGASFIGI LDIAGFEIFD LNSFEQLCIN YTNEKLQQLF
 481 NHTMFILEQE EYQREGIEWN FIDFGLDLQP CIDLIEKPAG PPGILALLDE ECWFPKATDK
 541 SFVEKVMQEQ GTHPKFQKPK QLKDKADFCI IHYAGKVDYK ADEWLMKNMD PLNDNIATLL
 601 HQSSDKFVSE LWKDVDRIIG LDQVAGMSET ALPGAFKTRK GMFRTVGQLY KEQLAKLMAT
 661 LRNTNPNFVR CIIPNHEKKA GKLDPHLVLD QLRCNGVLEG IRICRQGFPN RVVFQEFRQR
 721 YEILTPNSIP KGFMDGKQAC VLMIKALELD SNLYRIGQSK VFFRAGVLAH LEEERDLKIT
 781 DVIIGFQACC RGYLARKAFA KRQQQLTAMK VLQRNCAAYL KLRNWQWWRL FTKVKPLLQV
 841 SRQEEEMMAK EEELVKVREK QLAAENRLTE METLQSQLMA EKLQLQEQLQ AETELCAEAE
 901 ELRARLTAKK QELEEICHDL EARVEEEEER CQHLQAEKKK MQQNIQELEE QLEEEESARQ
 961 KLQLEKVTTE AKLKKLEEEQ IILEDQNCKL AKEKKLLEDR IAEFTTNLTE EEEKSKSLAK
1021 LKNKHEAMIT DLEERLRREE KQRQELEKTR RKLEGDSTDL SDQIAELQAQ IAELKMQLAK
1081 KEEELQAALA RVEEEAAQKN MALKKIRELE SQISELQEDL ESERASRNKA EKQKRDLGEE
1141 LEALKTELED TLDSTAAQQE LRSKREQEVN ILKKTLEEEA KTHEAQIQEM RQKHSQAVEE
1201 LAEQLEQTKR VKANLEKAKQ TLENERGELA NEVKVLLQGK GDSEHKRKKV EAQLQELQVK
1261 FNEGERVRTE LADKVTKLQV ELDNVTGLLS QSDSKSSKLT KDFSALESQL QDTQELLQEE
1321 NRQKLSLSTK LKQVEDEKNS FREQLEEEEE AKHNLEKQIA TLHAQVADMK KKMEDSVGCL
1381 ETAEEVKRKL QKDLEGLSQR HEEKVAAYDK LEKTKTRLQQ ELDDLLVDLD HQRQSACNLE
1441 KKQKKFDQLL AEEKTISAKY AEERDRAEAE AREKETKALS LARALEEAME QKAELERLNK
1501 QFRTEMEDLM SSKDDVGKSV HELEKSKRAL EQQVEEMKTQ LEELEDELQA TEDAKLRLEV
1561 NLQAMKAQFE RDLQGRDEQS EEKKKQLVRQ VREMEAELED ERKQRSMAVA ARKKLEMDLK
1621 DLEAHIDSAN KNRDEAIKQL RKLQAQMKDC MRELDDTRAS REEILAQAKE NEKKLKSMEA
1681 EMIQLQEELA AAERAKRQAQ QERDELADEI ANSSGKGALA LEEKRRLEAR IAQLEEELEE
1741 EQGNTELIND RLKKANLQID QINTDLNLER SHAQKNENAR QQLERQNKEL KVKLQEMEGT
1801 VKSKYKASIT ALEAKIAQLE EQLDNETKER QAACKQVRRT EKKLKDVLLQ VDDERRNAEQ
1861 YKDQADKAST RLKQLKRQLE EAEEEAQRAN ASRRKLQREL EDATETADAM NREVSSLKNK
1921 LRRGDLPFVV PRRMARKGAG DGSDEEVDGK ADGAEAKPAE
```

FIG. 7A

```
   1 gagggcgggg cgggaaggcg gcgaggagcc gagctgggtg cggtgaggcg cgcagatcac
  61 cgcggttcct gggcagggca cggaaggcta agcaaggctg acctgctgca gctcccgcct
 121 cgtgcgctcg ccccacccgg ccgccgcccg agcgctcgag aaagtcctct cgggagaagc
 181 agcgcctgtt cccggggcag atccaggttc aggtcctggc tataagtcac catggcacag
 241 caagctgccg ataagtatct ctatgtggat aaaaacttca tcaacaatcc gctggcccag
 301 gccgactggg ctgccaagaa gctggtatgg gtgccttccg acaagagtgg ctttgagcca
 361 gccagcctca aggaggaggt gggcgaagag ccatcgtgg agctggtgga gaatgggaag
 421 aaggtgaagg tgaacaagga tgacatccag aagatgaacc cgcccaagtt ctccaaggtg
 481 gaggacatgg cagagctcac gtgcctcaac gaagcctcgg tgctgcacaa cctcaaggag
 541 cgttactact cagggctcat ctacacctat tcaggcctgt tctgtgtggt catcaatcct
 601 tacaagaacc tgcccatcta ctctgaagag attgtggaaa tgtacaaggg caagaagagg
 661 cacgagatgc cccctcacat ctatgccatc acagacaccg cctacaggag tatgatgcaa
 721 gaccgagaag atcaatccat cttgtgcact ggtgaatctg agctggcaa gacggagaac
 781 accaagaagg tcatccagta tctggcgtac gtggcgtcct cgcacaagag caagaaggac
 841 cagggcgagc tggagcggca gctgctgcag gccaaccca tcctggaggc cttcgggaac
 901 gccaagaccg tgaagaatga caactcctcc cgcttcggca aattcattcg catcaacttt
 961 gatgtcaatg gctacattgt tggagccaac attgagactt atcttttgga gaaatctcgt
1021 gctatccgcc aagccaagga agaacggacc ttccacatct tctattatct cctgtctggg
1081 gctggagagc acctgaagac cgatctcctg ttggagccgt acaacaaata ccgcttcctg
1141 tccaatggac acgtcaccat ccccgggcag caggacaagg acatgttcca ggagaccatg
1201 gaggccatga ggattatggg catcccagaa gaggagcaaa tgggcctgct gcgggtcatc
1261 tcagggttc ttcagctcgg caacatcgtc ttcaagaagg agcggaacac tgaccaggcg
1321 tccatgccg acaacacagc tgcccaaaag gtgtcccatc tcttgggtat caatgtgacc
1381 gatttcacca gaggaatcct caccccgcgc atcaaggtgg acggatta cgtccagaag
1441 gcgcagacta aagagcaggc tgactttgcc atcgaggcct ggccaaggc gacctatgag
1501 cggatgttcc gctggctggt gctgcgcatc aacaaggctc tggacaagac caagaggcag
1561 ggcgcctcct tcatcgggat cctggacatt gccggcttcg agatctttga tctgaactcg
1621 tttgagcagc tgtgcatcaa ttacaccaat gagaagctgc agcagctctt caaccacacc
1681 atgttcatcc tggagcagga ggagtaccag cgcgagggca tcgagtggaa cttcatcgac
1741 tttggcctcg acctgcagcc ctgcatcgac ctcattgaga gccagcagg ccccccgggc
1801 attctggccc tgctggacga ggagtgctgg ttccccaaag ccaccgacaa gagcttcgtg
1861 gagaaggtga tgcaggagca gggcacccac ccaagttcc agaagcccaa gcagctgaag
1921 gacaaagctg atttctgcat tatccactat gccggcaagg tggattacaa gctgacgag
1981 tggctgatga agaacatgga tccctgaat gacaacatcg ccacactgct ccaccagtcc
2041 tctgacaagt ttgtctcgga gctgtggaag gatgtggacc gcatcatcgg cctggaccag
2101 gtggccggca tgtcggagac cgcactgccc ggggccttca gacgcggaa gggcatgttc
2161 cgcactgtgg ggcagcttta caaggagcag ctggccaagc tgatggctac gctgaggaac
2221 acgaacccca actttgtccg ctgcatcatc cccaaccacg agaagaaggc cggcaagctg
2281 gacccgcatc tcgtgctgga ccagctgcgc tgcaacgtg ttctcgaggg catccgtatc
2341 tgccgccagg gcttccccaa cagggtggtc ttccaggagt tcggcagag atatgagatc
2401 ctgactccaa actccattcc caagggtttc atggacggga gcaggcgtg cgtgctcatg
2461 ataaaagccc tggagctcga cagcaatctg taccgcattg gcagagcaa agtcttcttc
2521 cgtgccggtg tgctggccca cctggaggag gagcgagacc tgaagatcac cgacgtcatc
2581 atagggttcc aggcctgctg caggggctac ctggccagga agcatttgc caagcggcag
2641 cagcagctta ccgccatgaa ggtcctccag cggaactgcg ctgcctacct gaagctgcgg
2701 aactggcagt ggtggcggct cttcaccaag gtcaagccgc tgctgcaggt gagccggcag
2761 gaggaggaga tgatggccaa ggaggaggag ctggtgaagg tcagagagaa gcagctggct
2821 gcggagaaca ggctcacgga gatggagacg ctgcagtctc agctcatggc agagaaattg
2881 cagctgcagg agcagctcca ggcagaaacc gagctgtgtg ccgagctga ggagctccgg
2941 gcccgcctga ccgccaagaa gcaggaatta gaagagatct gccatgacct agaggccagg
3001 gtggaggagg aggaggagcg ctgccagcac ctgcaggcgg agaagaagaa gatgcagcag
3061 aacatccagg agcttgagga gcagctggag gaggaggaga gcgcccggca gaagctgcag
3121 ctggagaagg tgaccaccga ggcgaagctg aaaaagctgg aggaggagca gatcatcctg
3181 gaggaccaga actgcaagct ggccaaggaa aagaaactgc tggaagacag aatagctgag
```

FIG. 7B

```
3241 ttcaccacca acctcacaga agaggaggag aaatctaaga gcctcgccaa gctcaagaac
3301 aagcatgagg caatgatcac tgacttggaa gagcgcctcc gcagggagga gaagcagcga
3361 caggagctgg agaagacccg ccggaagctg gagggagact ccacagacct cagcgaccag
3421 atcgccgagc tccaggccca gatcgcggag ctcaagatgc agctggccaa gaaagaggag
3481 gagctccagg ccgccctggc cagagtggaa gaggaagctg cccagaagaa catggccctc
3541 aagaagatcc gggagctgga atctcagatc tctgaactcc aggaagacct ggagtctgag
3601 cgtgcttcca ggaataaagc tgagaagcag aaacgggacc ttggggaaga gctagaggct
3661 ctgaaaacag agttggagga cacgctggat tccacagctg cccagcagga gctcaggtca
3721 aaacgtgagc aggaggtgaa catcctgaag aagaccctgg aggaggaggc caagacccac
3781 gaggcccaga tccaggagat gaggcagaag cactcacagg ccgtggagga gctggcggag
3841 cagctggagc agacgaagcg ggtgaaagca aacctcgaga aggcaaagca gactctggag
3901 aacgagcggg gggagctggc caacgaggtg aaggtgctgc tgcagggcaa aggggactcg
3961 gagcacaagc gcaagaaagt ggaggcgcag ctgcaggagc tgcaggtcaa gttcaacgag
4021 ggagagcgcg tgcgcacaga gctggccgac aaggtcacca gctgcaggt ggagctggac
4081 aacgtgaccg gcttctcag ccagtccgac agcaagtcca gcaagctcac caaggacttc
4141 tccgcgctgg agtcccagct gcaggacact caggagctgc tgcaggagga gaaccggcag
4201 aagctgagcc tgagcaccaa gctcaagcag gtggaggacg agaagaattc cttccgggag
4261 cagctggagg aggaggagga ggccaagcac aacctggaga gcagatcgc caccctccat
4321 gcccaggtgg ccgacatgaa aaagaagatg gaggacagtg tggggtgcct ggaaactgct
4381 gaggaggtga agaggaagct ccagaaggac ctggagggcc tgagccagcg gcacgaggag
4441 aaggtggccg cctacgacaa gctggagaag accaagacgc ggctgcagca ggagctggac
4501 gacctgctgg tggacctgga ccaccagcgc cagagcgcgt gcaacctgga agaagaagcag
4561 aagaagtttg accagctcct ggcggaggag aagaccatct ctgccaagta tgcagaggag
4621 cgcgaccggg ctgaggcgga ggcccgagag aaggagacca aggctctgtc gctggcccgg
4681 gccctggagg aagccatgga gcagaaggcg gagctggagc ggctcaacaa gcagttccgc
4741 acggagatgg aggacttat gagctccaag gatgatgtgg gcaagagtgt ccacgagctg
4801 gagaagtcca gcgggccct agagcagcag gtggaggaga tgaagacgca gctggaagag
4861 ctggaggacg agctgcaggc caccgaagat gccaagctgc ggttggaggt caacctgcag
4921 gccatgaagg cccagttcga gcgggacctg caggccgggg acgagcagag cgaggagaag
4981 aagaagcagc tggtcagaca ggtgcgggag atggaggcag agctggagga cgagaggaag
5041 cagcgctcga tgcagtggc cgcccggaag aagctggaga tggacctgaa ggacctggag
5101 gcgcacatcg actcggccaa caagaaccgg gacgaagcca tcaaacagct gcggaagctg
5161 caggcccaga tgaaggactg catgcgcgag ctggatgaca cccgcgcctc tcgtgaggag
5221 atcctggccc aggccaaaga aacgagaag aagctgaaga gcatggaggc cgagatgatc
5281 cagttgcagg aggaactggc agccgcggag cgtgccaagc gccagcccca gcaggagcgg
5341 gatgagctgg ctgacgagat cgccaacagc agcggcaaag gagccctggc gttagaggag
5401 aagcggcgtc tggagcccg catcgcccag ctggaggagg agctggagga ggagcagggc
5461 aacacggagc tgatcaacga ccggctgaag aaggccaacc tgcagatcga ccagatcaac
5521 accgacctga acctggagcg cagccacgcc cagaagaacg agaatgctcg gcagcagctg
5581 gaacgccaga acaaggagct taaggtcaag ctgcaggaga tggaggcac tgtcaagtcc
5641 aagtacaagg cctccatcac cgccctcgag gccaagattg cacagctgga ggagcagctg
5701 gacaacgaga ccaaggagcg ccaggcagcc tgcaaacagg tgcgtcggac cgagaagaag
5761 ctgaaggatg tgctgctgca ggtggatgac gagcggagga acgccgagca gtacaaggac
5821 caggccgaca aggcatctac ccgcctgaag cagctcaagc ggcagctgga ggaggccgaa
5881 gaggaggccc agcgggccaa cgcctcccgc cggaaactgc agcgcgagct ggaggacgcc
5941 actgagacgg ccgatgccat gaaccgcgaa gtcagctccc taaagaacaa gctcaggcgc
6001 gggacctgc cgtttgtcgt gcccgccga atggcccgga aggcgccgg ggatggctcc
6061 gacgaagagg tagatggcaa agcggatggg gctgaggcca acctgccga ataagcctct
6121 tctcctgcag cctgagatgg atggacagac agacaccaca gcctcccctt cccagacccc
6181 gcagcacgcc ctcccccacc ttcttgggac tgctgtgaac atgcctcctc ctgccctccg
6241 ccccgtcccc ccatccgtt tccctccagg tgttgttgag ggcatttggc ttcctctgct
6301 gcatccccttt ccagctccct ccctgctca gaatctgata ccaaagagac agggcccggg
6361 cccaggcaga gagcgaccag caggctcctc agccctctct tgccaaaaag cacaagatgt
```

FIG. 7C

```
6421 tgaggcgagc agggcaggcc cccggggagg ggccagagtt ttctatgaat ctattttct
6481 tcagactgag gccttttggt agtcggagcc cccgcagtcg tcagcctccc tgacgtctgc
6541 caccagcgcc cccactcctc ctcctttctt tgctgtttgc aatcacacgt ggtgacctca
6601 cacacctctg ccccttgggc ctcccactcc catggctctg ggcggtccag aaggagcagg
6661 ccctgggcct ccacctctgt gcagggcaca gaaggctggg gtgggggag gagtggattc
6721 ctccccaccc tgtcccaggc agcgccactg tccgctgtct ccctcctgat tctaaaatgt
6781 ctcaagtgca atgccccctc ccctccttta ccgaggacag cctgcctctg ccacagcaag
6841 gctgtcgggg tcaagctgga aaggccagca gccttccagt ggcttctccc aacactcttg
6901 gggaccaaat atatttaatg gttaagggac ttgtcccaag tctgacagcc agagcgttag
6961 aggggccagc ggccctccca ggcgatcttg tgtctactct aggactgggc ccgagggtgg
7021 tttacctgca ccgttgactc agtatagttt aaaaatctgc cacctgcaca ggtattttg
7081 aaagcaaaat aaggttttct ttttccct ttcttgtaat aaatgataaa attccgagtc
7141 tttctcactg cctttgttta gaagagagta gctcgtcctc actggtctac actggttgcc
7201 gaatttactt gtattcctaa ctgttttgta tatgctgcat tgagacttac ggcaagaagg
7261 catttttttt ttttaagga aacaaactct caaatcatga agtgatataa aagctgcata
7321 tgcctacaaa gctctgaatt caggtcccag ttgctgtcac aaaggagtga gtgaaactcc
7381 caccctaccc ccttttttat ataataaaag tgccttagca tgtgttgcag ctgtcaccac
7441 tacagtaagc tggtttacag atgttttcca ctgagcatca caataaagag aaccatgtgc
7501 tacga
```

FIG. 7D

MODULATION OF UL24 INTERACTIONS WITH PROTEIN TARGETS AND USES THEREOF FOR INHIBITION OF HERPESVIRUS INFECTION

CROSS REFERENCE TO RELATED APPLICATIONS

This application claims the benefit of U.S. provisional application Ser. No. 61/552,110, filed on Oct. 27, 2011, which is incorporated herein by reference in its entirety.

TECHNICAL FIELD

The present invention generally relates to Herpes simplex virus (HSV) infection, and more particularly to methods for the treatment of HSV infection and for the identification of inhibitors of HSV.

SEQUENCE LISTING

Pursuant to 37 C.F.R. 1.821(c), a sequence listing is submitted herewith as an ASCII compliant text file named "10371.115—Sequence listing_ST25", created on Oct. 23, 2012 and having a size of ~60 kilobytes. The content of the aforementioned file is hereby incorporated by reference in its entirety.

BACKGROUND ART

The herpesviruses (Herpesviridae) are a large family of DNA viruses that cause diseases in animals, including humans. Herpes simplex virus 1 (HSV-1) is a member of the herpesvirus family that infect humans. HSV-1 infection causes cold sores and the primary infection results in viral persistence/latency in the innervating neurons. The consequences of HSV-1 infection can be severe in cases of eye involvement, resulting in keratitis and in some cases blindness (Liesegang, T. J. 2001. Cornea 20:1-13). Although rare, HSV-1 can also cause encephalitis in immunocompetent individuals. In immunosuppressed patients and in newborns, infections are often severe and can also include extensive herpetic plaques and disseminated infections (Fatahzadeh, M., and R. A. Schwartz. 2007. J Am Acad Dermatol 57:737-63; quiz 764-6).

Herpesviruses establish lifelong infections and the virus cannot currently be eradicated from the body. Treatment usually involves general-purpose antiviral drugs that interfere with viral replication, reducing the physical severity of outbreak-associated lesions and lowering the chance of transmission to others.

There is thus a need for the development of novel strategies for interfering with herpesvirus infection and for the identification of agents capable of inhibiting infection by herpesviruses.

The present description refers to a number of documents, the content of which is herein incorporated by reference in their entirety.

SUMMARY OF THE INVENTION

In a first aspect, the present invention provides a method for treating herpesvirus infection, said method comprising administering to a subject in need thereof an effective amount of an agent that inhibit the interaction between herpesvirus UL24 and non-muscle myosin type IIa (NM2a).

In another aspect, the present invention provides the use of an agent that inhibit the interaction between herpesvirus UL24 and non-muscle myosin type IIa (NM2a) for treating herpesvirus infection in a subject.

In another aspect, the present invention provides the use of an agent that inhibit the interaction between herpesvirus UL24 and non-muscle myosin type IIa (NM2a) for the manufacture of a medicament for treating herpesvirus infection in a subject.

In an embodiment, the above-mentioned agent is an antibody. In an embodiment, the above-mentioned antibody is an antibody specifically binding to UL24.

In another embodiment, the above-mentioned antibody is an antibody specifically binding to NM2a. In an embodiment, the above-mentioned antibody specifically binding to the non-muscle myosin heavy chain IIA (NMHC-IIA) of NM2a.

In an embodiment, the above-mentioned agent is a peptide. In a further embodiment, the above-mentioned peptide comprises an amino acid sequence derived from a UL24 polypeptide. In a further embodiment, the above-mentioned peptide comprises an amino acid sequence derived from the amino acid sequence depicted in FIG. 6A (SEQ ID NO:2).

In another embodiment, the above-mentioned peptide comprises an amino acid sequence derived from an NM2a polypeptide. In a further embodiment, the above-mentioned NM2a polypeptide is an NMHC-IIA polypeptide.

In a further embodiment, the above-mentioned peptide comprises an amino acid sequence derived from the amino acid sequence depicted in FIG. 7A (SEQ ID NO:4).

In another aspect, the present invention provides a method for determining whether an agent may be useful for the treatment of herpesvirus infection, said method comprising determining whether said agent inhibits the interaction between herpesvirus UL24 and non-muscle myosin type IIa (NM2a), wherein an inhibition of said interaction is indicative that said agent may be useful for the treatment of herpesvirus infection.

In an embodiment, the above-mentioned method comprises contacting a UL24 polypeptide and an NM2a polypeptide in the presence of said agent, and determining whether the interaction between said UL24 and NM2a polypeptides is inhibited in the presence of said agent, wherein inhibition of the interaction between said UL24 and NM2a polypeptides in the presence of said agent is indicative that said agent may be useful for the treatment of herpesvirus infection.

In another embodiment, the above-mentioned method comprises contacting a cell comprising a UL24 polypeptide and an NM2a polypeptide with said agent, and determining whether the interaction between said UL24 and NM2a polypeptides is inhibited in the presence of said agent, wherein inhibition of the interaction between said UL24 and NM2a polypeptides in the presence of said agent is indicative that said agent may be useful for the treatment of herpesvirus infection.

In an embodiment, the above-mentioned cell is a cell transfected or transformed with (i) a nucleic acid encoding said UL24 polypeptide; (ii) a nucleic acid encoding said NM2a polypeptide; or (iii) both (i) and (ii).

In an embodiment, the above-mentioned NM2a polypeptide is an NMHC-IIA polypeptide. In a further embodiment, the above-mentioned NMHC-IIA polypeptide comprises an amino acid sequence derived from the amino acid sequence depicted in FIG. 7A (SEQ ID NO:4).

In an embodiment, the above-mentioned UL24 polypeptide comprises an amino acid sequence derived from the amino acid sequence depicted in FIG. 6A (SEQ ID NO:2).

In an embodiment, the above-mentioned herpesvirus infection is herpes simplex virus (HSV) infection. In a further embodiment, the above-mentioned HSV infection is HSV-1 infection.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1A: Samples of the fractions were analyzed by Western blot with an antibody directed against HA, to detect HA-UL24. The arrow on the right of the panel indicates the position of HA-UL24. Fractions to the left represent the bottom of the gradient (high sedimentation coefficient) and to the right, the top of the gradient (low sedimentation coefficient). The arrows above the panel denote lanes corresponding to the peak UL24 fractions. FIG. 1B: Samples taken from the same fractions were also resolved by SDS-PAGE followed by staining with silver to show the total protein separation profile. The position of the molecular weight markers are indicated to the left of the panels.

FIGS. 2A to 2C show the affinity purification of UL24-interacting partners. FIG. 2A: Silver stained gel of co-immunoprecipitated proteins following anti-HA precipitation. Lanes 1-4 show the samples of the whole extracts from KOS- and vHA-UL24-infected Vero and HeLa cells. Lanes 5-8 show the proteins obtained following immunoprecipitation with an anti-HA affinity matrix. The arrow indicates a co-immunoprecipitated protein of approximately 200 kDa. FIG. 2B: Identification by mass spectrometry of NM2a from the 26 peptides listed (SEQ ID NOs:5-30). FIG. 2C: The fractions from the glycerol gradient used in FIG. 1 were subjected to immunoblotting for NM2a. Arrows indicate wells corresponding to peak UL24 fractions.

FIGS. 4A and 4B show the partial co-localization of UL24 and NM2a. FIG. 4A: HeLa cells were either mock-transfected (top panels) or transfected with a mammalian expression vector for HA-UL24 (pLB-HA-UL24) (bottom panels) and then co-immunostained for HA and NM2a. FIG. 4B: Mock- (top panels) and vHA-UL24-infected (bottom panels) Vero cells were fixed at 12 hpi and co-immunostained for HA and NM2a. Nuclei were stained with Draq5. Merged images are shown in the right hand panels. Arrows indicate areas of co-localization.

FIG. 5A: gB and NM2a co-localization in cells infected with KOS (top panels) or UL24X (bottom panels). FIGS. 5C and 5E: gD and gL co-localization with NM2a under the same conditions. FIG. 5B: Quantification of the co-localization of gB and NM2a according to the Mander's coefficient. A total of 10 fields of view were analyzed, which represents more than 32 cells total per condition. FIGS. 5D and 5F: Graphs representing the quantification for gD and gL as described for FIG. 5B. ***=p<0.0001.

FIG. 6A shows the amino acid sequence of herpesvirus 1 nuclear protein UL24 (NCBI Reference Sequence: NP_044625.1, SEQ ID NO: 2).

FIG. 6B shows the nucleotide sequence of herpesvirus 1 nuclear protein UL24 (NCBI Reference Sequence: NC_001806.1, nucleotides 47737-48546, SEQ ID NO: 1).

FIG. 7A shows the amino acid sequence of human non-muscle myosin heavy chain II-A (NCBI Reference Sequence: NP_002464.1, SEQ ID NO:4).

FIGS. 7B to D show the nucleotide sequence of human non-muscle myosin heavy chain II-A encoding nucleic acid (NCBI Reference Sequence: NM_002473.4, nucleotides coding region 232-6114, SEQ ID NO:3).

(FIG. 9A) 34° C., (FIG. 9B) 37° C., and (FIG. 9C) 39° C. For each temperature, cells were processed for immunofluorescence using antibodies directed against different components of the Golgi apparatus, namely GM130, mannosidase II, and Golgin 97. Secondary antibodies used were conjugated to Alexa™ 488. Nuclei were stained with DRAQ5™ (blue). Scale bars represent 10 microns. (FIG. 9D) Quantification of staining patterns observed for the cis-Golgi marker GM130 in HFFs infected with either KOS or UL24X at 34, 37 and 39° C. Histograms show the percentage of fields of view for each category; more than 100 cells were analysed for each.

DISCLOSURE OF INVENTION

The invention described herein is based on the demonstration by the present inventors that the UL24 protein of HSV-1 forms a complex with non-muscle myosin type II A (NM2a) and affects its association with viral glycoprotein B (gB). In the absence of UL24, there is a decrease in the association between NM2a and gB, which in turn may lead to unregulated cell-cell fusion, decreased viral replication efficiency and/or decreased viral spread.

Accordingly, in a first aspect, the present invention provides a method for treating herpesvirus infection in a subject, the method comprising administering an effective amount of an agent that inhibits the interaction between herpesvirus UL24 and Non-muscle Myosin Type II a (NM2a).

In another aspect, the present invention provides the use an agent that inhibits the interaction between herpesvirus UL24 and Non-muscle Myosin Type II a (NM2a) for treating herpesvirus infection in a subject.

In another aspect, the present invention provides the use an agent that inhibits the interaction between herpesvirus UL24 and Non-muscle Myosin Type II a (NM2a) for the manufacture of a medicament for treating herpesvirus infection in a subject.

In another aspect, the present invention provides an agent that inhibits the interaction between herpesvirus UL24 and Non-muscle Myosin Type II a (NM2a) for the manufacture of a medicament for treating herpesvirus infection in a subject.

In another aspect, the present invention provides an agent that inhibits the interaction between herpesvirus UL24 and Non-muscle Myosin Type II a (NM2a) for treating herpesvirus infection in a subject.

In another aspect, the present invention provides a method for inhibiting cell-to-cell spread of herpesvirus, the method comprising contacting a herpesvirus-infected cell with an agent that inhibits the interaction between herpesvirus UL24 and Non-muscle Myosin Type II a (NM2a).

In another aspect, the present invention provides the use an agent that inhibits the interaction between herpesvirus UL24 and Non-muscle Myosin Type II a (NM2a) for inhibiting cell-to-cell spread of herpesvirus.

In another aspect, the present invention provides the use an agent that inhibits the interaction between herpesvirus UL24 and Non-muscle Myosin Type II a (NM2a) for the manufacture of a medicament for inhibiting cell-to-cell spread of herpesvirus.

In another aspect, the present invention provides an agent that inhibits the interaction between herpesvirus UL24 and Non-muscle Myosin Type II a (NM2a) for the manufacture of a medicament for inhibiting cell-to-cell spread of herpesvirus.

In another aspect, the present invention provides an agent that inhibits the interaction between herpesvirus UL24 and Non-muscle Myosin Type II a (NM2a) for inhibiting cell-to-cell spread of herpesvirus.

Figure 1:
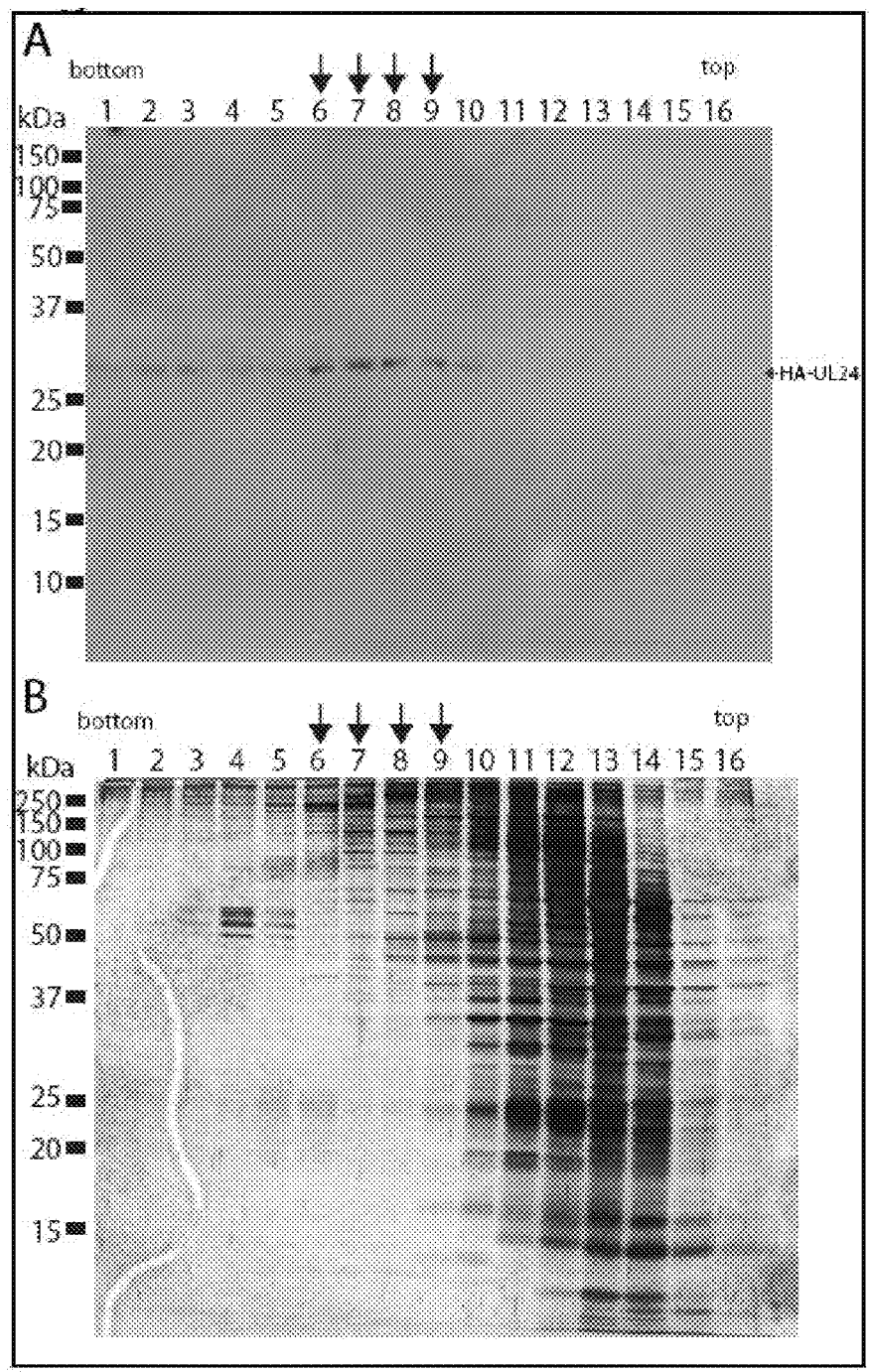
FIGS. 1A and 1B shows glycerol gradient fractionation of UL24-containing complexes. Cell extracts from Vero cells infected with vHA-UL24 for 18 hours were fractionated on a 8%-25% continuous glycerol gradient.

UL24, the $24^{th}$ open reading frame in the unique long region of the viral genome, is involved in pathogenicity in a mouse model of infection (Blakeney, S. et al., 2005. *J Virol* 79:10498-506; Leiva-Torres, G. A. et al., 2010 *J Gen Virol* 91:1109-1116), in viral replication in the mucous membranes, and in high viral titers in neurons (Jacobson, J. G., et al. 1998. *Virology* 242:161-9). This gene is conserved throughout the Herpesviridae family, with possibly one exception (Davison, A. J. 1992. *Virology* 186:9-14). HSV-1 UL24 is a protein of 269 amino acids that contains five homology domains (HD) (Jacobson, J. G., et al. 1989. *J Virol* 63:1839-43), which consists of stretches of amino acids with a high percentage of identity between homologs, and a PD-(D/E)XK endonuclease motif (Knizewski, L., 2006. *J Virol* 80:2575-7, amino acid sequence alignment of UL24 proteins from various herpesvirus are depicted in FIG. 1 of this paper). In the absence of UL24, HSV-1 forms small plaques (Jacobson, J. G., et al. 1989. *J Virol* 63:1839-43). Furthermore, it is one of four HSV-1 proteins, along with gB, gK and UL20, whose altered function appears to be associated with a syncytial phenotype (Baines, J. D., et al. 1991. *J Virol* 65:6414-24; Bzik, D. J., et al. 1984. *Virology* 137:185-90; Ruyechan, W. T., et al. 1979. *J Virol* 29:677-97; Tognon, M., R. et al. 1991. *Virus Res* 18:135-50). While gB has been shown to be a fusion protein and can induce syncytia formation (Diakidi-Kosta, A., et al. 2003. *Virus Res* 93:99-108, Engel, J. P., et al. *Virology* 192:112-20, Goodman, J. L., and J. P. Engel. 1991. *J Virol* 65:1770-8), UL24, gK and UL20 have an inhibitory role on cell-cell fusion (Avitabile, E., et al. 2004. *J Virol* 78:8015-25, Jacobson, J. G., et al. 1989. supra). UL24 protein localizes to the nucleus, nucleolus and cytoplasm during infection (Lymberopoulos, M. H., and A. Pearson. 2007. *Virology* 363:397-409), and a similar localization is observed upon transient expression of the protein in COS-7 cells, in addition to trans-Golgi localization (Bertrand, L., and A. Pearson. 2008. *J Gen Virol* 89:1142-51). The amino acid and nucleotide sequence of UL24 are depicted in FIGS. 6A and 6B (SEQ ID NOs:2 and 1), respectively.

Non-muscle Myosin Type II a (NM2a or NM-IIA) is a cytoskeletal protein comprising six subunits, namely two identical heavy chains (Non-muscle myosin heavy chain IIA, NMHC-IIA, also known as MYH9) and two pairs of light chains, two regulatory light chains (RLCs), and two essential light chains (ELCs). NM2a is involved in cell adhesion, cell migration/motility, maintenance of cell shape and tissue architecture. The amino acid and nucleotide sequence of NMHC-IIA are depicted in FIGS. 7A and 7B-D (SEQ ID NOs:4 and 3), respectively.

The terms "treat/treating/treatment" as used herein, refers to eliciting the desired biological response, i.e., a therapeutic effect, respectively. In accordance with the subject invention, the therapeutic effect comprises one or more of a decrease/reduction in viral load, a decrease/reduction in the severity of the symptoms and herpesvirus infection-related effects, an amelioration of symptoms and herpesvirus infection-related effects, a decrease in viral dissemination, a decrease in the duration of infection, prolongation of the latency to a relapse of an herpesvirus infection, following administration of the agent/composition of the invention.

As used herein, "inhibition" or "decrease" interaction between UL24 and NM2a (e.g., NMHC-IIA) refers to a reduction in binding of at least 10% as compared to reference (e.g., in the absence of the agent), in an embodiment of at least 20%, in a further embodiment of at least 30%, in a further embodiment of at least 40%, in a further embodiment of at least 50%, in a further embodiment of at least 60%, in a further embodiment of at least 70%, in a further embodiment of at least 80%, in a further embodiment of at least 90%, in a further embodiment of 100% (complete inhibition of the interaction/binding between UL24 and NM2a (e.g., NMHC-IIA)).

As used herein, the term "agent that inhibits the interaction between UL24 and NM2a" includes any compound able to affect the binding of UL24 to NM2a (e.g., NMHC-IIA), and includes proteins, peptides, small molecules, antibodies, etc. Such agent may either directly bind to the regions of UL24 and/or NM2a (e.g., NMHC-IIA) polypeptides involved in the interaction, or may indirectly interfere with the interaction by creating steric hindrance for example. In an embodiment, the agent is a peptide or an antibody (blocking peptide or antibody).

In an embodiment, the agent is a peptide, for example a peptide derived from UL24 (e.g., a peptide derived from the amino acid sequence of FIG. 6A or SEQ ID NO:2) or NM2a (e.g., NMHC-IIA) (e.g., a fragment derived from the amino acid sequence of FIG. 7A or SEQ ID NO:4). Such peptide may for example compete with native UL24 for binding to NM2a (e.g., NMHC-IIA), or compete with native NM2a (e.g., NMHC-IIA) for binding to UL24. In embodiments, the peptide comprises from about 5 to about 300, 200, 150, 100, 90, 80, 70, 60, 50, 40, 30, or 20 amino acids, for example from about 10, 15, 20 to about 50, 45, 40, 35, 30 or 25 amino acids. In an embodiment, the peptide comprises a sequence corresponding to the regions of UL24 and/or NM2a (e.g., NMHC-IIA) polypeptides involved in the interaction.

The peptide of the present invention may be prepared by conventional synthetic methods or recombinant DNA technologies. The methods for synthetic production of peptides are well known in art. Chemically modified amino acids are used for incorporation into compounds to enhance one or more properties, such as protease resistance, pharmacokinetics or affinity for its molecular target. Detailed descriptions as well as practical advice for producing synthetic peptides may be found in Synthetic Peptides: A User's Guide (Advances in Molecular Biology), Grant G. A. ed., Oxford University Press, 2002, or in Pharmaceutical Formulation Development of Peptides and Proteins, Frokjaer and Hovgaard eds., Taylor and Francis, 1999.

In another embodiment, the above-mentioned agent is an antibody that binds to a UL24 protein and/or an NM2a (e.g., NMHC-IIA) protein, and inhibits their interaction (blocking antibody). In an embodiment, the antibody binds to an epitope from the amino acid sequence of FIG. 6A or 7A (SEQ ID NOs: 2 or 4). The term antibody is used in the broadest sense, and refers to monoclonal antibodies (including full-length monoclonal antibodies), polyclonal antibodies, multispecific antibodies, and antibody fragments so long as they exhibit the desired biological activity (inhibiting UL24-NM2a interaction). Antibody fragments comprise a portion of a full-length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anti-calins, PepBodies, antibody-T-cell epitope fusions (Troybodies) or Peptibodies. In an embodiment, the antibody is a monoclonal or polyclonal antibody. In a further embodiment, the antibody is a monoclonal antibody.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories).

Polyclonal antibodies are preferably raised in animals by multiple subcutaneous (s.c.), intravenous (i.v.) or intraperitoneal (i.p.) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen (UL24 or NM2a (e.g., NMHC-IIA) polypeptide, or fragments thereof), immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with 1/5 to 1/10 of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025, 155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In an embodiment, the above-mentioned agent that inhibits the interaction between UL24 and NM2a (e.g., NMHC-IIA)

may also be in the form of non-antibody-based scaffolds, such as avimers (Avidia); DARPins (Molecular Partners); Adnectins (Adnexus), Anticalins (Pieris) and Affibodies (Affibody). The use of alternative scaffolds for protein binding is well known in the art (see, for example, Binz and Plückthun, 2005, *Curr. Opin. Biotech.* 16: 1-11).

The invention also provides a pharmaceutical composition (medicament) comprising the above-mentioned agent that inhibits the interaction between UL24 and NM2a (e.g., NMHC-IIA), and a pharmaceutically acceptable diluent, carrier, salt or adjuvant. Such carriers include, for example, saline, buffered saline, dextrose, water, glycerol, ethanol, and combinations thereof. The pharmaceutical composition can be delivered in any suitable dosage form, such as a liquid, gel, solid, cream, or paste dosage form. In one embodiment, the compositions can be adapted to give sustained release of the agent.

In some embodiments, the pharmaceutical compositions include, but are not limited to, those forms suitable for oral, rectal, nasal, topical, (including buccal and sublingual), transdermal, vaginal, or parenteral (including intramuscular, subcutaneous, and intravenous) administration, in a form suitable for administration by inhalation or insufflation, or injection into amniotic fluid. The compositions can, where appropriate, be conveniently provided in discrete dosage units. The pharmaceutical compositions of the invention can be prepared by any of the methods well known in the pharmaceutical arts.

Pharmaceutical formulations suitable for oral administration include capsules, cachets, or tablets, each containing a predetermined amount of one or more of the peptides, as a powder or granules. In another embodiment, the oral composition is a solution, a suspension, or an emulsion. Alternatively, the peptides can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like.

Pharmaceutical compositions for parenteral administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agent, and dispersing agents. Alternatively, the peptides can be provided in powder form, obtained by aseptic isolation of sterile solid or by lyophilization from solution, for constitution with a suitable vehicle, e.g. sterile, pyrogen-free water, before use.

Pharmaceutical compositions for topical administration of the agent to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. Such gels can be used, for example, in a personal lubricant composition containing the agent and optionally including one or more other antiviral agents, for preventing or inhibiting sexual transmission of a herpesvirus infection. In addition, lotions, creams and gels including an agent of the present invention can be utilized for topical application to a lesion from a herpesvirus outbreak.

Pharmaceutical compositions suitable for topical administration in the mouth (e.g., buccal or sublingual administration) include lozenges comprising the agent in a flavored base, such as sucrose, acacia, or tragacanth; pastilles comprising the agent in an inert base such as gelatin and glycerin or sucrose and acacia; and mouthwashes comprising the agent in a suitable liquid carrier. The pharmaceutical compositions for topical administration in the mouth can include penetration enhancing agents, if desired.

A pharmaceutical composition suitable for rectal administration comprises an agent of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art.

According to one embodiment, pharmaceutical compositions of the present invention suitable for vaginal administration are provided as pessaries, tampons, creams, gels, pastes, foams, or sprays containing a peptide of the invention in combination with a carriers as are known in the art. Alternatively, compositions suitable for vaginal administration can be delivered in a liquid or solid dosage form.

Pharmaceutical compositions suitable for intra-nasal administration are also encompassed by the present invention. Such intra-nasal compositions comprise an agent of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the peptide. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the agent. Alternatively, pharmaceutical compositions for administration by inhalation or insufflation can be provided in the form of a dry powder composition, for example, a powder mix of the agent and a suitable powder base such as lactose or starch. Such powder composition can be provided in unit dosage form, for example, in capsules, cartridges, gelatin packs, or blister packs, from which the powder can be administered with the aid of an inhalator or insufflator.

In an embodiment, the pharmaceutical compositions of the present invention can include one or more other therapeutic agent, e.g., as a combination therapy. For example, the composition can include one or more other anti-infective agents in addition to the agent of the invention, such as, for example, an antiviral protease enzyme inhibitor (PI), a virus DNA or RNA or reverse transcriptase (RT) polymerase inhibitor, a virus/cell fusion inhibitor, a virus integrase enzyme inhibitor, a virus/cell binding inhibitor, a virus or cell helicase enzyme inhibitor, a bacterial cell wall biosynthesis inhibitor, a virus or bacterial attachment inhibitor, a herpesvirus DNA polymerase inhibitor (such as acyclovir, ganciclovir, cidofovir, and the like), a herpes virus protease inhibitor, a herpes virus fusion inhibitor, a herpes virus binding inhibitor, a ribonucleotide reductase inhibitor, and the like. The additional therapeutic agent will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with an agent of the present invention.

In an embodiment, the above-mentioned treatment comprises the use/administration of more than one (i.e., a combination of) active/therapeutic agent (e.g., agent that inhibits the interaction between UL24 and NM2a (e.g., NMHC-IIA)). The combination of therapeutic agents and/or compositions of the present invention may be administered or co-administered (e.g., consecutively, simultaneously, at different times) in any conventional dosage form. Co-administration in the context of the present invention refers to the administration of more than one prophylactic or therapeutic agent in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) of the present invention is used/administered in combination with one or more agent(s) currently used to prevent or treat the disorder in question (e.g., an antiviral agent used for treating herpesvirus infection, as described above).

The present invention further provides screening methods/assays for the identification and characterization of compounds/agents capable of agent that inhibits the interaction between UL24 and NM2a (e.g., NMHC-IIA), which may be used for the treatment of herpesvirus infection.

The present invention also provides a method (e.g., an in vitro method) for determining whether a test compound is useful for the treatment of herpesvirus infection, said method comprising: (a) determining the binding/interaction between a UL24 and/or NM2a (e.g., NMHC-IIA) polypeptide, or fragments thereof comprising the interacting region/domain, in the presence or absence of said test compound; wherein a decrease in the binding/interaction between UL24 and NM2a (e.g., NMHC-IIA), or fragments thereof or variants thereof, in the presence of said test compound relative to the absence thereof is indicative that said test compound may be used for the treatment of herpesvirus infection.

The present invention also provides a method (e.g., an in vitro method) for determining whether a test compound is useful for the treatment of herpesvirus infection, said method comprising: (a) contacting said test compound with a UL24 and/or NM2a (e.g., NMHC-IIA) polypeptide, or fragments thereof or variant thereof comprising the interacting region/domain; and (b) determining the binding/interaction between UL24 and/or NM2a (e.g., NMHC-IIA), or fragments thereof or variants thereof, in the presence or absence of said test compound; wherein a decrease in the binding/interaction (i.e. a lower level of binding/interaction) in the presence of said test compound relative to the absence thereof is indicative that said test compound may be used for the treatment of herpesvirus infection.

The present invention also provides a method (e.g., an in vitro method) for determining whether a test compound is useful for the treatment of herpesvirus infection, said method comprising: (a) contacting a cell comprising a UL24 polypeptide and an NM2a (e.g., NMHC-IIA) polypeptide; and (b) determining the binding/interaction between UL24 and/or NM2a (e.g., NMHC-IIA), or fragments thereof or variants thereof, in the presence or absence of said test compound; wherein a decrease in the binding/interaction (i.e. a lower level of binding/interaction) in the presence of said test compound relative to the absence thereof is indicative that said test compound may be used for the treatment of herpesvirus infection.

In an embodiment, the above-mentioned cell is a cell naturally expressing said UL24 and/or NM2a polypeptide. In another embodiment, the above-mentioned cell is a cell transfected, transduced or transformed with (i) a nucleic acid encoding said UL24 polypeptide; (ii) a nucleic acid encoding said NM2a polypeptide; or (iii) both (i) and (ii). The nucleic acids encoding said UL24 and/or NM2a polypeptide may be comprised within a vector/plasmid.

The vectors can be of any type suitable, e.g., for expression of said polypeptides or propagation of genes encoding said polypeptides in a particular organism. The organism may be of eukaryotic or prokaryotic origin. The specific choice of vector depends on the host organism and is known to a person skilled in the art. In an embodiment, the vector comprises transcriptional regulatory sequences or a promoter operably-linked to a nucleic acid comprising a sequence encoding a UL24 and/or NM2a polypeptide of the invention. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequence. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous. "Transcriptional regulatory sequences" or "transcriptional regulatory elements" are generic terms that refer to DNA sequences, such as initiation and termination signals, enhancers, and promoters, splicing signals, polyadenylation signals, etc., which induce or control transcription of protein coding sequences with which they are operably-linked.

A recombinant expression vector comprising the above-mentioned nucleic acid(s) may be introduced into a cell, e.g., a host cell, which may include a living cell capable of expressing the protein coding region from the defined recombinant expression vector. The suitable host cell may be any cell of eukaryotic or prokaryotic (bacterial) origin that is suitable, e.g., for expression of the UL24 and/or NM2a or propagation of genes/nucleic acids encoding the UL24 and/or NM2a polypeptide. The eukaryotic cell line may be of mammalian, of yeast, or invertebrate origin. The specific choice of cell line is known to a person skilled in the art. Choice of bacterial strain will depend on the task at hand and is known to a person skilled in the art.

Nucleic acids and vectors can be introduced into cells via conventional transformation, transduction or transfection techniques. The terms "transformation", "transduction" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al., Molecular Cloning: A Laboratory Manual, 3$^{rd}$ ed., New York, Cold Spring Harbor Laboratory, 2001) and other laboratory manuals. Reagents and kits for performing cell transfection are also commercially available.

The terms "UL24 polypeptide" and "NM2a polypeptide" as used herein include full length UL24 and NM2a polypeptide as well as fragments thereof comprising the interacting region/domain" (i.e., that comprises the region or domain involved in the interaction with the interacting partner, for example a fragment of UL24 comprising the region or domain involved in the interaction with NM2a (e.g., NMHC-IIA), or a fragment NM2a (e.g., NMHC-IIA) comprising the region or domain involved in the interaction with UL24). Therefore, in an embodiment, such fragments of UL24 and/or NM2a (e.g., NMHC-IIA) could be used in the above-mentioned methods. In an embodiment, the UL24 polypeptide comprises the amino sequence depicted in FIG. 6A (SEQ ID NO:2), or a fragment thereof having between about 10 to about 250 amino acids, in further embodiments having about 15, 20, 30, 40, 50, 60, 70, 80, 90, or 100 to about 200, 190, 180, 170, 160, 150, 140, 130, 120, or 110 amino acids. In an embodiment, the NMHC-IIA polypeptide comprises the amino sequence depicted in FIG. 7A (SEQ ID NO:4), or a fragment thereof having between about 10 to about 1600 amino acids, in further embodiments having about 15, 20, 30, 40, 50, 60, 70, 80, 90, or 100 to about 1500, 1400, 1300, 1200, 1100, 1000, 900, 800, 700, 600, 500, 400, 300, 200, 190, 180, 170, 160, 150, 140, 130, 120, or 110 amino acids. The terms "UL24 polypeptide" and "NM2a polypeptide" also include variants of UL24 and/or NM2a (e.g., NMHC-IIA) which retains the ability to interact with the interacting partner. Such variants shares significant sequence similarity/identity with a native UL24 polypeptide or NM2a polypeptide, or with a fragment thereof. Variants include, but are not limited to, proteins or peptides, which differ from a UL24 polypeptide or NM2a polypeptide (e.g., FIG. 6A, SEQ ID NO:2 or FIG. 7A, SEQ ID NO:4) by any modifications, and/or amino acid substitutions, deletions or additions. Modifications can occur anywhere including the polypeptide backbone, (i.e., the amino acid sequence), the amino acid side chains and the amino or carboxy termini. Such substitutions, deletions or additions may involve one or more amino acids. The UL24 polypeptide and/or NM2a polypeptide (or a variant or fragment thereof retaining the ability to interact with the corresponding interacting partner) may also be fused with another polypeptide or conjugated to one or more molecules.

"Identity" refers to sequence identity between two polypeptides or two nucleic acid molecules. Identity can be determined by comparing each position in the aligned sequences. A degree of identity between amino acid sequences is a function of the number of identical or matching amino acids at positions shared by the sequences. Two amino acid sequences are considered "substantially identical" if, when optimally aligned (with gaps permitted), they share at least about 50% sequence similarity or identity, in further embodiments at least about 60%, 70%, 75%, 80%, 85%, 90%, 95%, 96%, 97%, 98% or 99%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, amino acid sequences are considered substantially identical if the smallest sum probability in a comparison of the test sequences is less than about 1, preferably less than about 0.1, more preferably less than about 0.01, and most preferably less than about 0.001.

The above-mentioned methods may be employed either with a single test compound or a plurality or library (e.g., a combinatorial library) of test compounds. In the latter case, synergistic effects provided by combinations of compounds may also be identified and characterized. The above-mentioned compounds may be used for the treatment of herpesvirus infection, or may be used as lead compounds for the development and testing of additional compounds having improved specificity, efficacy and/or pharmacological (e.g., pharmacokinetic) properties. In an embodiment the compound may be a prodrug which is altered into its active form at the appropriate site of action, (e.g., a cell, tissue or organ affected by herpesvirus infection). In certain embodiments, one or a plurality of the steps of the screening/testing methods of the invention may be automated.

Such assay systems may comprise a variety of means to enable and optimize useful assay conditions. Such means may include but are not limited to: suitable buffer solutions, for example, for the control of pH and ionic strength and to provide any necessary components for optimal UL24 and/or NM2a (e.g., NMHC-IIA) stability (e.g., protease inhibitors), temperature control means for UL24 and/or NM2a (e.g., NMHC-IIA) stability, and detection means to enable the detection of UL24 and NM2a (e.g., NMHC-IIA) interaction.

Means to detect/quantify protein-protein interaction/binding (i.e. the interaction between UL24 and NM2a) are well known in the art, and include for example one or a combination of the following: radiolabelling (e.g., $^{32}P$, $^{14}C$, $^{3}H$), antibody-based detection, fluorescence (e.g. fluorescence resonance energy transfer, FRET), co-localization, chemiluminescence, spectroscopic methods (e.g., generation of a product with altered spectroscopic properties), enzyme-linked immunosorbant assay (ELISA), radioimmunoassay (RIA), immunoprecipitation, immunocytochemistry, immunohistochemistry, mass spectrometry, surface plasmon resonance (SPR), pull-down assays, ELISA, flow cytometry, yeast two-hybrid, phage display, affinity blotting, various reporter enzymes or proteins (e.g., horseradish peroxidase, green fluorescent protein), specific binding reagents (e.g., biotin/(strept)avidin), and others (see Phizicky and Fields, *Microbiological Reviews*, March 1995, p. 94-123; Shoemaker B A and Panchenko A R (2007). *PLoS Comput Biol* 3(3): e42).

The assay may be carried out in vitro utilizing a source of UL24 and/or NM2a (e.g., NMHC-IIA) which may comprise naturally isolated or recombinantly-produced UL24 and/or NM2a (e.g., NMHC-IIA), in preparations ranging from crude to pure. Recombinant UL24 and/or NM2a (e.g., NMHC-IIA) may be produced in a number of prokaryotic or eukaryotic expression systems, which are well known in the art.

The test compound may be any compound, macromolecule, such as a small molecule, a peptide, a polypeptide, an antibody or a fragment thereof.

Herpesvirus infection as used herein refers to infection by a virus of the Herpesviridae family. It includes herpesvirus infection in any animal (humans, monkeys, mice, cows, horses, dogs, etc.). Non-limiting examples of herpesviruses include, Bovine, Caprine, Porcine, Equine, Canine, Feline or Duck herpesviruses, as well as human herpesviruses such as Human Cytomegalovirus (HCMV), Herpes Simplex Virus 1 (HSV-1), Herpes Simplex Virus 2 (HSV-2), Epstein-Barr Virus (EBV, HHV-4), Varicella Zoster Virus (VZV), Human Herpes Virus 6 (HHV-6), Human Herpes Virus 7 (HHV-7), or Kaposi's Sarcoma-Associated Herpesvirus (KSHV; HHV-8). In an embodiment, the Herpesvirus infection is HSV infection, in a further embodiment HSV-1 infection.

In an embodiment, the above-mentioned subject is an animal, such as a mammal (e.g., cow, pig, horse, dog, cat, duck, primate). In a further embodiment, the subject is a human.

MODE(S) FOR CARRYING OUT THE INVENTION

The present invention is illustrated in further details by the following non-limiting examples.

Example 1

Material and Methods

Cell Culture and Viruses.

Vero cells (African green monkey kidney fibroblasts) were propagated in Dulbecco's Modified Eagle Medium (DMEM) (Invitrogen) supplemented with 5% newborn calf serum (NCS) (Invitrogen), 50 U/ml of penicillin and 50 µg/ml of streptomycin (Invitrogen). HeLa cells were cultured in DMEM with 8% foetal bovine serum (FBS) (Invitrogen) with the same concentration of antibiotics. Infections were carried out in DMEM with 2% NCS and the same concentration antibiotics. The HSV-1 strain KOS and UL24X (Jacobson, J. G., et al. 1998. *Virology* 242:161-9) were originally provided by D. M. Coen. The strain vHA-UL24, which was constructed in a KOS background, has been described previously (Lymberopoulos, M. H., and A. Pearson. 2007. *Virology* 363: 397-409).

Human Foreskin Fibroblast (HFF) were obtained from the American Type Culture Collection (ATCC). Cells were maintained in Dulbecco's modified Eagle's medium (DMEM) supplemented with 10% (v/v) foetal bovine serum and antibiotics (50 U $ml^{-1}$ penicillin and 50 µg $ml^{-1}$ streptomycin). Cells were maintained in a humidified incubator with 5% $CO_2$ at 37° C. unless indicated otherwise.

Preparation of Whole Cell Extracts from Infected Cells.

$1.5 \times 10^7$ Vero or HeLa cells were seeded in T175 flasks, incubated overnight and then infected with the indicated virus at an MOI of 10 in DMEM containing 2% NCS. Flasks were gently shaken every 15 minutes for one hour, then the media was removed and replaced with DMEM containing 5% NCS. At 18 hpi, the cells were washed once with Phosphate Buffered Saline (PBS) and lysed on ice using 1 ml per flask of either RIPA lysis buffer (500 mM NaCl, 1% Triton™ X-100, 0.5% deoxycholic acid, 0.1% SDS, 50 mM Tris pH 8.0 and one tablet of complete protease inhibitor (Roche)) or PA Buffer (120 mM Potassium Acetate, 20 mM Tris pH 7.5, 5 mM EDTA, 10% Glycerol, 0.1% Triton™ X-100 and one tablet of protease inhibitor) (Jarvis, M. A., and J. A. Nelson. 2002. *Curr Opin Microbio*15:403-7) for 15 minutes. Extracts for glycerol gradients were prepared in PA buffer containing 5% glycerol (v/v). Lysed cells were scraped and cellular debris pelleted by centrifugation at 13 000 rpm for 30 minutes at 4° C. in a microcentrifuge. Supernatants were carefully removed and transferred to pre-chilled Eppendorf™ tubes, and stored at −80° C.

Protein Fractionation by Glycerol Gradient Sedimentation.

Glycerol solutions of 8% and 25% were prepared in a glycerol gradient buffer (40 mM potassium phosphate, 1.5 mM $MgCl_2$, 0.2 mM EDTA and 0.05% Triton™ X-100, pH 7.4). Using a gradient mixer, 12 ml continuous gradients were poured in a 14×89 mm thin wall ultracentrifuge tubes (Beckman). Whole cell extracts were layered on top of the gradient, and tubes were centrifuged at 150 000×g in a SW41Ti rotor for 18 hours in a Beckman-Coulter Optima™ L-100K ultracentrifuge. Fractions of 750 µl were collected dropwise.

Immunoprecipitations, Sodium Dodecyl Sulphate-Polyacrylamide Gel Electrophoresis, and Western Blotting.

Whole cell extracts were pre-cleared using 50 µl of Protein G beads (Roche) for 1 hour on an inverter at 4° C. Immunoprecipitation (IP) of HA-UL24 was performed using 50 µl of anti-HA affinity matrix (Roche) for 3 hours at 4° C. on an inverter. Tubes were then centrifuged for 5 minutes at 6 000 rpm at 4° C. using a microcentrifuge, the supernatants were removed, and the beads were washed three times with 1 ml of PA buffer. Washes were performed for 15 min at 4° C. on an inverter. After the final wash, beads were resuspended in 150 µl of 6× protein loading dye (37.5% Glycerol, 3.75% Sodium dodecyl sulphate (SDS), 0.05% Bromophenol Blue, 0.5 M Tris pH 6.8, 20% β-mercaptoethanol) and boiled for 1 minute. Proteins were resolved by SDS-polyacrylamide gel electrophoresis (SDS-PAGE). For silver staining of gels, the ProteoSilver™ plus kit (Sigma) was used according to the manufacturer's instructions. For Western blotting, proteins were transferred to a polyvinylidene fluoride (PVDF) membrane (Immobilon-P™, Millipore), and analyzed by Western blotting using a monoclonal antibody directed against HA (Covance) or a rabbit polyclonal antibody against NM2a (Abcam), and a horseradish peroxidase conjugated secondary antibody directed against mouse (Calbiochem) or rabbit (Bethly). Detection was by enhanced chemiluminescence using ECL™ plus reagents (GE-Amersham) according to the manufacturer's instructions.

Indirect Immunofluorescence Experiments.

Transfections were performed using the vector pLB-HA-UL24 (Bertrand, L., and A. Pearson. 2008. *J Gen Virol* 89:1142-51) and FuGENE™ 6 transfection reagent (Roche) according to the manufacturer's instructions. HeLa cells were seeded at a confluence of $1 \times 10^5$ cells per well in a 24-well plate into which sterile coverslips had been placed. The next day, the plasmid and reagent were incubated for 15 minutes in DMEM media, and added to HeLa cells. After 5 hours, the cells were washed and then incubated for a further 48 hours prior to processing for immunofluorescence (IF). For analysis of infected cells, HeLa or Vero cells were seeded at $1 \times 10^5$ cells per well and grown overnight. The next day, cells were infected at an MOI of 10, shaken every 15 minutes for one hour, then the media was removed and replaced with DMEM containing 5% NCS. At the indicated time, the transfected or infected cells were washed in PBS and fixed for ten minutes using a 2% paraformaldehyde solution prepared in PBS. Cells were then washed with PBS, and the coverslips processed for IF as described previously (Bertrand, L., and A. Pearson. 2008. *J Gen Virol* 89:1142-51). Rat anti-HA (Roche), rabbit anti-NM2a (Abcam), mouse anti-gB (Abcam), mouse anti-gD (Abcam) and mouse anti-gL (Novotny, M. J., et al. 1996. *Virology* 221:1-13) primary antibodies were used at dilutions of 1/250, 1/250, 1/200, 1/200 and 1/100 respectively. The goat ALEXA™-coupled secondary antibodies against rat, rabbit and mouse (Invitrogen) were used at a dilution of 1/1000. The nuclear stain DRAQ5™ (Biostatus) was used at a concentration of 1/500 and was included with the secondary antibody solution. After immunostaining, the cells were washed once in PBS, and the coverslips were mounted on glass slides using Prolong™ Gold Anti-Fade reagent (Invitrogen). Confocal microscopy was carried out at the INRS-Institut Armand-Frappier imaging facility using a Bio-Rad Radiance™ 2000 confocal with an argon-krypton laser at 488 and 568 nm (diode 638 nm) mounted onto a Nikon™ E800 microscope using a 100× objective and a 1.6× software magnification in Lasersharp™ software (Bio-Rad). Images were prepared using Adobe Photoshop™ CS5.

Quantification of Co-Localization (Manders Coefficient).

To quantitate the degree of co-localization of gB, gD and gL staining (green) with NM2a staining (red), the Manders overlap coefficient (Manders, E. M. M., et al. 1993. *Journal of Microscopy* 169:375-382 was calculated using the JACoP tool (Segal, A. L., et al. 1974. *J Dent Res* 53:797-803). The different images were first background-subtracted; the program allowed adjusting thresholds of the two images to define pixels that were positive in both channels prior to analysis. Using the JACoP plug-in, the rate of co-localization was determined on a pixel-to-pixel basis by scatter. The Manders overlap coefficient varies from 0 to 1, with 0 corresponding to non-overlapping images and 1 corresponding to 100% co-localization between the two images. At least 10 fields of view were analyzed for each condition, which represent at least 32 cells per condition. Statistical analysis of the significance between datasets was undertaken using the t test with a value of P<0.05 for significance.

Quantification of Co-Localization (Pearson's Coefficient)

Co-localization of staining in confocal microscopy experiments was quantified using the ImageJ: JACoP plugin (National Institutes of Health) (Bolte, S. & Cordelieres, F. P. (2006). *J Microsc* 224, 213-232) to calculate the Pearson's correlation coefficients, which describe the correlation of the intensity distribution between green and red channels of the analysed image. The coefficient can vary between −1 and 1, with 1 representing perfect co-localization, zero representing no co-localization, and negative values indicating inverse correlations. We used the JACoP software to determine the degree of co-localization between gB or gD with marker-stained F-actin (phalloidin) by means of the Pearson's coefficient (means±SEM). At least 50 fields of view were analysed for each condition. Statistical analysis of significance between datasets was undertaken using at test with a value of p<0.05 for significance.

Antibodies.

The primary antibodies used were as follows: Mouse monoclonal anti-GM130 (BD Bioscience), rabbit polyclonal anti-Mannosidase II (Abcam), mouse monoclonal anti-golgin 97 (Invitrogen), mouse monoclonal anti-gB (Abcam), and mouse monoclonal anti-gD (Abcam). For F-actin staining, Alexa Fluor™ 488-coupled phalloidin (Invitrogen) was used according to the manufacturer's instructions. Secondary antibodies were as follows: goat anti-mouse IgG Alexa Fluor™ 488, goat anti-mouse IgG Alexa Fluor™ 568, goat anti-Rabbit IgG Alexa Fluor™ 488 (Invitrogen).

Immunostaining and Confocal Microscopy $1 \times 10^5$ HFFs were seeded onto glass coverslips in 24-well plates. The following day, cells were either mock-infected or infected at an MOI of 10 with KOS or UL24X. At the indicated hpi, cells were fixed in 2% (v/v) paraformaldehyde for 10 min, permeabilised by incubation for 10 min in 0.1% Triton X-100 diluted in phosphate buffered saline (PBS), washed twice with PBS, and then blocked with NATS (20% (v/v) NCS and 0.5% (v/v) Tween™ 20 in PBS) for 30 min. Incubation with the appropriate primary antibody was carried out in a humidified chamber at 37° C. for 1 h. Cells were washed 4×5 min in PBS, and then incubated with the secondary antibody mixed with a 1/250 dilution of the nuclear stain DRAQ5™ (Biostatus limited) for 1 h at 37° C. in a humidified chamber. After washing four times in PBS, coverslips were mounted on microscope slides using ProlongGold™ antifade reagent (Invitrogen). Slides were visualized using the BioRad Radiance™ 2000 confocal with an argon-krypton laser at 488 and 568 nm (diode 638 nm) mounted onto a Nikon™ E800 microscope. Images were assembled using Adobe Photoshop™. Confocal microscopy was carried out at the INRS-Institut Armand-Frappier imaging facility. For the immunofluorescence figures shown, each experiment was repeated a minimum of three times, and the fields shown are representative of the major staining patterns observed under each set of conditions.

Example 2

UL24 of HSV-1 is Present in High Molecular Weight Protein Complexes

To determine if UL24 had interacting partners, extracts from HSV-1-infected HeLa cells were fractionated on glycerol gradients to see if a portion of UL24 sedimented at a higher molecular weight then that corresponding to its predicted molecular weight, which would indicate an association with other proteins. Cells were infected for 18 hours with the virus vHA-UL24 (Lymberopoulos, M. H., and A. Pearson. 2007. *Virology* 363:397-409), which expresses UL24 with an N-terminal hemagglutinin (HA) affinity tag. This virus replicates like the wild-type parental virus KOS, and does not form syncytial plaques. Whole cell extracts were applied to a 8%-25% continuous glycerol gradient. Following centrifugation, gradients were separated in 16 fractions. Samples of each fraction were resolved by SDS-PAGE, and were analyzed by Western blotting using an antibody directed against HA (FIG. 1A). As a control for the efficacy of the gradient fractionation, fractions from a gradient run in parallel where we stained the proteins with silver were also analyzed (FIG. 1B); the expected general pattern of sedimentation of proteins according to molecular weight was obtained. To assign the molecular weights corresponding to the different fractions, a native molecular weight marker was fractionated in parallel. Surprisingly, the fractions in which HA-UL24 was detected (6-9) corresponded to a molecular weight of 242 to 720 kDa. In contrast, had UL24 fractionated corresponding to its predicted molecular weight, it would have been detected in fractions 13-14. These results demonstrate that UL24 is present in one or multiple high molecular weight complexes in HSV-1-infected HeLa cells.

Example 3

NM2a Co-Precipitates with HA-UL24

Figure 2A:
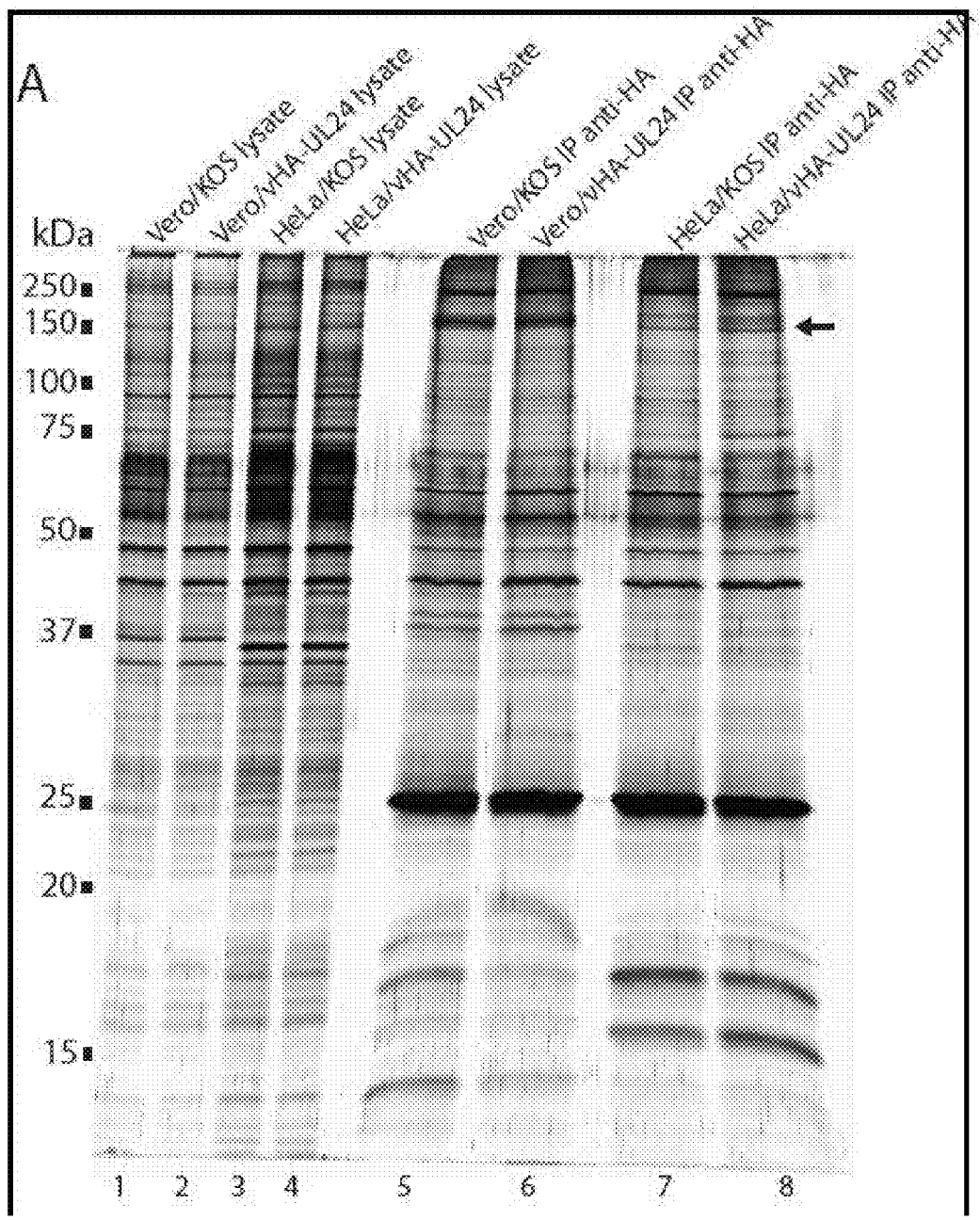

To identify the proteins present in the UL24 complex, HA-UL24 was immunoprecipitated (IP) using an anti-HA matrix. Whole cell extracts prepared from either KOS- or vHA-UL24-infected cells, were used for immunoprecipitation using an antibody directed against HA. The precipitated proteins were separated by SDS-PAGE, and visualized by staining with silver (FIG. 2A). A band, between the 150 and 250 kDa protein markers, that was specific for the HA co-IP performed on extracts from HeLa cells infected with vHA-UL24 was observed. This band was not detected when extracts of cells infected with KOS were used. It was not possible to discern if a similar band was present in the anti-HA IP performed on infected Vero cell extracts due to the presence of non-specific bands in the same area on the gel. The specific band was excised from the gel and subjected to tryptic digest, and the resulting peptides were identified by mass spectrometry. The results indicated the presence of the protein Non-muscle Myosin Type II a (NM2a). This hit had a score of 1652, and 26 unique peptides were identified (FIG. 2B). The glycerol gradient fractionation profile of NM2a in extracts of HSV-1-infected cells was tested for the presence of NM2a. It was found that NM2a was present in the peak fractions for UL24 (FIG. 2C). A second peak for NM2a was also detected at the bottom of the gradient.

Figure 3:
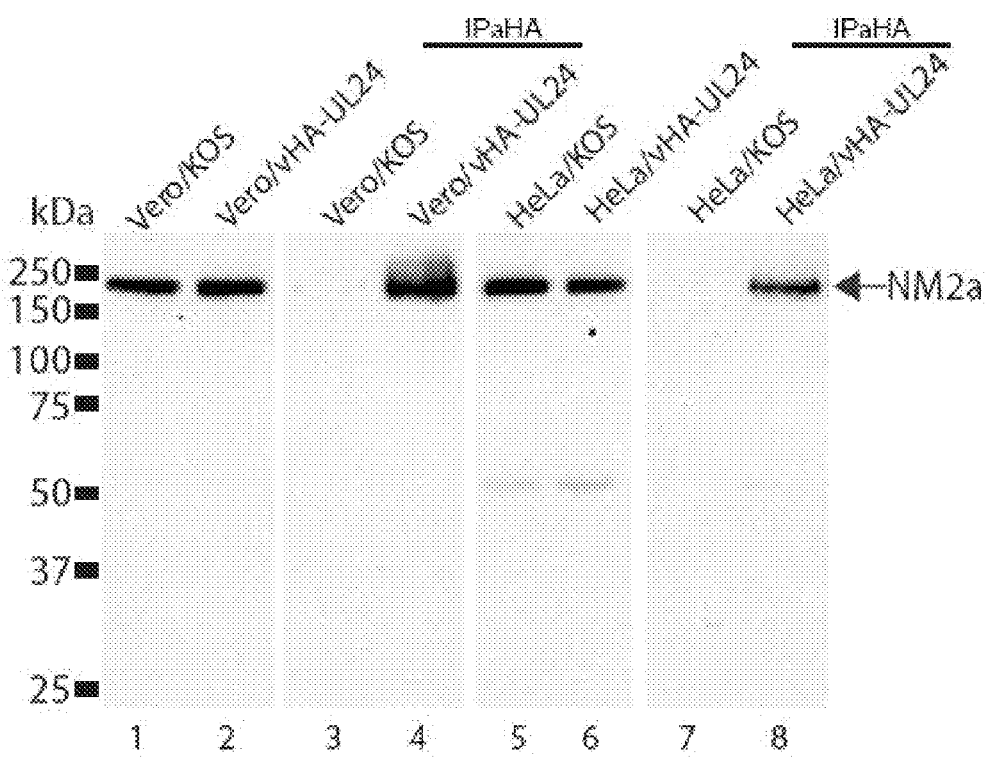
FIG. 3 shows the co-immunoprecipitation of NM2a with HA-UL24. Immunoprecipitation directed against HA using extracts from Vero and HeLa cells infected with either KOS or vHA-UL24 were carried out, followed by a Western blot to detect NM2a. Lanes 1, 2, 5 and 6 correspond to 1% of the indicated extract input. Lanes 3, 4 and 7, 8 are the immunoprecipitates obtained for each condition. The arrow on the right indicates the position of NM2a. The position of the molecular weight markers are indicated to the left of the figure.

To confirm the interaction of UL24 with NM2a, we performed a co-IP Western blot experiment. NM2a co-precipitated with HA-UL24 using HeLa cell extracts, and also using Vero cell lysates (FIG. 3). These interactions were specific, since they were not observed when extracts from cells infected with KOS were used.

Example 4

Partial Co-Localization of UL24 and NM2a

Figure 4A:
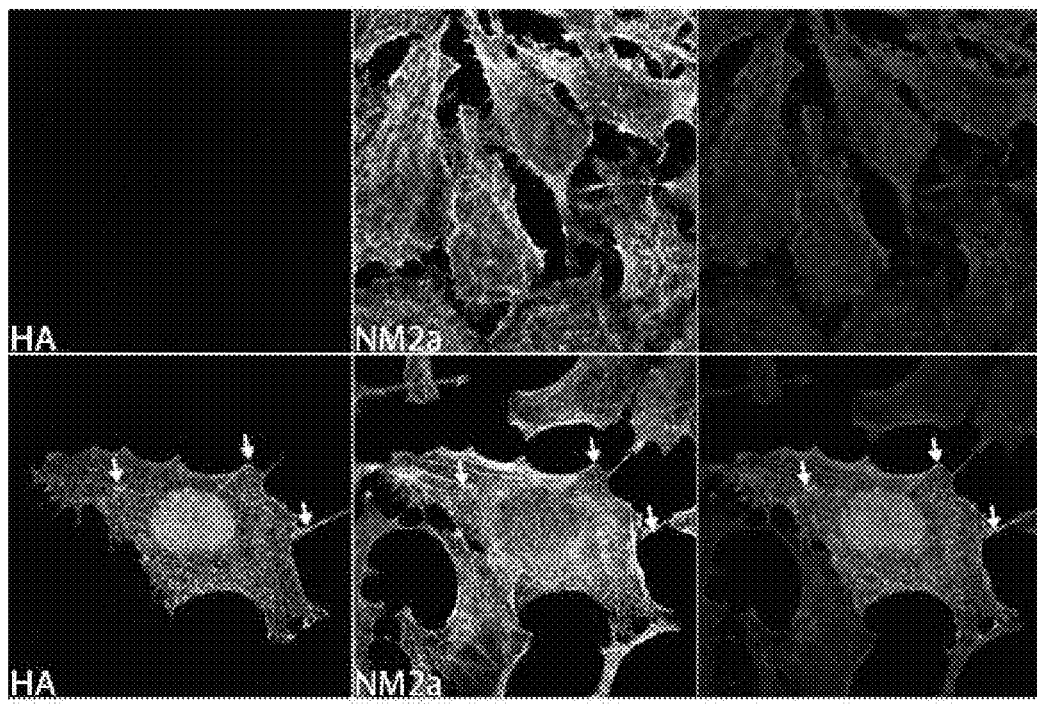

To identify cellular compartments where UL24 and NM2a associate, the localization of HA-UL24 and NM2a in HeLa cells that transiently expressed HA-UL24 was studied (FIG. 4A). HeLa cells were co-immunostained for HA and NM2a. No signal was detected using an antibody directed against HA in mock-transfected cells (FIG. 4A, top panel). There is no significant difference in the subcellular distribution of NM2a in the presence or absence of UL24; however, several sites with overlap of staining for NM2a and HA-UL24 were detected, especially near or at the cell membrane (FIG. 4A).

Figure 4B:
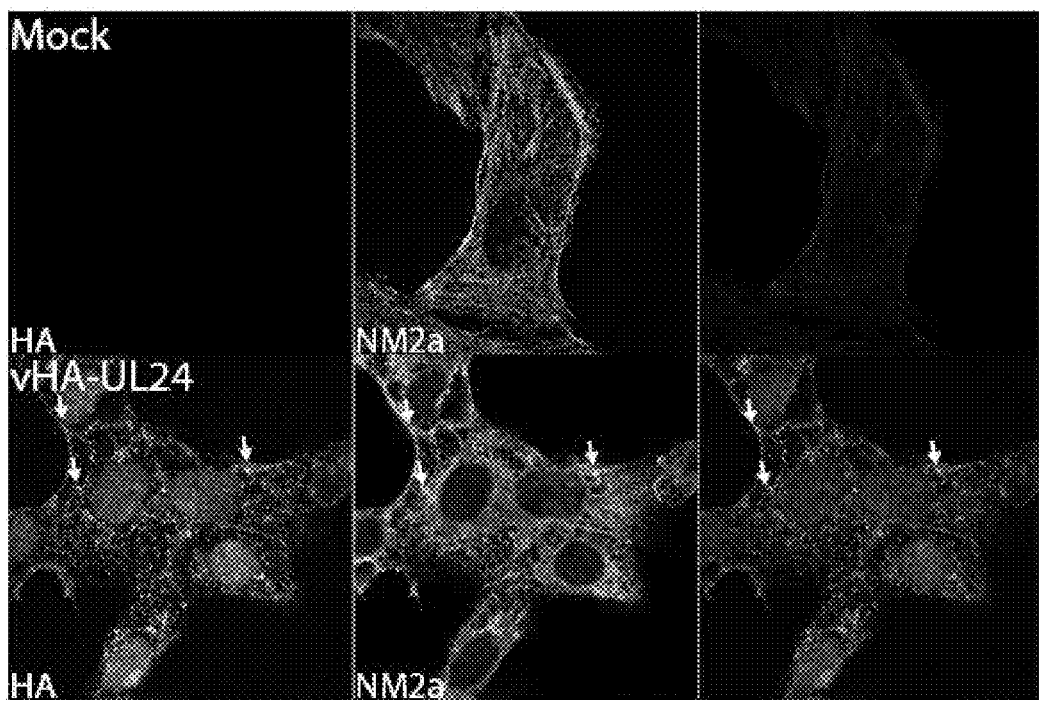

The localization of UL24 with respect to NM2a in Vero cells infected with vHA-UL24 was next investigated. Upon infection, a change in staining pattern for NM2a was observed, from the periphery of the cell to a more perinuclear region. A similar change was observed in cells infected with wild-type virus KOS or a UL24-deficient virus, UL24X. In KOS-infected cells, a partial co-localization of NM2a and HA-UL24 was detected, which appeared to be more pronounced at membranes and in the perinuclear region (FIG. 4B, bottom panel).

Example 5

Reduced Association of NM2a and HSV-1 gB in the Absence of UL24

Figure 5A:
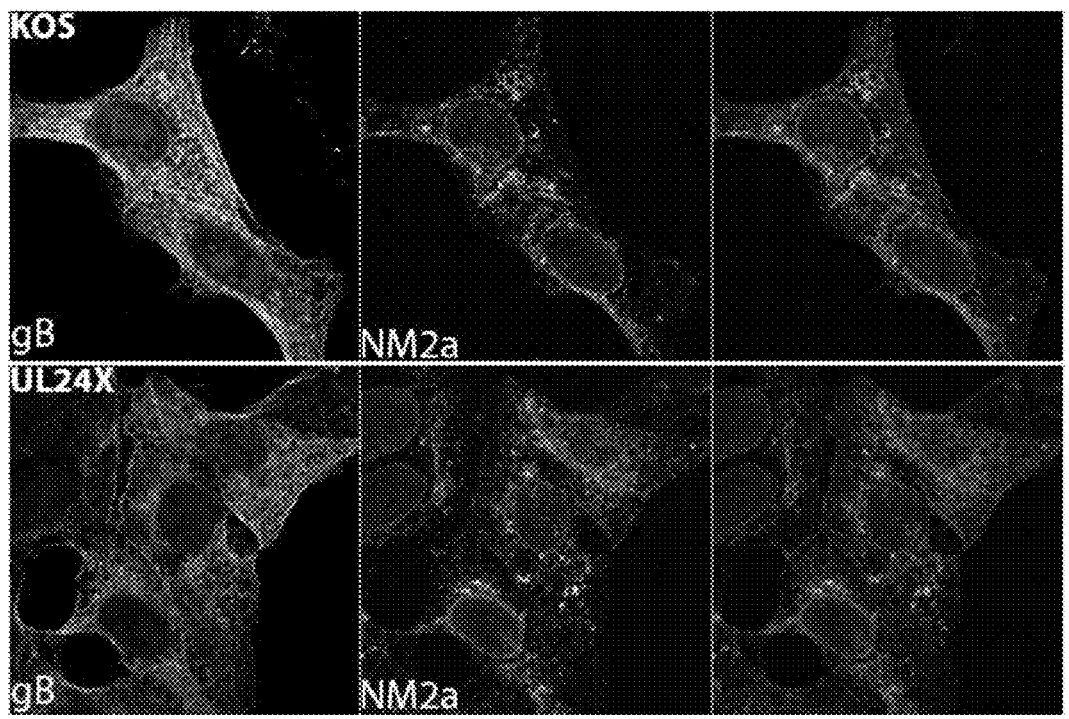
FIGS. 5A to 5F show the reduction of the co-localization of NM2a and gB in the absence of UL24. Vero cells were either infected with KOS or UL24X for 9 hours, and then co-immunostained for NM2a and for gB, gD or gL.
Figure 5B:
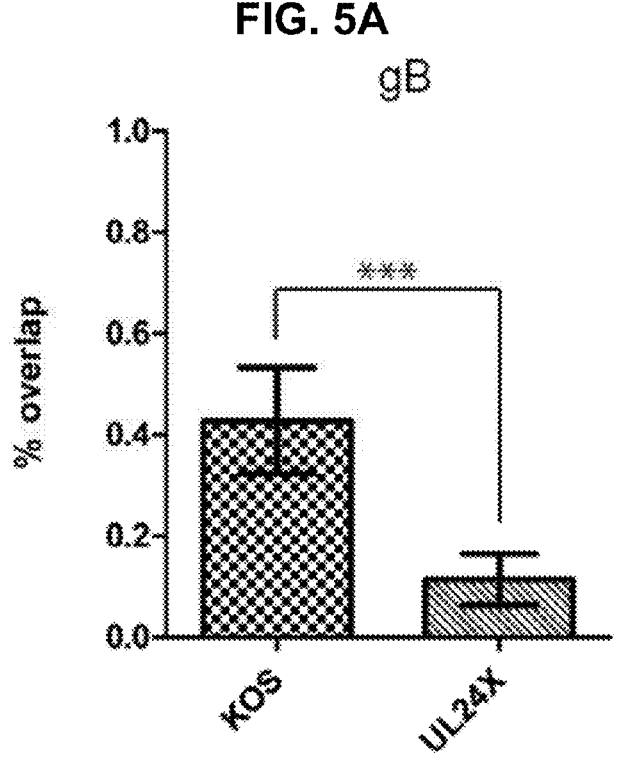
Figure 5C:
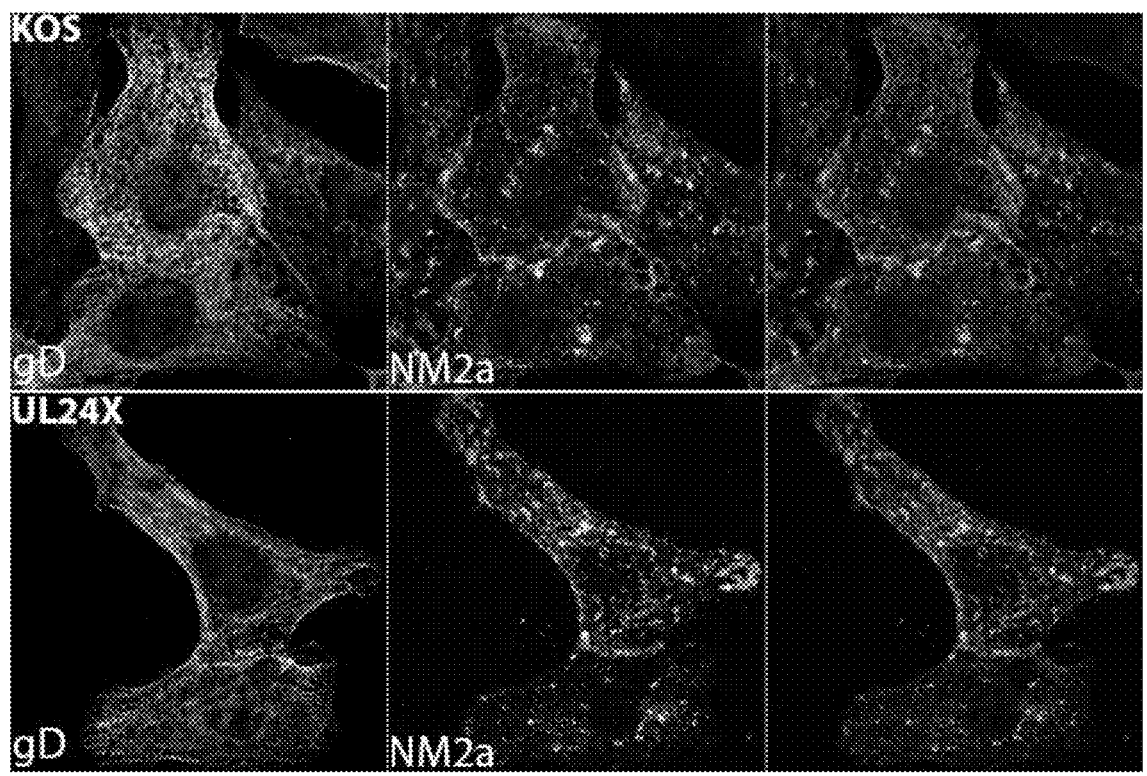
Figure 5D:
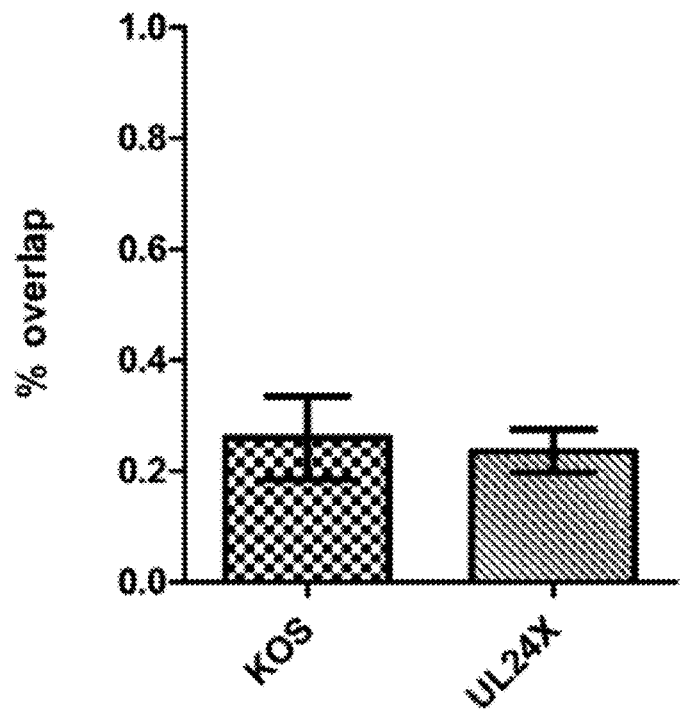
Figure 5E:
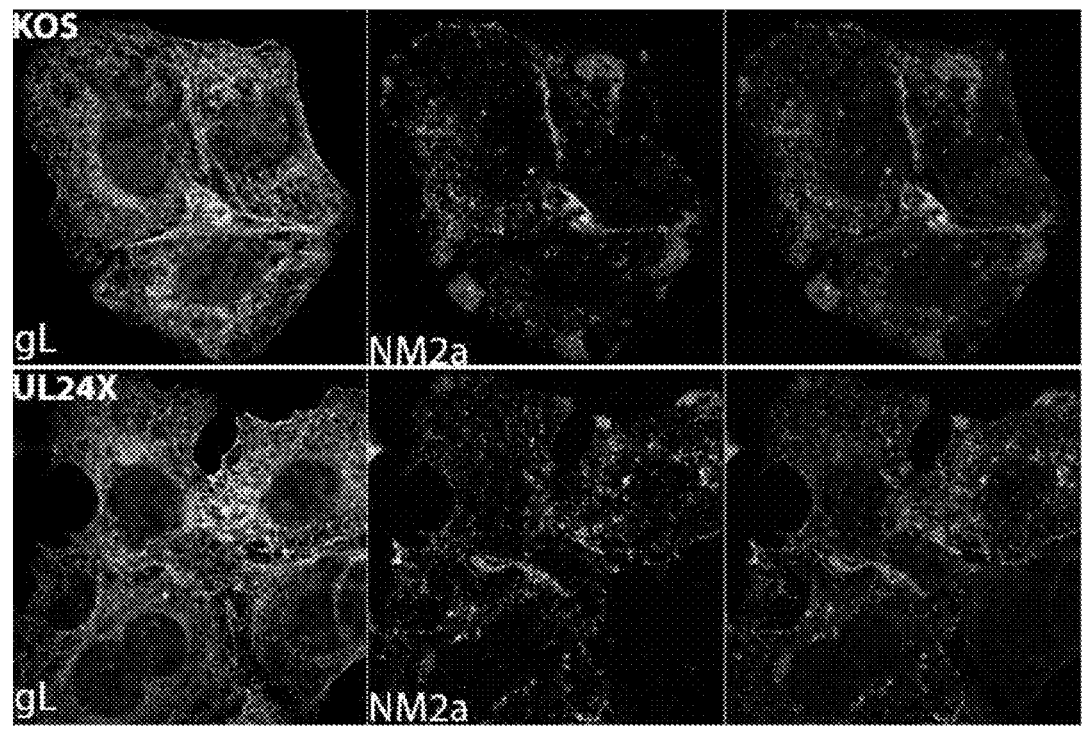
Figure 5F:
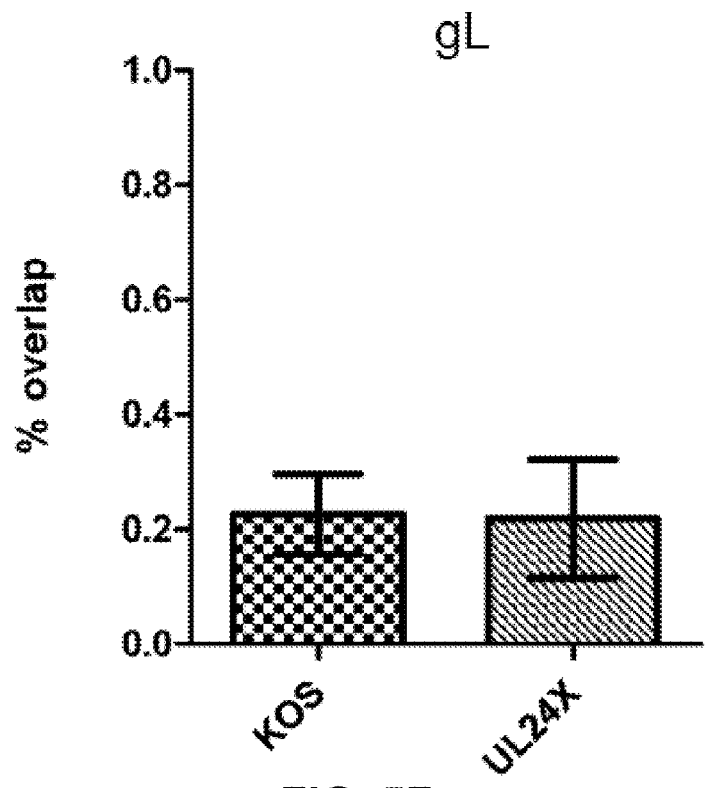

Because a direct interaction between NM2a and gB has been demonstrated (Arii, J., et al., Nature 467:859-62), and in light of the interaction identified herein between UL24 and NM2a, it was assessed whether UL24 affects the interaction of gB and NM2a during infection. Vero cells were infected with the wild-type virus KOS or the UL24-deficient virus, UL24X (Jacobson, J. G., et al. J Virol 63:1839-43), and processed for IF at 9 hpi. Interestingly, in the absence of UL24, the partial co-localization of gB and NM2A seen in KOS-infected cells (FIG. 5A, top panel), appeared to be reduced (FIG. 5A, bottom panel). The change in the co-localization between NM2a and two other viral glycoproteins, gD and gL, was also assessed. Although some degree of overlapping staining with NM2A was detected, it did not appear that there was an appreciable change in co-localization of either of these glycoproteins with NM2a when cells were infected with UL24X as compared to KOS (FIGS. 5C and E). To further validate these observations, the co-localization in both conditions was quantified by calculating the Manders coefficient. FIG. 5B shows that there is a significant reduction of the Manders overlap coefficients between NM2a and gB in the absence of UL24 (24%) compared to an infection with wild-type virus (42%) ($p<0.0001$); however, such a reduction was not observed for gD and gL (FIGS. 5D and F).

Example 6

Impact of UL24 on the ER and Golgi Apparatus in HSV-1-Infected HFF Cells

In several established cell lines such as Vero and Hep-2 cells, HSV-1 infection has been shown to induce the fragmentation of the Golgi apparatus (Avitabile, E. et al. (1995). *J Virol* 69, 7472-7482; Campadelli-Fiume, G., et al. (1993). *J Gen Virol* 74, 2257-2262; Ward, P. et al. (1998). *Virology* 241, 189-199). This modification may be related to the role of the Golgi apparatus in secondary envelopment when virions acquire their final envelope by budding into glycoprotein-enriched vacuoles derived from trans-Golgi network (Harley, C. A., et al. (2001). *J Virol* 75, 1236-1251; Turcotte, S., et al. (2005). *J Virol* 79, 8847-8860). It has been previously shown that the viral protein UL24 exhibits perinuclear localisation in HSV-1-infected Vero cells at late times in infection (Lymberopoulos, M. H. & Pearson, A. (2007). *Virology* 363, 397-409). Furthermore, cytoplasmic UL24 co-localizes with the trans-Golgi marker Golgin 97 upon transient expression in Cos-7 cells (Bertrand & Pearson, 2008, supra). Because of the association of viral glycoproteins with the ER and the Golgi apparatus, the possibility that UL24 affects the localization of viral glycoproteins indirectly through an effect on the organisation of these organelles was investigated. For these studies, HFF cells were chosen because they are not immortalized, and thus might better represent the host cell during a natural infection than immortalized cells. Infection of HFFs with a UL24-null strain induces the formation of syncytial plaques.

Figure 8:
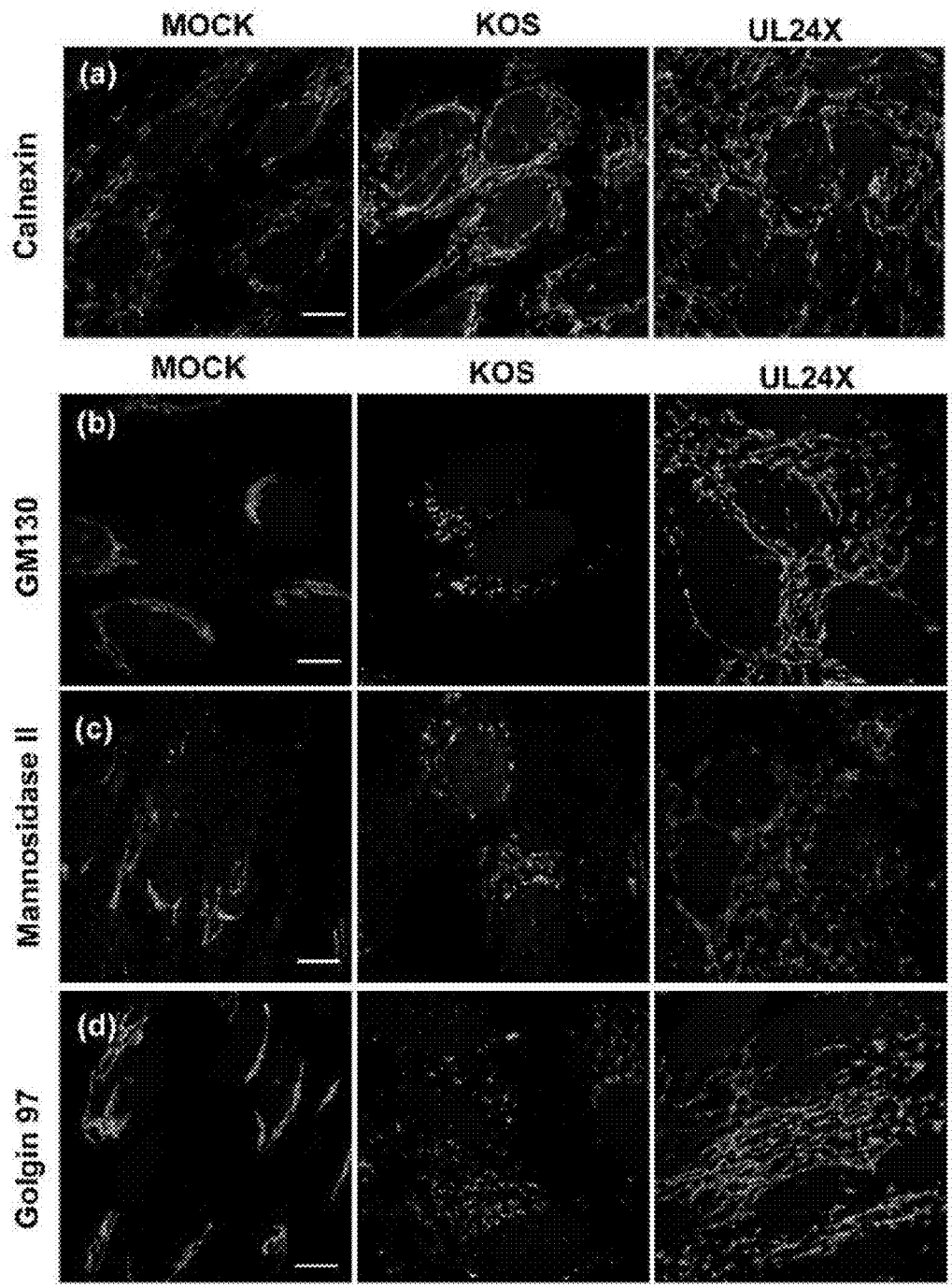
FIG. 8 shows the impact of UL24 on ER and Golgi structures during HSV-1 infection. Shown are confocal images of HFF cells either mock-infected (left-hand panels) or infected at an MOI of 10 with either KOS (middle panels) or UL24X (right-hand panels) for 18 hours. Cells were processed for immunofluorescence using antibodies directed against the following ER and Golgi markers: (a) calnexin (ER), (b) GM130 (cis-Golgi), (c) mannosidase II (medial-Golgi), and (d) Golgin 97 (trans-Golgi). Secondary antibodies used were conjugated to Alexa™ 488. Nuclei were stained with DRAQ5™ (blue). Scale bars represent 10 microns.

In order to determine the impact of UL24 on the structure of the ER network, HFFs were either mock-infected or infected at an MOI of 10 for 18 h with KOS or the UL24-null virus UL24X. Cells were fixed and then immunostained for the ER protein calnexin (FIG. 8A). It was found that HSV-1 infection had little effect on the structure of the ER as compared to mock-infected cells (left-hand panel). While the pattern was a bit less extended in the KOS-infected cells (middle panel), this slight modification was likely an indirect effect of the rounding up of the infected cells. Furthermore, similar staining patterns were obtained for HFFs infected with KOS and with UL24X (right-hand panel). Thus, it may be concluded that UL24 was not involved in the minor changes observed in the organisation of the ER seen during infection.

The morphology of the different parts of the Golgi apparatus in cells infected with the wild-type strain and UL24X was next compared. Cells were fixed and immunostained using antibodies directed against markers for the cis, medial and trans-Golgi, namely GM130 (FIG. 8B), Mannosidase II (FIG. 8C) and golgin 97 (FIG. 8D) respectively. In mock-infected cells, the expected perinuclear staining for each of the three Golgi markers was observed (FIG. 8B-D, left-hand panels). In contrast, the staining for each of these markers was drastically altered in cells infected with KOS, reflecting the previous reports of HSV-1 induced Golgi fragmentation (FIG. 8B-D, middle panels). More specifically, the staining for each of the Golgi markers was fragmented and dispersed throughout the cytoplasm in KOS-infected cells. In contrast, in the absence of UL24, a different altered Golgi structure was observed. The majority of HFF cells infected with UL24X exhibited an extensive Golgi-staining pattern whereby large networks of reticulated Golgi structures extended throughout the syncytium encompassing several nuclei (FIG. 8B-D, right-hand panels).

Example 7

Figure 9A:
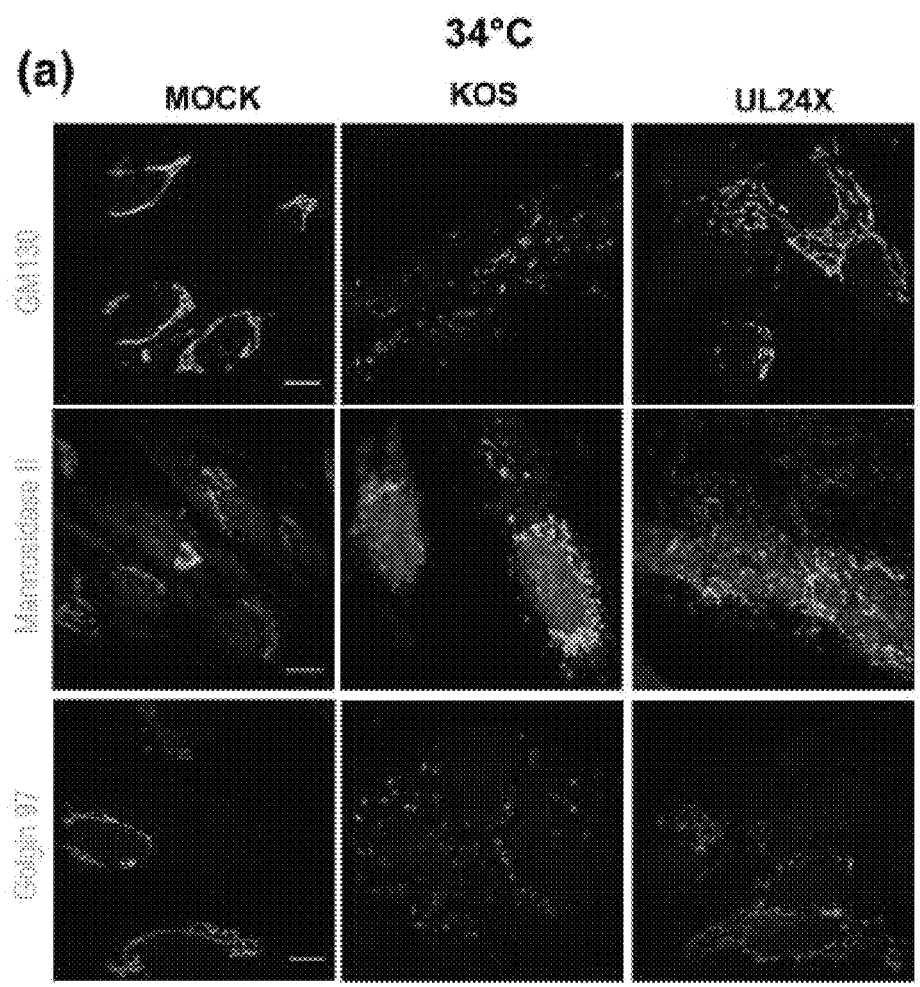
FIGS. 9A to 9D shows the fragmentation of extended Golgi networks, induced by infection with a UL24 mutant virus, at 39° C. HFF cells were mock-infected (left-hand panels) or infected with either KOS (middle panels) or UL24X (right-hand panels) at an MOI of 10 for 18 h. Infected cells were maintained at the indicated temperature.
Figure 9B:
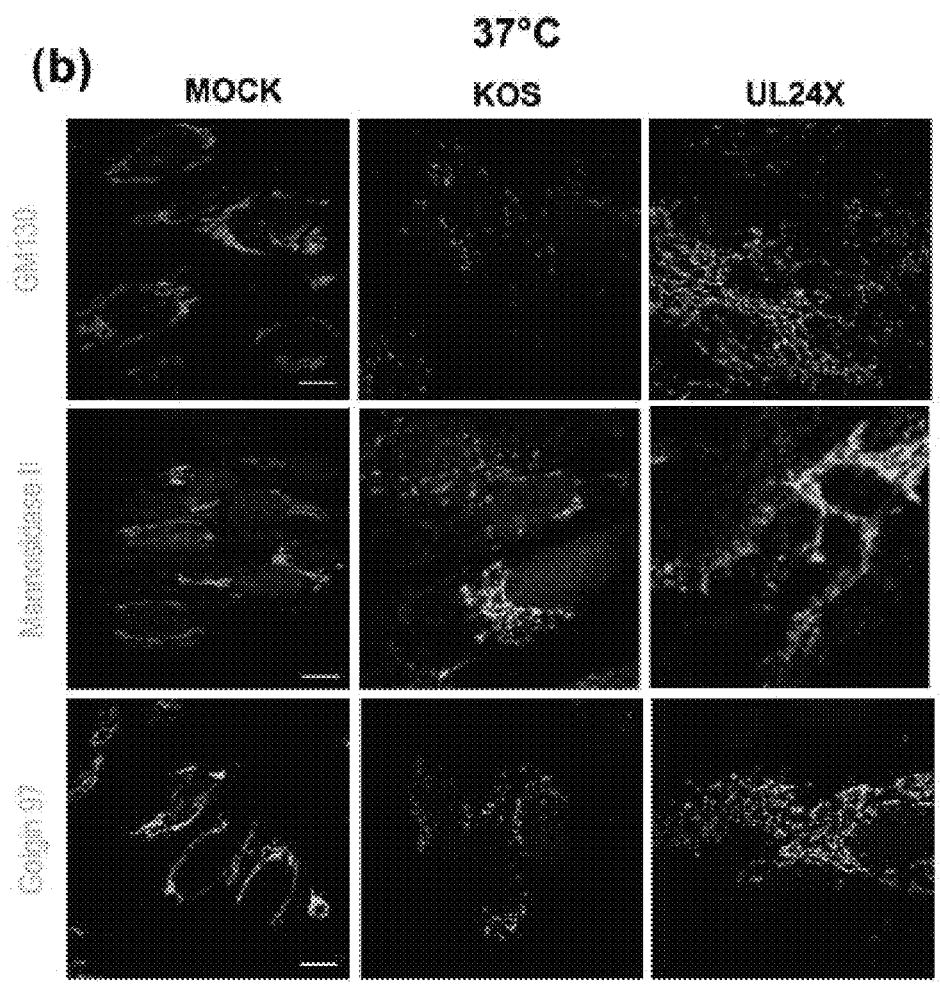
Figure 9C:
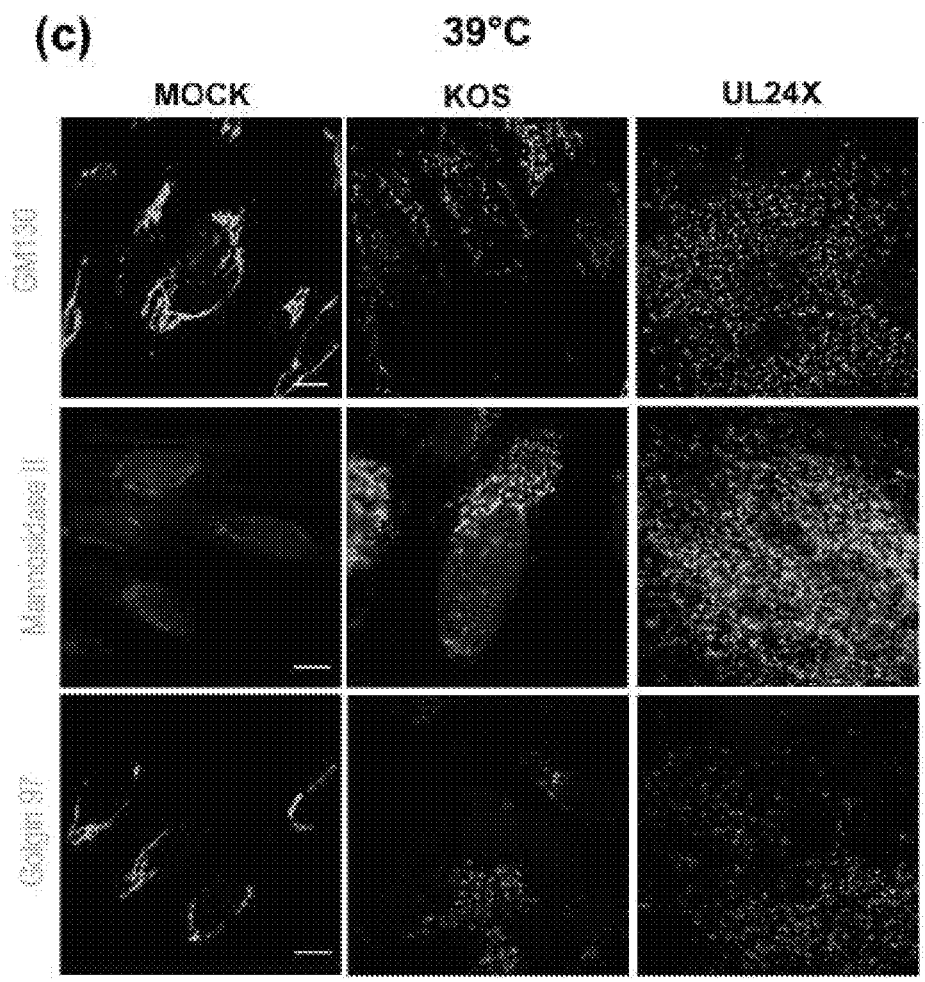
Figure 9D:
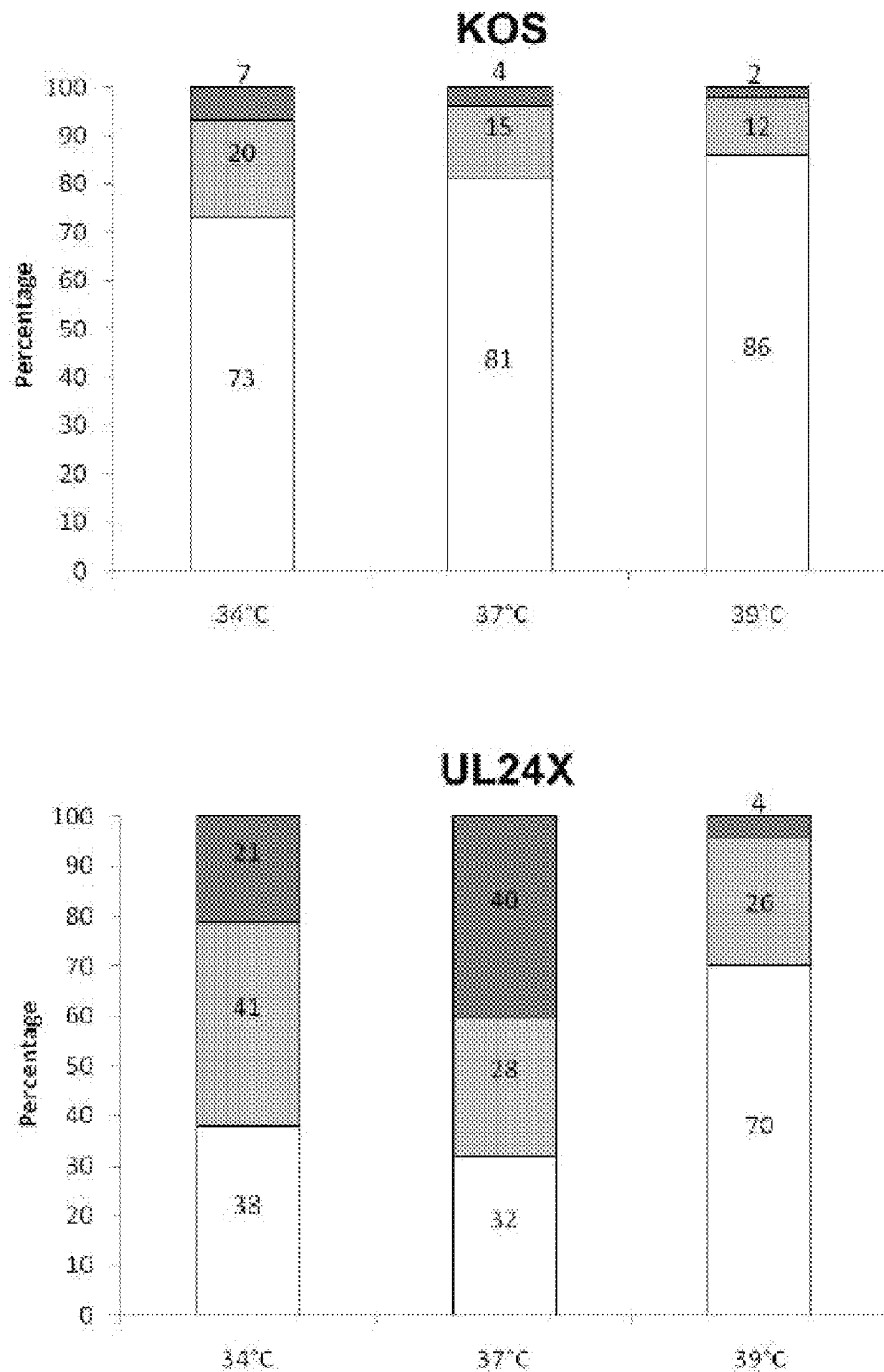

UL24 is Dispensable for Disruption of Golgi Compartments in Syncytia at High Temperatures The UL24 syncytial phenotype is more penetrant at 39° C. than at 37° C. Furthermore, the UL24X strain forms small, non-syncytial plaques at 34° C. (Jacobson, J. G., et al. (1989). *J Virol* 63, 1839-1843). It was tested whether the extensive Golgi network that was formed in UL24X-infected cells at 37° C. became more prominent under conditions where the UL24 phenotype was more evident. The distribution of Golgi markers in KOS- and UL24X-infected HFF cells at 34, 37 and 39° C. was compared 18 hours post-infection (hpi) (FIGS. 9A, B, and C respectively). At 34° C., mock-infected HFF cells exhibited the same staining pattern as that observed in mock-infected cells maintained at 37° C. and 39° C. (FIG. 9A). At 34° C., the fragmentation of the Golgi apparatus in KOS-infected cells appeared less advanced than that typically observed at 37° C. Similarly, at this lower temperature, the network of Golgi staining seen in UL24X-infected cells was less extensive than that seen at 37° C. This difference likely reflects a reduction in viral replication at the lower temperature. A difference in the punctate staining scattered throughout the cytoplasm observed for the different Golgi markers in KOS-infected cells at 37° C. as compared to 39° C. was not detected. Surprisingly, at 39° C., when all plaques formed by UL24X were syncytial, the structured network of Golgi staining seen at 37° C. was lost and rather, extensive fragmentation of the Golgi for each marker tested was observed.

The staining patterns for the cis-Golgi marker GM130 was quantified at the three temperatures tested. Staining patterns were categorized as punctate, intermediate or network, where intermediate meant that a combination of patterns was observed in the same field. The data shown represent the average of three experiments where at least 100 different fields of view were analysed per experimental condition (FIG. 2D). At 34° C., 73% of the fields of view for cells infected with KOS exhibited a punctate Golgi-staining pattern, while values of 20% and 7% were obtained for intermediate and network staining patterns respectively. In contrast, only 38% of the fields of view of UL24X-infected cells exhibited a punctate staining pattern for GM130, while values of 41% and 21% were obtained for intermediate and network patterns respectively. At 37° C. in KOS-infected cells, a slight increase in the amount of punctate staining was seen (81% of fields) along with concomitant small decreases for the other two categories of staining. Analysis of UL24X-infected cells revealed that the network staining pattern was the most prominent at 37° C. (40%), with 32% of the fields of view exhibiting punctate staining and 28% an intermediate pattern. Thus, at both 34 and 37° C., there was less fragmentation of the Golgi apparatus in cells infected with UL24X as compared to KOS, as well as the development of extended Golgi networks. For KOS-infected cells, the relative importance of the different staining patterns was similar at 37 and 39° C. In contrast, for UL24X-infected cells, a major shift was detected at 39° C. At this higher temperature, the distribution of staining patterns resembled that seen with KOS in that 70% of the fields of view exhibited punctate staining, while a network staining pattern was detected in only 4% of fields. Thus, it was found that the extensive webbed network of Golgi staining seen with UL24X did not correlate with the strength of the UL24 syncytial plaque phenotype in infected cells. Rather, at high temperatures, when the syncytial phenotype was more prominent, the pattern of Golgi staining reverted to that observed with the wild-type virus. Thus, the webbed network of Golgi staining seen in UL24X-infected cells at 37° C. was likely an indirect effect of the formation of syncytia, while at 39° C., the increase in temperature drove the fragmentation of the Golgi regardless of the formation of syncytia.

Example 8

Altered Distribution of HSV-1 gB, gD at Late Times in Infection in the Absence of UL24

Figure 10A:
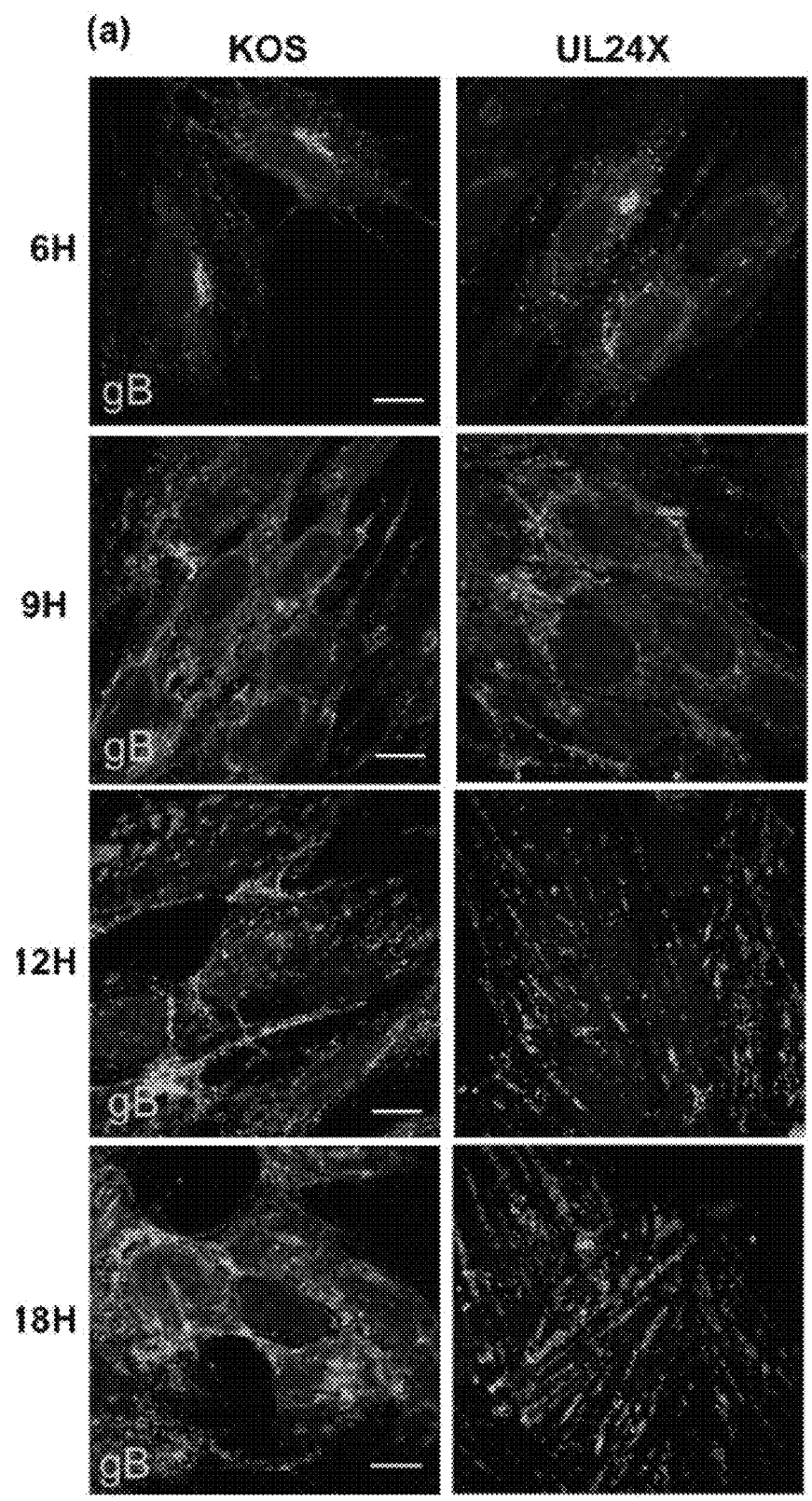
FIGS. 10A and 10B show a time course of gB and gD distribution in KOS- and UL24X-infected HFFs. HFF cells were infected with either KOS (left-hand panels) or UL24X (right-hand panels) at an MOI of 10. Cells were fixed at the indicated times post-infection and processed for immunofluorescence using monoclonal antibodies directed against the indicated viral glycoprotein, (FIG. 10A) gB and (FIG. 10B) gD. Secondary antibodies were conjugated to Alexa™ 488. Nuclei were stained with DRAQ5™ (blue). Scale bars represent 10 microns.
Figure 10B:
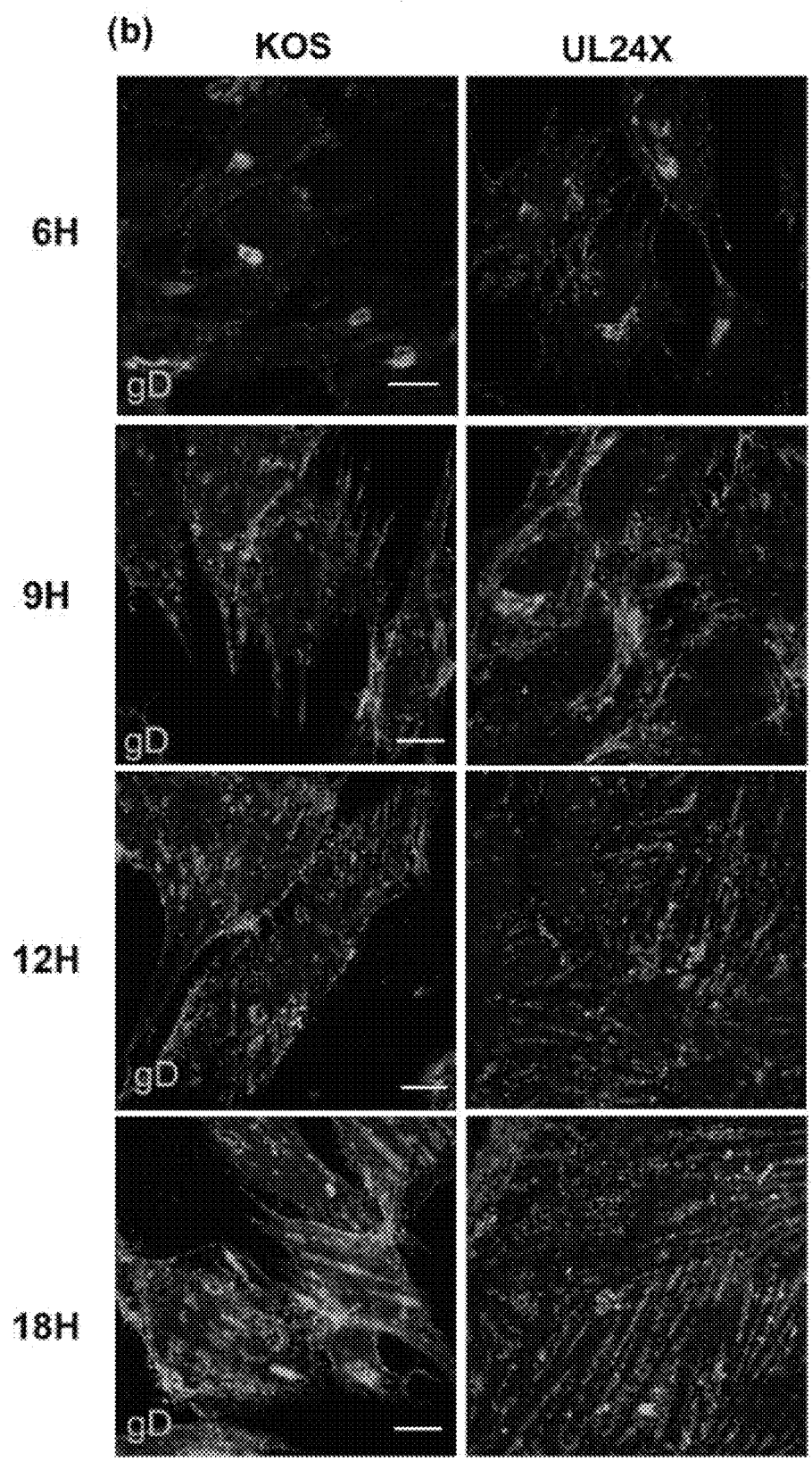

The UL24-associated syncytial phenotype suggests that UL24 is involved in membrane fusion events during infection. It was hypothesized that UL24 has a role in the localization of viral glycoproteins during the latter stages of virion morphogenesis. The cellular localisation of gB and gD at different times post-infection in the presence or absence of UL24 was investigated (FIG. 10). HFF cells were infected in parallel with either KOS or UL24X at an MOI of 10. At 6, 9, 12 and 18 hpi cells were fixed and stored at 4° C. until the end of the time course following which they were immunostained for the indicated glycoproteins. At 6 hpi, for both gB (FIG. 10A) and gD (FIG. 10B) in KOS-infected cells, perinuclear staining corresponding to the Golgi was observed, as described previously (Ali, M. A., et al. (1987). *Proc Natl Acad Sci USA* 84, 5675-5679; Norrild, B. et al. (1983), *Arch Virol* 77, 155-166; Wanas, E., et al. (1999) *J Gen Virol* 80 (Pt 12), 3189-3198). At this early time point, there was no obvious difference in the staining patterns for gB and gD in UL24X-as compared to KOS-infected cells. Similarly, at 9 hpi, although the cytoplasmic staining increased for both gB and gD, there was no obvious difference in cells infected with the wild-type and UL24-null viruses; however, by 12 hpi differences began to emerge. In KOS-infected cells, speckled and blotchy cytoplasmic staining for both gB and gD was observed; however, in UL24X-infected cells, thin, line-shaped structures were primarily detected. This pattern intensified at 18 hpi for both gB and gD in UL24X-infected cells, while increased blotchy cytoplasmic staining was observed in KOS-infected cells. Although these structures sometimes appeared to form thick lines, relatively few thin line structures were detected in the context of the wild-type virus. Similar results were obtained for gH. Thus, UL24 has an impact on the subcellular distribution of viral glycoproteins involved in membrane fusion, particularly at late times in infection.

Example 9

UL24 the Affects Co-Localization of HSV-1 gB and gD with F-Actin

Figure 11A:
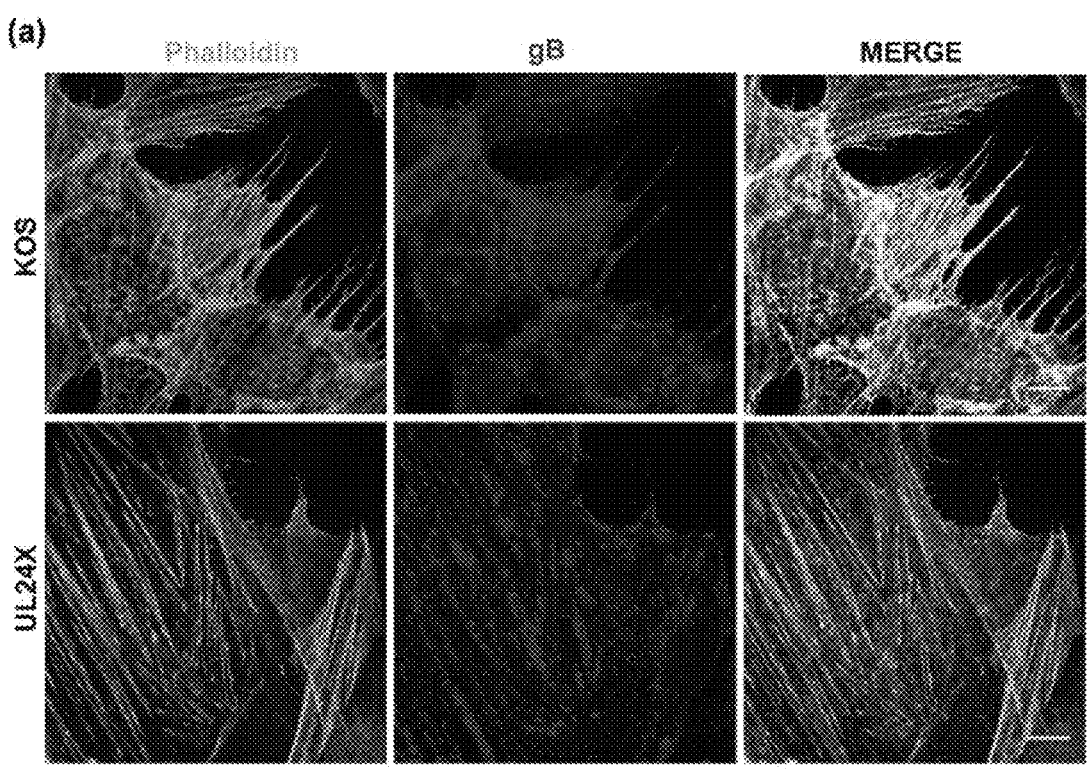
FIGS. 11A and 11B show that UL24 affects the association of gB and gD with F-actin. HFF cells were infected with either KOS or UL24X at an MOI of 10. Cells were fixed at 18 hpi, and co-stained for the indicated viral glycoprotein and F-actin. Immunostaining of (FIG. 11A) gB and (FIG. 11B) gD (left-hand panels) was carried out using the appropriate monoclonal antibody and a secondary antibody conjugated to Alexa™ 568. F-actin staining (middle panels) was carried out using Alexa™ Fluor 488 phalloidin. Cells were analysed by confocal microscopy. Co-localization of the two signals is indicated in the merge images (right-hand panels). Scale bars represent 10 microns.
Figure 11B:
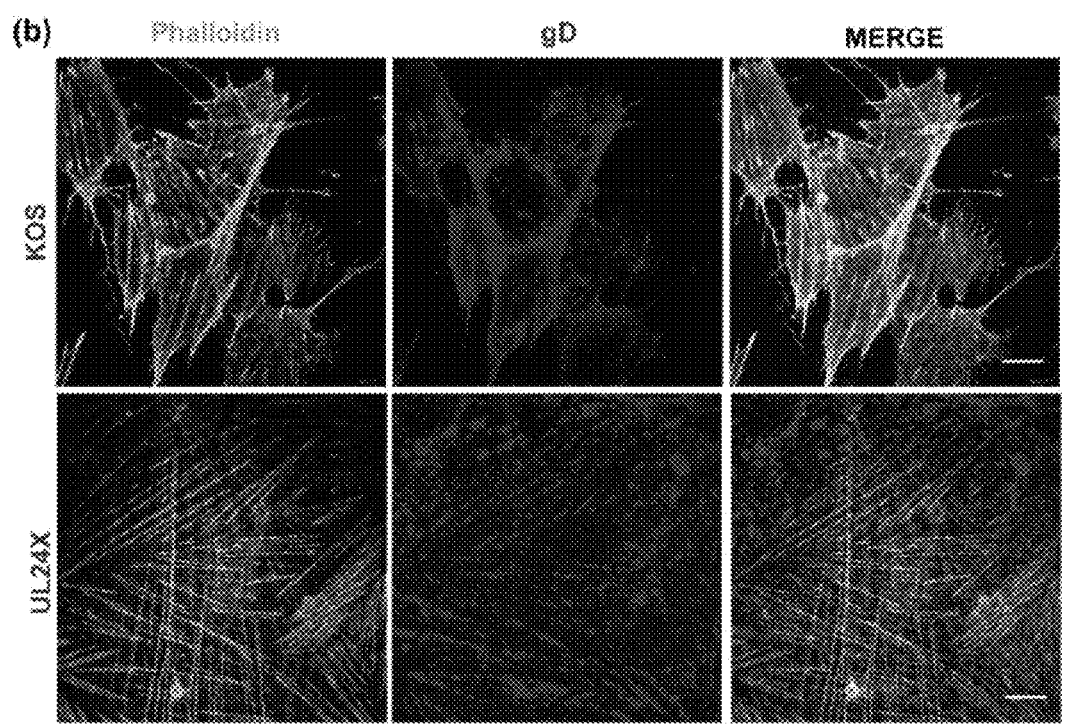

The linear staining pattern for gB and gD in UL24X-infected cells was reminiscent of cytoskeletal structures. Based on the hypothesis that UL24 has an impact on the latter stages of virion morphogenesis, it was tested whether UL24 affected the distribution of gB and gD with regards to the cortical actin filaments in the cell. HFFs were infected with either KOS or UL24X, fixed at 18 hpi, and co-stained for gB or gD and phalloidin, which stains F-actin (Invitrogen) (FIG. 11). In KOS-infected cells, partial co-localization of gB staining with phalloidin was observed (FIG. 11A); however, in UL24X-infected cells a marked reduction in co-localization of the viral glycoproteins and cortical actin was observed (FIG. 11A). Similar results were obtained for gD (FIG. 11B).

Figure 12:
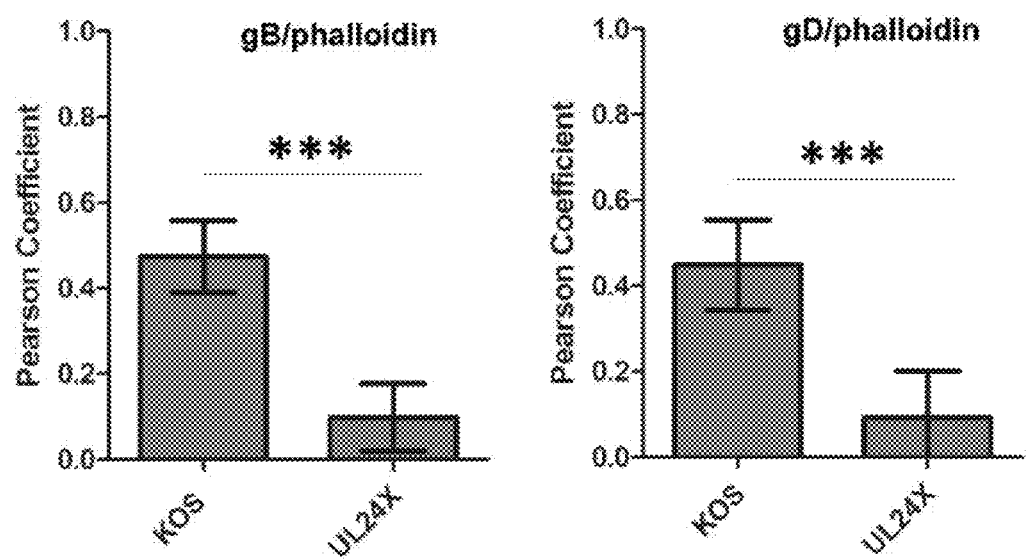
FIG. 12 shows the quantification of the impact of UL24 on co-localization of gB and gD with F-actin. Histograms show the Pearson's coefficients calculated for co-localization of the indicated viral glycoprotein with F-actin in cells infected with either the wild-type virus KOS or UL24X. Each result shown represents the average for two independent experiments in which the co-localization of gB and gD with F-actin was analysed for a total of 20 fields of views which represent more than 100 cells for each condition. Error bars represent the standard error of the means. (*** p<0.0001).

In order to quantify the extent of co-localization of the glycoproteins and F-actin in both KOS- and UL24X-infected cells, Pearson's correlation coefficients were calculated as described above in Example 1, and the results are depicted in FIG. 12. For KOS-infected cells, the following Pearson's correlation coefficients were calculated: $r=0.4290\pm0.01184$ for gB and $0.4148\pm0.01585$ for gD, which indicated a significant association between both gB and gD with F-actin in KOS-infected cells. In contrast, in UL24X-infected cells, the calculated Pearson's correlation coefficients were as follows: $r=0.1450\pm0.01445$ for gB and $0.1245\pm0.01391$ for gD, which represented a significant decrease in the degree of co-localization ($p<0.0001$). Thus, the quantification confirmed that the co-localization association of gB and gD with F-actin at late times in infection was affected by UL24, and thus that UL24 plays a role in the association of viral glycoproteins involved in fusion events with microfilaments.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

What is claimed is:

1. A method for determining whether an agent may be useful for inhibiting the interaction between herpesvirus UL24 and non-muscle myosin type IIa (NM2a), wherein said method comprises contacting the UL24 polypeptide of SEQ ID NO:2 and the NM2a polypeptide of SEQ ID NO:4 in the presence of said agent, and determining whether the interaction between said UL24 and NM2a polypeptides is inhibited in the presence of said agent, wherein inhibition of the interaction between said UL24 and NM2a polypeptides in the presence of said agent is indicative that said agent may be useful for inhibiting the interaction between UL24 and NM2a.

2. The method of claim 1, wherein said UL24 polypeptide and/or said NM2a polypeptide are expressed in an isolated cell.

3. The method of claim 2, wherein said isolated cell is an isolated cell transfected or transformed with (i) a nucleic acid encoding said UL24 polypeptide of SEQ ID NO:2; (ii) a nucleic acid encoding said NM2a polypeptide of SEQ ID NO:4; or (iii) both (i) and (ii).

* * * * *

SEQUENCE LISTING

```
<160> NUMBER OF SEQ ID NOS: 30

<210> SEQ ID NO 1
<211> LENGTH: 810
<212> TYPE: DNA
<213> ORGANISM: herpes simplex virus 1
<220> FEATURE:
<221> NAME/KEY: CDS
<222> LOCATION: (1)..(810)

<400> SEQUENCE: 1 atg gcc gcg aga acg cgc agc ctg gtc gaa cgc aga cgc gtg ttg atg       48
Met Ala Ala Arg Thr Arg Ser Leu Val Glu Arg Arg Arg Val Leu Met
1               5                   10                  15 gca ggg gta cga agc cat acg cgc ttc tac aag gcg ctg gcc gaa gag       96
Ala Gly Val Arg Ser His Thr Arg Phe Tyr Lys Ala Leu Ala Glu Glu
            20                  25                  30 gtg cgg gag ttt cac gcc acc aag atc tgc ggc acg ctg ttg acg ctg      144
Val Arg Glu Phe His Ala Thr Lys Ile Cys Gly Thr Leu Leu Thr Leu
        35                  40                  45 tta agc ggg tcg ctg cag ggt cgc tcg gta ttc gag gcc aca cgc gtc      192
Leu Ser Gly Ser Leu Gln Gly Arg Ser Val Phe Glu Ala Thr Arg Val
    50                  55                  60 acc tta ata tgc gaa gtg gac ctg gga ccg cgc cgc ccc gac tgc atc      240
Thr Leu Ile Cys Glu Val Asp Leu Gly Pro Arg Arg Pro Asp Cys Ile
65                  70                  75                  80 tgc gtg ttc gaa ttc gcc aat gac aag acg ctg ggc ggg gtt tgt gtc      288
Cys Val Phe Glu Phe Ala Asn Asp Lys Thr Leu Gly Gly Val Cys Val
                85                  90                  95 atc ata gaa cta aag aca tgc aaa tat att tct tcc ggg gac acc gcc      336
Ile Ile Glu Leu Lys Thr Cys Lys Tyr Ile Ser Ser Gly Asp Thr Ala
```

```
                  100                 105                 110
agc aaa cgc gag caa cgg gcc acg ggg atg aag cag ctg cgc cac tcc     384
Ser Lys Arg Glu Gln Arg Ala Thr Gly Met Lys Gln Leu Arg His Ser
    115                 120                 125 ctg aag ctc ctg cag tcc ctc gcg cct ccg ggt gac aag ata gtg tac     432
Leu Lys Leu Leu Gln Ser Leu Ala Pro Pro Gly Asp Lys Ile Val Tyr
130                 135                 140 ctg tgc ccc gtc ctg gtg ttt gtc gcc caa cgg acg ctc cgc gtc agc     480
Leu Cys Pro Val Leu Val Phe Val Ala Gln Arg Thr Leu Arg Val Ser
145                 150                 155                 160 cgc gtg acc cgg ctc gtc ccg cag aag gtc tcc ggt aat atc acc gca     528
Arg Val Thr Arg Leu Val Pro Gln Lys Val Ser Gly Asn Ile Thr Ala
            165                 170                 175 gtc gtg cgg atg ctc cag agc ctg tcc acg tat acg gtc ccc att gag     576
Val Val Arg Met Leu Gln Ser Leu Ser Thr Tyr Thr Val Pro Ile Glu
                180                 185                 190 cct agg acc cag cga gcc cgt cgc cgc ggc ggc gcc gcc cgg ggg         624
Pro Arg Thr Gln Arg Ala Arg Arg Arg Gly Gly Ala Ala Arg Gly
                    195                 200                 205 tct gcg agc aga ccg aaa agg tca cac tct ggg gcg cgc gac ccg ccc     672
Ser Ala Ser Arg Pro Lys Arg Ser His Ser Gly Ala Arg Asp Pro Pro
    210                 215                 220 gag tca gcg gcc cgc cag tta cca ccc gcc gac caa acc ccc acc tcc     720
Glu Ser Ala Ala Arg Gln Leu Pro Pro Ala Asp Gln Thr Pro Thr Ser
225                 230                 235                 240 acg gag ggc ggg ggg gtg ctt aag agg atc gcg gcg ctc ttc tgc gtg     768
Thr Glu Gly Gly Gly Val Leu Lys Arg Ile Ala Ala Leu Phe Cys Val
                245                 250                 255 ccc gtg gcc acc aag acc aaa ccc cga gcc gcc tcc gaa tga             810
Pro Val Ala Thr Lys Thr Lys Pro Arg Ala Ala Ser Glu
                260                 265

<210> SEQ ID NO 2
<211> LENGTH: 269
<212> TYPE: PRT
<213> ORGANISM: herpes simplex virus 1

<400> SEQUENCE: 2

Met Ala Ala Arg Thr Arg Ser Leu Val Glu Arg Arg Val Leu Met
1               5                   10                  15

Ala Gly Val Arg Ser His Thr Arg Phe Tyr Lys Ala Leu Ala Glu Glu
                20                  25                  30

Val Arg Glu Phe His Ala Thr Lys Ile Cys Gly Thr Leu Leu Thr Leu
            35                  40                  45

Leu Ser Gly Ser Leu Gln Gly Arg Ser Val Phe Glu Ala Thr Arg Val
    50                  55                  60

Thr Leu Ile Cys Glu Val Asp Leu Gly Pro Arg Pro Asp Cys Ile
65                  70                  75                  80

Cys Val Phe Glu Phe Ala Asn Asp Lys Thr Leu Gly Gly Val Cys Val
                85                  90                  95

Ile Ile Glu Leu Lys Thr Cys Lys Tyr Ile Ser Ser Gly Asp Thr Ala
            100                 105                 110

Ser Lys Arg Glu Gln Arg Ala Thr Gly Met Lys Gln Leu Arg His Ser
    115                 120                 125

Leu Lys Leu Leu Gln Ser Leu Ala Pro Pro Gly Asp Lys Ile Val Tyr
130                 135                 140

Leu Cys Pro Val Leu Val Phe Val Ala Gln Arg Thr Leu Arg Val Ser
145                 150                 155                 160
```

```
Arg Val Thr Arg Leu Val Pro Gln Lys Val Ser Gly Asn Ile Thr Ala
            165                 170                 175

Val Val Arg Met Leu Gln Ser Leu Ser Thr Tyr Thr Val Pro Ile Glu
            180                 185                 190

Pro Arg Thr Gln Arg Ala Arg Arg Arg Gly Gly Ala Ala Arg Gly
            195                 200                 205

Ser Ala Ser Arg Pro Lys Arg Ser His Ser Gly Ala Arg Asp Pro Pro
            210                 215                 220

Glu Ser Ala Ala Arg Gln Leu Pro Pro Ala Asp Gln Thr Pro Thr Ser
225                 230                 235                 240

Thr Glu Gly Gly Gly Val Leu Lys Arg Ile Ala Ala Leu Phe Cys Val
            245                 250                 255

Pro Val Ala Thr Lys Thr Lys Pro Arg Ala Ala Ser Glu
            260                 265

<210> SEQ ID NO 3
<211> LENGTH: 7505
<212> TYPE: DNA
<213> ORGANISM: Homo sapiens
<220> FEATURE:
<221> NAME/KEY: CDS
<222> LOCATION: (232)..(6114)

<400> SEQUENCE: 3
```

| | |
|---|---:|
| gagggcgggg cgggaaggcg gcgaggagcc gagctgggtg cggtgaggcg cgcagatcac | 60 |
| cgcggttcct gggcagggca cggaaggcta agcaaggctg acctgctgca gctcccgcct | 120 |
| cgtgcgctcg ccccacccgg ccgccgcccg agcgctcgag aaagtcctct cgggagaagc | 180 |
| agcgcctgtt cccgggggcag atccaggttc aggtcctggc tataagtcac c atg gca | 237 |
|                                                                                            Met Ala<br>                                                                                               1 |
| cag caa gct gcc gat aag tat ctc tat gtg gat aaa aac ttc atc aac<br>Gln Gln Ala Ala Asp Lys Tyr Leu Tyr Val Asp Lys Asn Phe Ile Asn<br>     5                   10                 15 | 285 |
| aat ccg ctg gcc cag gcc gac tgg gct gcc aag aag ctg gta tgg gtg<br>Asn Pro Leu Ala Gln Ala Asp Trp Ala Ala Lys Lys Leu Val Trp Val<br> 20                   25                 30 | 333 |
| cct tcc gac aag agt ggc ttt gag cca gcc agc ctc aag gag gag gtg<br>Pro Ser Asp Lys Ser Gly Phe Glu Pro Ala Ser Leu Lys Glu Glu Val<br>35                 40                 45                 50 | 381 |
| ggc gag gag gcc atc gtg gag ctg gtg gag aat ggg aag aag gtg aag<br>Gly Glu Glu Ala Ile Val Glu Leu Val Glu Asn Gly Lys Lys Val Lys<br>               55                 60                 65 | 429 |
| gtg aac aag gat gac atc cag aag atg aac ccg ccc aag ttc tcc aag<br>Val Asn Lys Asp Asp Ile Gln Lys Met Asn Pro Pro Lys Phe Ser Lys<br>     70                   75                 80 | 477 |
| gtg gag gac atg gca gag ctc acg tgc ctc aac gaa gcc tcg gtg ctg<br>Val Glu Asp Met Ala Glu Leu Thr Cys Leu Asn Glu Ala Ser Val Leu<br> 85                   90                 95 | 525 |
| cac aac ctc aag gag cgt tac tac tca ggg ctc atc tac acc tat tca<br>His Asn Leu Lys Glu Arg Tyr Tyr Ser Gly Leu Ile Tyr Thr Tyr Ser<br>              100              105             110 | 573 |
| ggc ctg ttc tgt gtg gtc atc aat cct tac aag aac ctg ccc atc tac<br>Gly Leu Phe Cys Val Val Ile Asn Pro Tyr Lys Asn Leu Pro Ile Tyr<br>115                 120               125             130 | 621 |
| tct gaa gag att gtg gaa atg tac aag ggc aag aag agg cac gag atg<br>Ser Glu Glu Ile Val Glu Met Tyr Lys Gly Lys Lys Arg His Glu Met<br>               135               140             145 | 669 |

| | |
|---|---|
| ccc cct cac atc tat gcc atc aca gac acc gcc tac agg agt atg atg<br>Pro Pro His Ile Tyr Ala Ile Thr Asp Thr Ala Tyr Arg Ser Met Met<br>150                          155                       160 | 717 |
| caa gac cga gaa gat caa tcc atc ttg tgc act ggt gaa tct gga gct<br>Gln Asp Arg Glu Asp Gln Ser Ile Leu Cys Thr Gly Glu Ser Gly Ala<br>165                       170                      175 | 765 |
| ggc aag acg gag aac acc aag aag gtc atc cag tat ctg gcg tac gtg<br>Gly Lys Thr Glu Asn Thr Lys Lys Val Ile Gln Tyr Leu Ala Tyr Val<br>180                       185                   190 | 813 |
| gcg tcc tcg cac aag agc aag aag gac cag ggc gag ctg gag cgg cag<br>Ala Ser Ser His Lys Ser Lys Lys Asp Gln Gly Glu Leu Glu Arg Gln<br>195                       200                       205                   210 | 861 |
| ctg ctg cag gcc aac ccc atc ctg gag gcc ttc ggg aac gcc aag acc<br>Leu Leu Gln Ala Asn Pro Ile Leu Glu Ala Phe Gly Asn Ala Lys Thr<br>               215                       220                       225 | 909 |
| gtg aag aat gac aac tcc tcc cgc ttc ggc aaa ttc att cgc atc aac<br>Val Lys Asn Asp Asn Ser Ser Arg Phe Gly Lys Phe Ile Arg Ile Asn<br>         230                       235                       240 | 957 |
| ttt gat gtc aat ggc tac att gtt gga gcc aac att gag act tat ctt<br>Phe Asp Val Asn Gly Tyr Ile Val Gly Ala Asn Ile Glu Thr Tyr Leu<br>         245                       250                       255 | 1005 |
| ttg gag aaa tct cgt gct atc cgc caa gcc aag gaa gaa cgg acc ttc<br>Leu Glu Lys Ser Arg Ala Ile Arg Gln Ala Lys Glu Glu Arg Thr Phe<br>260                          265                       270 | 1053 |
| cac atc ttc tat tat ctc ctg tct ggg gct gga gag cac ctg aag acc<br>His Ile Phe Tyr Tyr Leu Leu Ser Gly Ala Gly Glu His Leu Lys Thr<br>275                       280                       285                   290 | 1101 |
| gat ctc ctg ttg gag ccg tac aac aaa tac cgc ttc ctg tcc aat gga<br>Asp Leu Leu Leu Glu Pro Tyr Asn Lys Tyr Arg Phe Leu Ser Asn Gly<br>                       295                       300                       305 | 1149 |
| cac gtc acc atc ccc ggg cag cag gac aag gac atg ttc cag gag acc<br>His Val Thr Ile Pro Gly Gln Gln Asp Lys Asp Met Phe Gln Glu Thr<br>               310                       315                       320 | 1197 |
| atg gag gcc atg agg att atg ggc atc cca gaa gag gag caa atg ggc<br>Met Glu Ala Met Arg Ile Met Gly Ile Pro Glu Glu Glu Gln Met Gly<br>               325                       330                       335 | 1245 |
| ctg ctg cgg gtc atc tca ggg gtt ctt cag ctc ggc aac atc gtc ttc<br>Leu Leu Arg Val Ile Ser Gly Val Leu Gln Leu Gly Asn Ile Val Phe<br>340                          345                       350 | 1293 |
| aag aag gag cgg aac act gac cag gcg tcc atg ccc gac aac aca gct<br>Lys Lys Glu Arg Asn Thr Asp Gln Ala Ser Met Pro Asp Asn Thr Ala<br>355                          360                       365                   370 | 1341 |
| gcc caa aag gtg tcc cat ctc ttg ggt atc aat gtg acc gat ttc acc<br>Ala Gln Lys Val Ser His Leu Leu Gly Ile Asn Val Thr Asp Phe Thr<br>               375                       380                       385 | 1389 |
| aga gga atc ctc acc ccg cgc atc aag gtg gga cgg gat tac gtc cag<br>Arg Gly Ile Leu Thr Pro Arg Ile Lys Val Gly Arg Asp Tyr Val Gln<br>         390                       395                       400 | 1437 |
| aag gcg cag act aaa gag cag gct gac ttt gcc atc gag gcc ttg gcc<br>Lys Ala Gln Thr Lys Glu Gln Ala Asp Phe Ala Ile Glu Ala Leu Ala<br>               405                       410                       415 | 1485 |
| aag gcg acc tat gag cgg atg ttc cgc tgg ctg gtg ctg cgc atc aac<br>Lys Ala Thr Tyr Glu Arg Met Phe Arg Trp Leu Val Leu Arg Ile Asn<br>420                          425                       430 | 1533 |
| aag gct ctg gac aag acc aag agg cag ggc gcc tcc ttc atc ggg atc<br>Lys Ala Leu Asp Lys Thr Lys Arg Gln Gly Ala Ser Phe Ile Gly Ile<br>435                          440                       445                   450 | 1581 |
| ctg gac att gcc ggc ttc gag atc ttt gat ctg aac tcg ttt gag cag<br>Leu Asp Ile Ala Gly Phe Glu Ile Phe Asp Leu Asn Ser Phe Glu Gln<br>               455                       460                       465 | 1629 |

-continued

| | | | | | | | | | | | | | | | | |
|---|---|---|---|---|---|---|---|---|---|---|---|---|---|---|---|---|
| ctg | tgc | atc | aat | tac | acc | aat | gag | aag | ctg | cag | cag | ctc | ttc | aac | cac | 1677 |
| Leu | Cys | Ile | Asn | Tyr | Thr | Asn | Glu | Lys | Leu | Gln | Gln | Leu | Phe | Asn | His | |
| | | | | 470 | | | | 475 | | | | | 480 | | | |

| | | | | | | | | | | | | | | | | |
|---|---|---|---|---|---|---|---|---|---|---|---|---|---|---|---|---|
| acc | atg | ttc | atc | ctg | gag | cag | gag | tac | cag | cgc | gag | ggc | atc | gag | | 1725 |
| Thr | Met | Phe | Ile | Leu | Glu | Gln | Glu | Tyr | Gln | Arg | Glu | Gly | Ile | Glu | | |
| | | 485 | | | | | 490 | | | | | 495 | | | | |

| | | | | | | | | | | | | | | | | |
|---|---|---|---|---|---|---|---|---|---|---|---|---|---|---|---|---|
| tgg | aac | ttc | atc | gac | ttt | ggc | ctc | gac | ctg | cag | ccc | tgc | atc | gac | ctc | 1773 |
| Trp | Asn | Phe | Ile | Asp | Phe | Gly | Leu | Asp | Leu | Gln | Pro | Cys | Ile | Asp | Leu | |
| | 500 | | | | | 505 | | | | | 510 | | | | | |

| | | | | | | | | | | | | | | | | |
|---|---|---|---|---|---|---|---|---|---|---|---|---|---|---|---|---|
| att | gag | aag | cca | gca | ggc | ccc | ccg | ggc | att | ctg | gcc | ctg | ctg | gac | gag | 1821 |
| Ile | Glu | Lys | Pro | Ala | Gly | Pro | Pro | Gly | Ile | Leu | Ala | Leu | Leu | Asp | Glu | |
| 515 | | | | | 520 | | | | | 525 | | | | | 530 | |

| | | | | | | | | | | | | | | | | |
|---|---|---|---|---|---|---|---|---|---|---|---|---|---|---|---|---|
| gag | tgc | tgg | ttc | ccc | aaa | gcc | acc | gac | aag | agc | ttc | gtg | gag | aag | gtg | 1869 |
| Glu | Cys | Trp | Phe | Pro | Lys | Ala | Thr | Asp | Lys | Ser | Phe | Val | Glu | Lys | Val | |
| | | | 535 | | | | | 540 | | | | | 545 | | | |

| | | | | | | | | | | | | | | | | |
|---|---|---|---|---|---|---|---|---|---|---|---|---|---|---|---|---|
| atg | cag | gag | cag | ggc | acc | cac | ccc | aag | ttc | cag | aag | ccc | aag | cag | ctg | 1917 |
| Met | Gln | Glu | Gln | Gly | Thr | His | Pro | Lys | Phe | Gln | Lys | Pro | Lys | Gln | Leu | |
| | | 550 | | | | | 555 | | | | | 560 | | | | |

| | | | | | | | | | | | | | | | | |
|---|---|---|---|---|---|---|---|---|---|---|---|---|---|---|---|---|
| aag | gac | aaa | gct | gat | ttc | tgc | att | atc | cac | tat | gcc | ggc | aag | gtg | gat | 1965 |
| Lys | Asp | Lys | Ala | Asp | Phe | Cys | Ile | Ile | His | Tyr | Ala | Gly | Lys | Val | Asp | |
| | 565 | | | | | 570 | | | | | 575 | | | | | |

| | | | | | | | | | | | | | | | | |
|---|---|---|---|---|---|---|---|---|---|---|---|---|---|---|---|---|
| tac | aaa | gct | gac | gag | tgg | ctg | atg | aag | aac | atg | gat | ccc | ctg | aat | gac | 2013 |
| Tyr | Lys | Ala | Asp | Glu | Trp | Leu | Met | Lys | Asn | Met | Asp | Pro | Leu | Asn | Asp | |
| 580 | | | | | 585 | | | | | 590 | | | | | | |

| | | | | | | | | | | | | | | | | |
|---|---|---|---|---|---|---|---|---|---|---|---|---|---|---|---|---|
| aac | atc | gcc | aca | ctg | ctc | cac | cag | tcc | tct | gac | aag | ttt | gtc | tcg | gag | 2061 |
| Asn | Ile | Ala | Thr | Leu | Leu | His | Gln | Ser | Ser | Asp | Lys | Phe | Val | Ser | Glu | |
| 595 | | | | | 600 | | | | | 605 | | | | | 610 | |

| | | | | | | | | | | | | | | | | |
|---|---|---|---|---|---|---|---|---|---|---|---|---|---|---|---|---|
| ctg | tgg | aag | gat | gtg | gac | cgc | atc | atc | ggc | ctg | gac | cag | gtg | gcc | ggc | 2109 |
| Leu | Trp | Lys | Asp | Val | Asp | Arg | Ile | Ile | Gly | Leu | Asp | Gln | Val | Ala | Gly | |
| | | | | 615 | | | | | 620 | | | | | 625 | | |

| | | | | | | | | | | | | | | | | |
|---|---|---|---|---|---|---|---|---|---|---|---|---|---|---|---|---|
| atg | tcg | gag | acc | gca | ctg | ccc | ggg | gcc | ttc | aag | acg | cgg | aag | ggc | atg | 2157 |
| Met | Ser | Glu | Thr | Ala | Leu | Pro | Gly | Ala | Phe | Lys | Thr | Arg | Lys | Gly | Met | |
| | | | 630 | | | | | 635 | | | | | 640 | | | |

| | | | | | | | | | | | | | | | | |
|---|---|---|---|---|---|---|---|---|---|---|---|---|---|---|---|---|
| ttc | cgc | act | gtg | ggg | cag | ctt | tac | aag | gag | cag | ctg | gcc | aag | ctg | atg | 2205 |
| Phe | Arg | Thr | Val | Gly | Gln | Leu | Tyr | Lys | Glu | Gln | Leu | Ala | Lys | Leu | Met | |
| | | 645 | | | | | 650 | | | | | 655 | | | | |

| | | | | | | | | | | | | | | | | |
|---|---|---|---|---|---|---|---|---|---|---|---|---|---|---|---|---|
| gct | acg | ctg | agg | aac | acg | aac | ccc | aac | ttt | gtc | cgc | tgc | atc | atc | ccc | 2253 |
| Ala | Thr | Leu | Arg | Asn | Thr | Asn | Pro | Asn | Phe | Val | Arg | Cys | Ile | Ile | Pro | |
| 660 | | | | | 665 | | | | | 670 | | | | | | |

| | | | | | | | | | | | | | | | | |
|---|---|---|---|---|---|---|---|---|---|---|---|---|---|---|---|---|
| aac | cac | gag | aag | aag | gcc | ggc | aag | ctg | gac | ccg | cat | ctc | gtg | ctg | gac | 2301 |
| Asn | His | Glu | Lys | Lys | Ala | Gly | Lys | Leu | Asp | Pro | His | Leu | Val | Leu | Asp | |
| 675 | | | | | 680 | | | | | 685 | | | | | 690 | |

| | | | | | | | | | | | | | | | | |
|---|---|---|---|---|---|---|---|---|---|---|---|---|---|---|---|---|
| cag | ctg | cgc | tgc | aac | ggt | gtt | ctc | gag | ggc | atc | cgt | atc | tgc | cgc | cag | 2349 |
| Gln | Leu | Arg | Cys | Asn | Gly | Val | Leu | Glu | Gly | Ile | Arg | Ile | Cys | Arg | Gln | |
| | | | | 695 | | | | | 700 | | | | | 705 | | |

| | | | | | | | | | | | | | | | | |
|---|---|---|---|---|---|---|---|---|---|---|---|---|---|---|---|---|
| ggc | ttc | ccc | aac | agg | gtg | gtc | ttc | cag | gag | ttt | cgg | cag | aga | tat | gag | 2397 |
| Gly | Phe | Pro | Asn | Arg | Val | Val | Phe | Gln | Glu | Phe | Arg | Gln | Arg | Tyr | Glu | |
| | | | 710 | | | | | 715 | | | | | 720 | | | |

| | | | | | | | | | | | | | | | | |
|---|---|---|---|---|---|---|---|---|---|---|---|---|---|---|---|---|
| atc | ctg | act | cca | aac | tcc | att | ccc | aag | ggt | ttc | atg | gac | ggg | aag | cag | 2445 |
| Ile | Leu | Thr | Pro | Asn | Ser | Ile | Pro | Lys | Gly | Phe | Met | Asp | Gly | Lys | Gln | |
| | | 725 | | | | | 730 | | | | | 735 | | | | |

| | | | | | | | | | | | | | | | | |
|---|---|---|---|---|---|---|---|---|---|---|---|---|---|---|---|---|
| gcg | tgc | gtg | ctc | atg | ata | aaa | gcc | ctg | gag | ctc | gac | agc | aat | ctg | tac | 2493 |
| Ala | Cys | Val | Leu | Met | Ile | Lys | Ala | Leu | Glu | Leu | Asp | Ser | Asn | Leu | Tyr | |
| 740 | | | | | 745 | | | | | 750 | | | | | | |

| | | | | | | | | | | | | | | | | |
|---|---|---|---|---|---|---|---|---|---|---|---|---|---|---|---|---|
| cgc | att | ggc | cag | agc | aaa | gtc | ttc | ttc | cgt | gcc | ggt | gtg | ctg | gcc | cac | 2541 |
| Arg | Ile | Gly | Gln | Ser | Lys | Val | Phe | Phe | Arg | Ala | Gly | Val | Leu | Ala | His | |
| 755 | | | | | 760 | | | | | 765 | | | | | 770 | |

| | | | | | | | | | | | | | | | | |
|---|---|---|---|---|---|---|---|---|---|---|---|---|---|---|---|---|
| ctg | gag | gag | gag | cga | gac | ctg | aag | atc | acc | gac | gtc | atc | ata | ggg | ttc | 2589 |
| Leu | Glu | Glu | Glu | Arg | Asp | Leu | Lys | Ile | Thr | Asp | Val | Ile | Ile | Gly | Phe | |

-continued

|  |  |  |
|---|---|---|
| 775 | 780 | 785 |

| | |
|---|---|
| cag gcc tgc tgc agg ggc tac ctg gcc agg aaa gca ttt gcc aag cgg<br>Gln Ala Cys Cys Arg Gly Tyr Leu Ala Arg Lys Ala Phe Ala Lys Arg<br>        790                    795                    800 | 2637 |
| cag cag cag ctt acc gcc atg aag gtc ctc cag cgg aac tgc gct gcc<br>Gln Gln Gln Leu Thr Ala Met Lys Val Leu Gln Arg Asn Cys Ala Ala<br>        805                    810                    815 | 2685 |
| tac ctg aag ctg cgg aac tgg cag tgg tgg cgg ctc ttc acc aag gtc<br>Tyr Leu Lys Leu Arg Asn Trp Gln Trp Trp Arg Leu Phe Thr Lys Val<br>820                      825                    830 | 2733 |
| aag ccg ctg ctg cag gtg agc cgg cag gag gag gag atg atg gcc aag<br>Lys Pro Leu Leu Gln Val Ser Arg Gln Glu Glu Glu Met Met Ala Lys<br>835                      840                    845                    850 | 2781 |
| gag gag gag ctg gtg aag gtc aga gag aag cag ctg gct gcg gag aac<br>Glu Glu Glu Leu Val Lys Val Arg Glu Lys Gln Leu Ala Ala Glu Asn<br>                        855                    860                    865 | 2829 |
| agg ctc acg gag atg gag acg ctg cag tct cag ctc atg gca gag aaa<br>Arg Leu Thr Glu Met Glu Thr Leu Gln Ser Gln Leu Met Ala Glu Lys<br>        870                    875                    880 | 2877 |
| ttg cag ctg cag gag cag ctc cag gca gaa acc gag ctg tgt gcc gag<br>Leu Gln Leu Gln Glu Gln Leu Gln Ala Glu Thr Glu Leu Cys Ala Glu<br>885                      890                    895 | 2925 |
| gct gag gag ctc cgg gcc cgc ctg acc gcc aag aag cag gaa tta gaa<br>Ala Glu Glu Leu Arg Ala Arg Leu Thr Ala Lys Lys Gln Glu Leu Glu<br>900                      905                    910 | 2973 |
| gag atc tgc cat gac cta gag gcc agg gtg gag gag gag gag cgc<br>Glu Ile Cys His Asp Leu Glu Ala Arg Val Glu Glu Glu Glu Arg<br>915                      920                    925                    930 | 3021 |
| tgc cag cac ctg cag gcg gag aag aag aag atg cag cag aac atc cag<br>Cys Gln His Leu Gln Ala Glu Lys Lys Lys Met Gln Gln Asn Ile Gln<br>                        935                    940                    945 | 3069 |
| gag ctt gag gag cag ctg gag gag gag gag agc gcc cgg cag aag ctg<br>Glu Leu Glu Glu Gln Leu Glu Glu Glu Glu Ser Ala Arg Gln Lys Leu<br>        950                    955                    960 | 3117 |
| cag ctg gag aag gtg acc acc gag gcg aag ctg aaa aag ctg gag gag<br>Gln Leu Glu Lys Val Thr Thr Glu Ala Lys Leu Lys Lys Leu Glu Glu<br>        965                    970                    975 | 3165 |
| gag cag atc atc ctg gag gac cag aac tgc aag ctg gcc aag gaa aag<br>Glu Gln Ile Ile Leu Glu Asp Gln Asn Cys Lys Leu Ala Lys Glu Lys<br>980                      985                    990 | 3213 |
| aaa ctg ctg gaa gac aga ata gct gag ttc acc acc aac ctc aca<br>Lys Leu Leu Glu Asp Arg Ile Ala Glu Phe Thr Thr Asn Leu Thr<br>995                      1000                1005 | 3258 |
| gaa gag gag gag aaa tct aag agc ctc gcc aag ctc aag aac aag<br>Glu Glu Glu Glu Lys Ser Lys Ser Leu Ala Lys Leu Lys Asn Lys<br>1010                 1015                1020 | 3303 |
| cat gag gca atg atc act gac ttg gaa gag cgc ctc cgc agg gag<br>His Glu Ala Met Ile Thr Asp Leu Glu Glu Arg Leu Arg Arg Glu<br>1025                 1030                1035 | 3348 |
| gag aag cag cga cag gag ctg gag aag acc cgc cgg aag ctg gag<br>Glu Lys Gln Arg Gln Glu Leu Glu Lys Thr Arg Arg Lys Leu Glu<br>1040                 1045                1050 | 3393 |
| gga gac tcc aca gac ctc agc gac cag atc gcc gag ctc cag gcc<br>Gly Asp Ser Thr Asp Leu Ser Asp Gln Ile Ala Glu Leu Gln Ala<br>1055                 1060                1065 | 3438 |
| cag atc gcg gag ctc aag atg cag ctg gcc aag aaa gag gag gag<br>Gln Ile Ala Glu Leu Lys Met Gln Leu Ala Lys Lys Glu Glu Glu<br>1070                 1075                1080 | 3483 |
| ctc cag gcc gcc ctg gcc aga gtg gaa gag gaa gct gcc cag aag | 3528 |

```
Leu Gln Ala Ala Leu Ala Arg Val Glu Glu Glu Ala Ala Gln Lys
1085                1090                1095 aac atg gcc ctc aag aag atc cgg gag ctg gaa tct cag atc tct     3573
Asn Met Ala Leu Lys Lys Ile Arg Glu Leu Glu Ser Gln Ile Ser
1100                1105                1110 gaa ctc cag gaa gac ctg gag tct gag cgt gct tcc agg aat aaa     3618
Glu Leu Gln Glu Asp Leu Glu Ser Glu Arg Ala Ser Arg Asn Lys
1115                1120                1125 gct gag aag cag aaa cgg gac ctt ggg gaa gag cta gag gct ctg     3663
Ala Glu Lys Gln Lys Arg Asp Leu Gly Glu Glu Leu Glu Ala Leu
1130                1135                1140 aaa aca gag ttg gag gac acg ctg gat tcc aca gct gcc cag cag     3708
Lys Thr Glu Leu Glu Asp Thr Leu Asp Ser Thr Ala Ala Gln Gln
1145                1150                1155 gag ctc agg tca aaa cgt gag cag gag gtg aac atc ctg aag aag     3753
Glu Leu Arg Ser Lys Arg Glu Gln Glu Val Asn Ile Leu Lys Lys
1160                1165                1170 acc ctg gag gag gag gcc aag acc cac gag gcc cag atc cag gag     3798
Thr Leu Glu Glu Glu Ala Lys Thr His Glu Ala Gln Ile Gln Glu
1175                1180                1185 atg agg cag aag cac tca cag gcc gtg gag gag ctg gcg gag cag     3843
Met Arg Gln Lys His Ser Gln Ala Val Glu Glu Leu Ala Glu Gln
1190                1195                1200 ctg gag cag acg aag cgg gtg aaa gca aac ctc gag aag gca aag     3888
Leu Glu Gln Thr Lys Arg Val Lys Ala Asn Leu Glu Lys Ala Lys
1205                1210                1215 cag act ctg gag aac gag cgg ggg gag ctg gcc aac gag gtg aag     3933
Gln Thr Leu Glu Asn Glu Arg Gly Glu Leu Ala Asn Glu Val Lys
1220                1225                1230 gtg ctg ctg cag ggc aaa ggg gac tcg gag cac aag cgc aag aaa     3978
Val Leu Leu Gln Gly Lys Gly Asp Ser Glu His Lys Arg Lys Lys
1235                1240                1245 gtg gag gcg cag ctg cag gag ctg cag gtc aag ttc aac gag gga     4023
Val Glu Ala Gln Leu Gln Glu Leu Gln Val Lys Phe Asn Glu Gly
1250                1255                1260 gag cgc gtg cgc aca gag ctg gcc gac aag gtc acc aag ctg cag     4068
Glu Arg Val Arg Thr Glu Leu Ala Asp Lys Val Thr Lys Leu Gln
1265                1270                1275 gtg gag ctg gac aac gtg acc ggg ctt ctc agc cag tcc gac agc     4113
Val Glu Leu Asp Asn Val Thr Gly Leu Leu Ser Gln Ser Asp Ser
1280                1285                1290 aag tcc agc aag ctc acc aag gac ttc tcc gcg ctg gag tcc cag     4158
Lys Ser Ser Lys Leu Thr Lys Asp Phe Ser Ala Leu Glu Ser Gln
1295                1300                1305 ctg cag gac act cag gag ctg ctg cag gag gag aac cgg cag aag     4203
Leu Gln Asp Thr Gln Glu Leu Leu Gln Glu Glu Asn Arg Gln Lys
1310                1315                1320 ctg agc ctg agc acc aag ctc aag cag gtg gag gac gag aag aat     4248
Leu Ser Leu Ser Thr Lys Leu Lys Gln Val Glu Asp Glu Lys Asn
1325                1330                1335 tcc ttc cgg gag cag ctg gag gag gag gag gcc aag cac aac     4293
Ser Phe Arg Glu Gln Leu Glu Glu Glu Glu Ala Lys His Asn
1340                1345                1350 ctg gag aag cag atc gcc acc ctc cat gcc cag gtg gcc gac atg     4338
Leu Glu Lys Gln Ile Ala Thr Leu His Ala Gln Val Ala Asp Met
1355                1360                1365 aaa aag aag atg gag gac agt gtg ggg tgc ctg gaa act gct gag     4383
Lys Lys Lys Met Glu Asp Ser Val Gly Cys Leu Glu Thr Ala Glu
1370                1375                1380
```

-continued

| | | |
|---|---|---|
| gag gtg aag agg aag ctc cag aag gac ctg gag ggc ctg agc cag<br>Glu Val Lys Arg Lys Leu Gln Lys Asp Leu Glu Gly Leu Ser Gln<br>1385                       1390                       1395 | 4428 |
| cgg cac gag gag aag gtg gcc gcc tac gac aag ctg gag aag acc<br>Arg His Glu Glu Lys Val Ala Ala Tyr Asp Lys Leu Glu Lys Thr<br>1400                       1405                       1410 | 4473 |
| aag acg cgg ctg cag cag gag ctg gac gac ctg ctg gtg gac ctg<br>Lys Thr Arg Leu Gln Gln Glu Leu Asp Asp Leu Leu Val Asp Leu<br>1415                       1420                       1425 | 4518 |
| gac cac cag cgc cag agc gcg tgc aac ctg gag aag aag cag aag<br>Asp His Gln Arg Gln Ser Ala Cys Asn Leu Glu Lys Lys Gln Lys<br>1430                       1435                       1440 | 4563 |
| aag ttt gac cag ctc ctg gcg gag gag aag acc atc tct gcc aag<br>Lys Phe Asp Gln Leu Leu Ala Glu Glu Lys Thr Ile Ser Ala Lys<br>1445                       1450                       1455 | 4608 |
| tat gca gag gag cgc gac cgg gct gag gcg gag gcc cga gag aag<br>Tyr Ala Glu Glu Arg Asp Arg Ala Glu Ala Glu Ala Arg Glu Lys<br>1460                       1465                       1470 | 4653 |
| gag acc aag gct ctg tcg ctg gcc cgg gcc ctg gag gaa gcc atg<br>Glu Thr Lys Ala Leu Ser Leu Ala Arg Ala Leu Glu Glu Ala Met<br>1475                       1480                       1485 | 4698 |
| gag cag aag gcg gag ctg gag cgg ctc aac aag cag ttc cgc acg<br>Glu Gln Lys Ala Glu Leu Glu Arg Leu Asn Lys Gln Phe Arg Thr<br>1490                       1495                       1500 | 4743 |
| gag atg gag gac ctt atg agc tcc aag gat gat gtg ggc aag agt<br>Glu Met Glu Asp Leu Met Ser Ser Lys Asp Asp Val Gly Lys Ser<br>1505                       1510                       1515 | 4788 |
| gtc cac gag ctg gag aag tcc aag cgg gcc cta gag cag cag gtg<br>Val His Glu Leu Glu Lys Ser Lys Arg Ala Leu Glu Gln Gln Val<br>1520                       1525                       1530 | 4833 |
| gag gag atg aag acg cag ctg gaa gag ctg gag gac gag ctg cag<br>Glu Glu Met Lys Thr Gln Leu Glu Glu Leu Glu Asp Glu Leu Gln<br>1535                       1540                       1545 | 4878 |
| gcc acc gaa gat gcc aag ctg cgg ttg gag gtc aac ctg cag gcc<br>Ala Thr Glu Asp Ala Lys Leu Arg Leu Glu Val Asn Leu Gln Ala<br>1550                       1555                       1560 | 4923 |
| atg aag gcc cag ttc gag cgg gac ctg cag ggc cgg gac gag cag<br>Met Lys Ala Gln Phe Glu Arg Asp Leu Gln Gly Arg Asp Glu Gln<br>1565                       1570                       1575 | 4968 |
| agc gag gag aag aag aag cag ctg gtc aga cag gtg cgg gag atg<br>Ser Glu Glu Lys Lys Lys Gln Leu Val Arg Gln Val Arg Glu Met<br>1580                       1585                       1590 | 5013 |
| gag gca gag ctg gag gac gag agg aag cag cgc tcg atg gca gtg<br>Glu Ala Glu Leu Glu Asp Glu Arg Lys Gln Arg Ser Met Ala Val<br>1595                       1600                       1605 | 5058 |
| gcc gcc cgg aag aag ctg gag atg gac ctg aag gac ctg gag gcg<br>Ala Ala Arg Lys Lys Leu Glu Met Asp Leu Lys Asp Leu Glu Ala<br>1610                       1615                       1620 | 5103 |
| cac atc gac tcg gcc aac aag aac cgg gac gaa gcc atc aaa cag<br>His Ile Asp Ser Ala Asn Lys Asn Arg Asp Glu Ala Ile Lys Gln<br>1625                       1630                       1635 | 5148 |
| ctg cgg aag ctg cag gcc cag atg aag gac tgc atg cgc gag ctg<br>Leu Arg Lys Leu Gln Ala Gln Met Lys Asp Cys Met Arg Glu Leu<br>1640                       1645                       1650 | 5193 |
| gat gac acc cgc gcc tct cgt gag gag atc ctg gcc cag gcc aaa<br>Asp Asp Thr Arg Ala Ser Arg Glu Glu Ile Leu Ala Gln Ala Lys<br>1655                       1660                       1665 | 5238 |
| gag aac gag aag aag ctg aag agc atg gag gcc gag atg atc cag<br>Glu Asn Glu Lys Lys Leu Lys Ser Met Glu Ala Glu Met Ile Gln<br>1670                       1675                       1680 | 5283 |

-continued

```
ttg cag gag gaa ctg gca gcc gcg gag cgt gcc aag cgc cag gcc      5328
Leu Gln Glu Glu Leu Ala Ala Ala Glu Arg Ala Lys Arg Gln Ala
1685                1690                1695 cag cag gag cgg gat gag ctg gct gac gag atc gcc aac agc agc      5373
Gln Gln Glu Arg Asp Glu Leu Ala Asp Glu Ile Ala Asn Ser Ser
1700                1705                1710 ggc aaa gga gcc ctg gcg tta gag gag aag cgg cgt ctg gag gcc      5418
Gly Lys Gly Ala Leu Ala Leu Glu Glu Lys Arg Arg Leu Glu Ala
1715                1720                1725 cgc atc gcc cag ctg gag gag gag ctg gag gag gag cag ggc aac      5463
Arg Ile Ala Gln Leu Glu Glu Glu Leu Glu Glu Glu Gln Gly Asn
1730                1735                1740 acg gag ctg atc aac gac cgg ctg aag aag gcc aac ctg cag atc      5508
Thr Glu Leu Ile Asn Asp Arg Leu Lys Lys Ala Asn Leu Gln Ile
1745                1750                1755 gac cag atc aac acc gac ctg aac ctg gag cgc agc cac gcc cag      5553
Asp Gln Ile Asn Thr Asp Leu Asn Leu Glu Arg Ser His Ala Gln
1760                1765                1770 aag aac gag aat gct cgg cag cag ctg gaa cgc cag aac aag gag      5598
Lys Asn Glu Asn Ala Arg Gln Gln Leu Glu Arg Gln Asn Lys Glu
1775                1780                1785 ctt aag gtc aag ctg cag gag atg gag ggc act gtc aag tcc aag      5643
Leu Lys Val Lys Leu Gln Glu Met Glu Gly Thr Val Lys Ser Lys
1790                1795                1800 tac aag gcc tcc atc acc gcc ctc gag gcc aag att gca cag ctg      5688
Tyr Lys Ala Ser Ile Thr Ala Leu Glu Ala Lys Ile Ala Gln Leu
1805                1810                1815 gag gag cag ctg gac aac gag acc aag gag cgc cag gca gcc tgc      5733
Glu Glu Gln Leu Asp Asn Glu Thr Lys Glu Arg Gln Ala Ala Cys
1820                1825                1830 aaa cag gtg cgt cgg acc gag aag aag ctg aag gat gtg ctg ctg      5778
Lys Gln Val Arg Arg Thr Glu Lys Lys Leu Lys Asp Val Leu Leu
1835                1840                1845 cag gtg gat gac gag cgg agg aac gcc gag cag tac aag gac cag      5823
Gln Val Asp Asp Glu Arg Arg Asn Ala Glu Gln Tyr Lys Asp Gln
1850                1855                1860 gcc gac aag gca tct acc cgc ctg aag cag ctc aag cgg cag ctg      5868
Ala Asp Lys Ala Ser Thr Arg Leu Lys Gln Leu Lys Arg Gln Leu
1865                1870                1875 gag gag gcc gaa gag gag gcc cag cgg gcc aac gcc tcc cgc cgg      5913
Glu Glu Ala Glu Glu Glu Ala Gln Arg Ala Asn Ala Ser Arg Arg
1880                1885                1890 aaa ctg cag cgc gag ctg gag gac gcc act gag acg gcc gat gcc      5958
Lys Leu Gln Arg Glu Leu Glu Asp Ala Thr Glu Thr Ala Asp Ala
1895                1900                1905 atg aac cgc gaa gtc agc tcc cta aag aac aag ctc agg cgc ggg      6003
Met Asn Arg Glu Val Ser Ser Leu Lys Asn Lys Leu Arg Arg Gly
1910                1915                1920 gac ctg ccg ttt gtc gtg ccc cgc cga atg gcc cgg aaa ggc gcc      6048
Asp Leu Pro Phe Val Val Pro Arg Arg Met Ala Arg Lys Gly Ala
1925                1930                1935 ggg gat ggc tcc gac gaa gag gta gat ggc aaa gcg gat ggg gct      6093
Gly Asp Gly Ser Asp Glu Glu Val Asp Gly Lys Ala Asp Gly Ala
1940                1945                1950 gag gcc aaa cct gcc gaa taa gcctcttctc ctgcagcctg agatggatgg   6144
Glu Ala Lys Pro Ala Glu
1955                1960 acagacagac accacagcct cccttccca gaccccgcag cacgcctctc cccaccttct   6204
```

```
tgggactgct gtgaacatgc ctcctcctgc cctccgcccc gtcccccat cccgtttccc    6264
tccaggtgtt gttgagggca tttggcttcc tctgctgcat ccccttccag ctccctcccc    6324
tgctcagaat ctgataccaa agagacaggg cccgggccca ggcagagagc gaccagcagg    6384
ctcctcagcc ctctcttgcc aaaaagcaca agatgttgag gcgagcaggg caggcccccg    6444
gggaggggcc agagttttct atgaatctat ttttcttcag actgaggcct tttggtagtc    6504
ggagccccg cagtcgtcag cctccctgac gtctgccacc agcgccccca ctcctcctcc    6564
tttctttgct gtttgcaatc acacgtggtg acctcacaca cctctgcccc ttgggcctcc    6624
cactcccatg gctctgggcg gtccagaagg agcaggccct gggcctccac ctctgtgcag    6684
ggcacagaag gctggggtgg ggggaggagt ggattcctcc ccaccctgtc ccaggcagcg    6744
ccactgtccg ctgtctccct cctgattcta aaatgtctca agtgcaatgc cccctccct    6804
cctttaccga ggacagcctg cctctgccac agcaaggctg tcggggtcaa gctggaaagg    6864
ccagcagcct tccagtggct ctcccaaca ctcttgggga ccaaatatat ttaatggtta    6924
agggacttgt cccaagtctg acagccagag cgttagaggg gccagcggcc ctcccaggcg    6984
atcttgtgtc tactctagga ctgggcccga gggtggttta cctgcaccgt tgactcagta    7044
tagtttaaaa atctgccacc tgcacaggta tttttgaaag caaataagg ttttctttt    7104
tccccttct tgtaataaat gataaaattc cgagtctttc tcactgcctt tgtttagaag    7164
agagtagctc gtcctcactg gtctacactg gttgccgaat ttacttgtat tcctaactgt    7224
tttgtatatg ctgcattgag acttacggca agaaggcatt tttttttttt aaaggaaaca    7284
aactctcaaa tcatgaagtg atataaaagc tgcatatgcc tacaaagctc tgaattcagg    7344
tcccagttgc tgtcacaaag gagtgagtga aactcccacc ctacccctt ttttatataa    7404
taaaagtgcc ttagcatgtg ttgcagctgt caccactaca gtaagctggt ttacagatgt    7464
tttccactga gcatcacaat aaagagaacc atgtgctacg a                        7505
```

<210> SEQ ID NO 4
<211> LENGTH: 1960
<212> TYPE: PRT
<213> ORGANISM: Homo sapiens

<400> SEQUENCE: 4

```
Met Ala Gln Gln Ala Ala Asp Lys Tyr Leu Tyr Val Asp Lys Asn Phe
  1               5                  10                  15

Ile Asn Asn Pro Leu Ala Gln Ala Asp Trp Ala Ala Lys Lys Leu Val
             20                  25                  30

Trp Val Pro Ser Asp Lys Ser Gly Phe Glu Pro Ala Ser Leu Lys Glu
         35                  40                  45

Glu Val Gly Glu Glu Ala Ile Val Glu Leu Val Glu Asn Gly Lys Lys
     50                  55                  60

Val Lys Val Asn Lys Asp Asp Ile Gln Lys Met Asn Pro Pro Lys Phe
 65                  70                  75                  80

Ser Lys Val Glu Asp Met Ala Glu Leu Thr Cys Leu Asn Glu Ala Ser
                 85                  90                  95

Val Leu His Asn Leu Lys Glu Arg Tyr Tyr Ser Gly Leu Ile Tyr Thr
            100                 105                 110

Tyr Ser Gly Leu Phe Cys Val Val Ile Asn Pro Tyr Lys Asn Leu Pro
        115                 120                 125

Ile Tyr Ser Glu Glu Ile Val Glu Met Tyr Lys Gly Lys Lys Arg His
    130                 135                 140
```

```
Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
            165                 170                 175

Gly Ala Gly Lys Thr Glu Asn Thr Lys Lys Val Ile Gln Tyr Leu Ala
            180                 185                 190

Tyr Val Ala Ser Ser His Lys Ser Lys Lys Asp Gln Gly Glu Leu Glu
            195                 200                 205

Arg Gln Leu Leu Gln Ala Asn Pro Ile Leu Glu Ala Phe Gly Asn Ala
            210                 215                 220

Lys Thr Val Lys Asn Asp Asn Ser Ser Arg Phe Gly Lys Phe Ile Arg
225                 230                 235                 240

Ile Asn Phe Asp Val Asn Gly Tyr Ile Val Gly Ala Asn Ile Glu Thr
                245                 250                 255

Tyr Leu Leu Glu Lys Ser Arg Ala Ile Arg Gln Ala Lys Glu Glu Arg
                260                 265                 270

Thr Phe His Ile Phe Tyr Tyr Leu Leu Ser Gly Ala Gly Glu His Leu
            275                 280                 285

Lys Thr Asp Leu Leu Leu Glu Pro Tyr Asn Lys Tyr Arg Phe Leu Ser
290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Glu Glu Gln
                325                 330                 335

Met Gly Leu Leu Arg Val Ile Ser Gly Val Leu Gln Leu Gly Asn Ile
            340                 345                 350

Val Phe Lys Lys Glu Arg Asn Thr Asp Gln Ala Ser Met Pro Asp Asn
            355                 360                 365

Thr Ala Ala Gln Lys Val Ser His Leu Leu Gly Ile Asn Val Thr Asp
            370                 375                 380

Phe Thr Arg Gly Ile Leu Thr Pro Arg Ile Lys Val Gly Arg Asp Tyr
385                 390                 395                 400

Val Gln Lys Ala Gln Thr Lys Glu Gln Ala Asp Phe Ala Ile Glu Ala
                405                 410                 415

Leu Ala Lys Ala Thr Tyr Glu Arg Met Phe Arg Trp Leu Val Leu Arg
            420                 425                 430

Ile Asn Lys Ala Leu Asp Lys Thr Lys Arg Gln Gly Ala Ser Phe Ile
            435                 440                 445

Gly Ile Leu Asp Ile Ala Gly Phe Glu Ile Phe Asp Leu Asn Ser Phe
450                 455                 460

Glu Gln Leu Cys Ile Asn Tyr Thr Asn Glu Lys Leu Gln Gln Leu Phe
465                 470                 475                 480

Asn His Thr Met Phe Ile Leu Glu Gln Glu Glu Tyr Gln Arg Glu Gly
                485                 490                 495

Ile Glu Trp Asn Phe Ile Asp Phe Gly Leu Asp Leu Gln Pro Cys Ile
            500                 505                 510

Asp Leu Ile Glu Lys Pro Ala Gly Pro Pro Gly Ile Leu Ala Leu Leu
            515                 520                 525

Asp Glu Glu Cys Trp Phe Pro Lys Ala Thr Asp Lys Ser Phe Val Glu
            530                 535                 540

Lys Val Met Gln Glu Gln Gly Thr His Pro Lys Phe Gln Lys Pro Lys
545                 550                 555                 560

Gln Leu Lys Asp Lys Ala Asp Phe Cys Ile Ile His Tyr Ala Gly Lys
```

```
                565                 570                 575
Val Asp Tyr Lys Ala Asp Glu Trp Leu Met Lys Asn Met Asp Pro Leu
            580                 585                 590

Asn Asp Asn Ile Ala Thr Leu Leu His Gln Ser Ser Asp Lys Phe Val
            595                 600                 605

Ser Glu Leu Trp Lys Asp Val Asp Arg Ile Ile Gly Leu Asp Gln Val
            610                 615                 620

Ala Gly Met Ser Glu Thr Ala Leu Pro Gly Ala Phe Lys Thr Arg Lys
625                 630                 635                 640

Gly Met Phe Arg Thr Val Gly Gln Leu Tyr Lys Glu Gln Leu Ala Lys
                645                 650                 655

Leu Met Ala Thr Leu Arg Asn Thr Asn Pro Asn Phe Val Arg Cys Ile
                660                 665                 670

Ile Pro Asn His Glu Lys Lys Ala Gly Lys Leu Asp Pro His Leu Val
                675                 680                 685

Leu Asp Gln Leu Arg Cys Asn Gly Val Leu Glu Gly Ile Arg Ile Cys
            690                 695                 700

Arg Gln Gly Phe Pro Asn Arg Val Val Phe Gln Glu Phe Arg Gln Arg
705                 710                 715                 720

Tyr Glu Ile Leu Thr Pro Asn Ser Ile Pro Lys Gly Phe Met Asp Gly
                725                 730                 735

Lys Gln Ala Cys Val Leu Met Ile Lys Ala Leu Glu Leu Asp Ser Asn
            740                 745                 750

Leu Tyr Arg Ile Gly Gln Ser Lys Val Phe Phe Arg Ala Gly Val Leu
        755                 760                 765

Ala His Leu Glu Glu Glu Arg Asp Leu Lys Ile Thr Asp Val Ile Ile
    770                 775                 780

Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
                805                 810                 815

Ala Ala Tyr Leu Lys Leu Arg Asn Trp Gln Trp Trp Arg Leu Phe Thr
            820                 825                 830

Lys Val Lys Pro Leu Leu Gln Val Ser Arg Gln Glu Glu Met Met
            835                 840                 845

Ala Lys Glu Glu Glu Leu Val Lys Val Arg Glu Lys Gln Leu Ala Ala
850                 855                 860

Glu Asn Arg Leu Thr Glu Met Glu Thr Leu Gln Ser Gln Leu Met Ala
865                 870                 875                 880

Glu Lys Leu Gln Leu Gln Glu Gln Leu Gln Ala Glu Thr Glu Leu Cys
            885                 890                 895

Ala Glu Ala Glu Glu Leu Arg Ala Arg Leu Thr Ala Lys Lys Gln Glu
                900                 905                 910

Leu Glu Glu Ile Cys His Asp Leu Glu Ala Arg Val Glu Glu Glu Glu
                915                 920                 925

Glu Arg Cys Gln His Leu Gln Ala Glu Lys Lys Met Gln Gln Asn
            930                 935                 940

Ile Gln Glu Leu Glu Glu Gln Leu Glu Glu Glu Ser Ala Arg Gln
945                 950                 955                 960

Lys Leu Gln Leu Glu Lys Val Thr Thr Glu Ala Lys Leu Lys Lys Leu
            965                 970                 975

Glu Glu Glu Gln Ile Ile Leu Glu Asp Gln Asn Cys Lys Leu Ala Lys
        980                 985                 990
```

```
Glu Lys Lys Leu Leu Glu Asp Arg Ile Ala Glu Phe Thr Thr Asn Leu
        995                 1000                    1005

Thr Glu Glu Glu Lys Ser Lys Ser Leu Ala Lys Leu Lys Asn
    1010                1015                1020

Lys His Glu Ala Met Ile Thr Asp Leu Glu Glu Arg Leu Arg Arg
    1025                1030                1035

Glu Glu Lys Gln Arg Gln Glu Leu Glu Lys Thr Arg Arg Lys Leu
    1040                1045                1050

Glu Gly Asp Ser Thr Asp Leu Ser Asp Gln Ile Ala Glu Leu Gln
    1055                1060                1065

Ala Gln Ile Ala Glu Leu Lys Met Gln Leu Ala Lys Lys Glu Glu
    1070                1075                1080

Glu Leu Gln Ala Ala Leu Ala Arg Val Glu Glu Glu Ala Ala Gln
    1085                1090                1095

Lys Asn Met Ala Leu Lys Lys Ile Arg Glu Leu Glu Ser Gln Ile
    1100                1105                1110

Ser Glu Leu Gln Glu Asp Leu Glu Ser Glu Arg Ala Ser Arg Asn
    1115                1120                1125

Lys Ala Glu Lys Gln Lys Arg Asp Leu Gly Glu Glu Leu Glu Ala
    1130                1135                1140

Leu Lys Thr Glu Leu Glu Asp Thr Leu Asp Ser Thr Ala Ala Gln
    1145                1150                1155

Gln Glu Leu Arg Ser Lys Arg Glu Gln Glu Val Asn Ile Leu Lys
    1160                1165                1170

Lys Thr Leu Glu Glu Glu Ala Lys Thr His Glu Ala Gln Ile Gln
    1175                1180                1185

Glu Met Arg Gln Lys His Ser Gln Ala Val Glu Glu Leu Ala Glu
    1190                1195                1200

Gln Leu Glu Gln Thr Lys Arg Val Lys Ala Asn Leu Glu Lys Ala
    1205                1210                1215

Lys Gln Thr Leu Glu Asn Glu Arg Gly Glu Leu Ala Asn Glu Val
    1220                1225                1230

Lys Val Leu Leu Gln Gly Lys Gly Asp Ser Glu His Lys Arg Lys
    1235                1240                1245

Lys Val Glu Ala Gln Leu Gln Glu Leu Gln Val Lys Phe Asn Glu
    1250                1255                1260

Gly Glu Arg Val Arg Thr Glu Leu Ala Asp Lys Val Thr Lys Leu
    1265                1270                1275

Gln Val Glu Leu Asp Asn Val Thr Gly Leu Leu Ser Gln Ser Asp
    1280                1285                1290

Ser Lys Ser Ser Lys Leu Thr Lys Asp Phe Ser Ala Leu Glu Ser
    1295                1300                1305

Gln Leu Gln Asp Thr Gln Glu Leu Leu Gln Glu Glu Asn Arg Gln
    1310                1315                1320

Lys Leu Ser Leu Ser Thr Lys Leu Lys Gln Val Glu Asp Glu Lys
    1325                1330                1335

Asn Ser Phe Arg Glu Gln Leu Glu Glu Glu Glu Glu Ala Lys His
    1340                1345                1350

Asn Leu Glu Lys Gln Ile Ala Thr Leu His Ala Gln Val Ala Asp
    1355                1360                1365

Met Lys Lys Lys Met Glu Asp Ser Val Gly Cys Leu Glu Thr Ala
    1370                1375                1380
```

```
Glu Glu Val Lys Arg Lys Leu Gln Lys Asp Leu Glu Gly Leu Ser
    1385                1390                1395

Gln Arg His Glu Glu Lys Val Ala Ala Tyr Asp Lys Leu Glu Lys
    1400                1405                1410

Thr Lys Thr Arg Leu Gln Gln Glu Leu Asp Asp Leu Leu Val Asp
    1415                1420                1425

Leu Asp His Gln Arg Gln Ser Ala Cys Asn Leu Glu Lys Lys Gln
    1430                1435                1440

Lys Lys Phe Asp Gln Leu Leu Ala Glu Glu Lys Thr Ile Ser Ala
    1445                1450                1455

Lys Tyr Ala Glu Glu Arg Asp Arg Ala Glu Ala Glu Ala Arg Glu
    1460                1465                1470

Lys Glu Thr Lys Ala Leu Ser Leu Ala Arg Ala Leu Glu Glu Ala
    1475                1480                1485

Met Glu Gln Lys Ala Glu Leu Glu Arg Leu Asn Lys Gln Phe Arg
    1490                1495                1500

Thr Glu Met Glu Asp Leu Met Ser Ser Lys Asp Asp Val Gly Lys
    1505                1510                1515

Ser Val His Glu Leu Glu Lys Ser Lys Arg Ala Leu Glu Gln Gln
    1520                1525                1530

Val Glu Glu Met Lys Thr Gln Leu Glu Glu Leu Glu Asp Glu Leu
    1535                1540                1545

Gln Ala Thr Glu Asp Ala Lys Leu Arg Leu Glu Val Asn Leu Gln
    1550                1555                1560

Ala Met Lys Ala Gln Phe Glu Arg Asp Leu Gln Gly Arg Asp Glu
    1565                1570                1575

Gln Ser Glu Glu Lys Lys Lys Gln Leu Val Arg Gln Val Arg Glu
    1580                1585                1590

Met Glu Ala Glu Leu Glu Asp Glu Arg Lys Gln Arg Ser Met Ala
    1595                1600                1605

Val Ala Ala Arg Lys Lys Leu Glu Met Asp Leu Lys Asp Leu Glu
    1610                1615                1620

Ala His Ile Asp Ser Ala Asn Lys Asn Arg Asp Glu Ala Ile Lys
    1625                1630                1635

Gln Leu Arg Lys Leu Gln Ala Gln Met Lys Asp Cys Met Arg Glu
    1640                1645                1650

Leu Asp Asp Thr Arg Ala Ser Arg Glu Glu Ile Leu Ala Gln Ala
    1655                1660                1665

Lys Glu Asn Glu Lys Lys Leu Lys Ser Met Glu Ala Glu Met Ile
    1670                1675                1680

Gln Leu Gln Glu Glu Leu Ala Ala Ala Glu Arg Ala Lys Arg Gln
    1685                1690                1695

Ala Gln Gln Glu Arg Asp Glu Leu Ala Asp Glu Ile Ala Asn Ser
    1700                1705                1710

Ser Gly Lys Gly Ala Leu Ala Leu Glu Glu Lys Arg Arg Leu Glu
    1715                1720                1725

Ala Arg Ile Ala Gln Leu Glu Glu Glu Leu Glu Glu Glu Gln Gly
    1730                1735                1740

Asn Thr Glu Leu Ile Asn Asp Arg Leu Lys Lys Ala Asn Leu Gln
    1745                1750                1755

Ile Asp Gln Ile Asn Thr Asp Leu Asn Leu Glu Arg Ser His Ala
    1760                1765                1770

Gln Lys Asn Glu Asn Ala Arg Gln Gln Leu Glu Arg Gln Asn Lys
```

```
                1775                1780                1785

Glu Leu Lys Val Lys Leu Gln Glu Met Glu Gly Thr Val Lys Ser
    1790                1795                1800

Lys Tyr Lys Ala Ser Ile Thr Ala Leu Glu Ala Lys Ile Ala Gln
    1805                1810                1815

Leu Glu Gln Leu Asp Asn Glu Thr Lys Glu Arg Gln Ala Ala
    1820                1825                1830

Cys Lys Gln Val Arg Arg Thr Glu Lys Lys Leu Lys Asp Val Leu
    1835                1840                1845

Leu Gln Val Asp Asp Glu Arg Arg Asn Ala Glu Gln Tyr Lys Asp
    1850                1855                1860

Gln Ala Asp Lys Ala Ser Thr Arg Leu Lys Gln Leu Lys Arg Gln
    1865                1870                1875

Leu Glu Glu Ala Glu Glu Ala Gln Arg Ala Asn Ala Ser Arg
    1880                1885                1890

Arg Lys Leu Gln Arg Glu Leu Glu Asp Ala Thr Glu Thr Ala Asp
    1895                1900                1905

Ala Met Asn Arg Glu Val Ser Ser Leu Lys Asn Lys Leu Arg Arg
    1910                1915                1920

Gly Asp Leu Pro Phe Val Val Pro Arg Arg Met Ala Arg Lys Gly
    1925                1930                1935

Ala Gly Asp Gly Ser Asp Glu Glu Val Asp Gly Lys Ala Asp Gly
    1940                1945                1950

Ala Glu Ala Lys Pro Ala Glu
    1955                1960

<210> SEQ ID NO 5
<211> LENGTH: 12
<212> TYPE: PRT
<213> ORGANISM: Homo sapiens

<400> SEQUENCE: 5

Glu Gln Ala Asp Phe Ala Ile Glu Ala Leu Ala Lys
1               5                   10

<210> SEQ ID NO 6
<211> LENGTH: 11
<212> TYPE: PRT
<213> ORGANISM: Homo sapiens

<400> SEQUENCE: 6

Leu Arg Leu Glu Val Asn Leu Gln Ala Met Lys
1               5                   10

<210> SEQ ID NO 7
<211> LENGTH: 11
<212> TYPE: PRT
<213> ORGANISM: Homo sapiens

<400> SEQUENCE: 7

Leu Asp Pro His Leu Val Leu Asp Gln Leu Arg
1               5                   10

<210> SEQ ID NO 8
<211> LENGTH: 13
<212> TYPE: PRT
<213> ORGANISM: Homo sapiens

<400> SEQUENCE: 8
```

```
Val Ile Gln Tyr Leu Ala Tyr Val Ala Ser Ser His Lys
1               5                   10

<210> SEQ ID NO 9
<211> LENGTH: 14
<212> TYPE: PRT
<213> ORGANISM: Homo sapiens

<400> SEQUENCE: 9

Val Ile Ser Gly Val Leu Gln Leu Gly Asn Ile Val Phe Lys
1               5                   10

<210> SEQ ID NO 10
<211> LENGTH: 15
<212> TYPE: PRT
<213> ORGANISM: Homo sapiens

<400> SEQUENCE: 10

Val Ile Ser Gly Val Leu Gln Leu Gly Asn Ile Val Phe Lys Lys
1               5                   10                  15

<210> SEQ ID NO 11
<211> LENGTH: 14
<212> TYPE: PRT
<213> ORGANISM: Homo sapiens

<400> SEQUENCE: 11

Ile Met Gly Ile Pro Glu Glu Glu Gln Met Gly Leu Leu Arg
1               5                   10

<210> SEQ ID NO 12
<211> LENGTH: 14
<212> TYPE: PRT
<213> ORGANISM: Homo sapiens

<400> SEQUENCE: 12

Ile Ala Glu Phe Thr Thr Asn Leu Thr Glu Glu Glu Glu Lys
1               5                   10

<210> SEQ ID NO 13
<211> LENGTH: 15
<212> TYPE: PRT
<213> ORGANISM: Homo sapiens

<400> SEQUENCE: 13

Asn Phe Ile Asn Asn Pro Leu Ala Gln Ala Asp Trp Ala Ala Lys
1               5                   10                  15

<210> SEQ ID NO 14
<211> LENGTH: 16
<212> TYPE: PRT
<213> ORGANISM: Homo sapiens

<400> SEQUENCE: 14

Gln Leu Leu Gln Ala Asn Pro Leu Ile Glu Ala Phe Gly Asn Ala Lys
1               5                   10                  15

<210> SEQ ID NO 15
<211> LENGTH: 15
<212> TYPE: PRT
<213> ORGANISM: Homo sapiens

<400> SEQUENCE: 15

Leu Thr Glu Met Glu Thr Leu Gln Ser Gln Leu Met Ala Glu Lys
1               5                   10                  15
```

<210> SEQ ID NO 16
<211> LENGTH: 16
<212> TYPE: PRT
<213> ORGANISM: Homo sapiens

<400> SEQUENCE: 16

Ile Ala Glu Phe Thr Thr Asn Leu Thr Glu Glu Glu Glu Lys Ser Lys
1               5                   10                  15

<210> SEQ ID NO 17
<211> LENGTH: 16
<212> TYPE: PRT
<213> ORGANISM: Homo sapiens

<400> SEQUENCE: 17

Ala Asn Leu Gln Ile Asp Gln Ile Asn Thr Asp Leu Asn Leu Glu Arg
1               5                   10                  15

<210> SEQ ID NO 18
<211> LENGTH: 18
<212> TYPE: PRT
<213> ORGANISM: Homo sapiens

<400> SEQUENCE: 18

Leu Gln Val Glu Leu Asp Asn Val Thr Gly Leu Leu Ser Gln Ser Asp
1               5                   10                  15

Ser Lys

<210> SEQ ID NO 19
<211> LENGTH: 16
<212> TYPE: PRT
<213> ORGANISM: Homo sapiens

<400> SEQUENCE: 19

Leu Gln Gln Glu Leu Asp Asp Leu Leu Val Asp Leu Asp His Gln Arg
1               5                   10                  15

<210> SEQ ID NO 20
<211> LENGTH: 18
<212> TYPE: PRT
<213> ORGANISM: Homo sapiens

<400> SEQUENCE: 20

Thr Gln Leu Glu Glu Leu Glu Asp Glu Leu Leu Gln Ala Thr Glu Asp
1               5                   10                  15

Ala Lys

<210> SEQ ID NO 21
<211> LENGTH: 17
<212> TYPE: PRT
<213> ORGANISM: Homo sapiens

<400> SEQUENCE: 21

Lys Ala Asn Leu Gln Ile Asp Gln Ile Asn Thr Asp Leu Asn Leu Glu
1               5                   10                  15

Arg

<210> SEQ ID NO 22
<211> LENGTH: 20
<212> TYPE: PRT
<213> ORGANISM: Homo sapiens

```
<400> SEQUENCE: 22

Ile Ile Gly Leu Asp Gln Val Ala Gly Met Ser Glu Thr Ala Leu Pro
1               5                   10                  15

Gly Ala Phe Lys
            20

<210> SEQ ID NO 23
<211> LENGTH: 17
<212> TYPE: PRT
<213> ORGANISM: Homo sapiens

<400> SEQUENCE: 23

Thr Leu Glu Glu Glu Ala Lys Thr His Glu Ala Gln Ile Gln Glu Met
1               5                   10                  15

Arg

<210> SEQ ID NO 24
<211> LENGTH: 18
<212> TYPE: PRT
<213> ORGANISM: Homo sapiens

<400> SEQUENCE: 24

Ser Met Glu Ala Glu Met Ile Gln Leu Gln Glu Glu Leu Ala Ala Ala
1               5                   10                  15

Glu Arg

<210> SEQ ID NO 25
<211> LENGTH: 19
<212> TYPE: PRT
<213> ORGANISM: Homo sapiens

<400> SEQUENCE: 25

Ile Arg Glu Leu Glu Ser Gln Ile Ser Glu Leu Gln Glu Asp Leu Glu
1               5                   10                  15

Ser Glu Arg

<210> SEQ ID NO 26
<211> LENGTH: 19
<212> TYPE: PRT
<213> ORGANISM: Homo sapiens

<400> SEQUENCE: 26

Met Gln Gln Asn Ile Gln Glu Leu Glu Glu Gln Leu Glu Glu Glu Glu
1               5                   10                  15

Ser Ala Arg

<210> SEQ ID NO 27
<211> LENGTH: 21
<212> TYPE: PRT
<213> ORGANISM: Homo sapiens

<400> SEQUENCE: 27

Ile Asn Phe Asp Val Asn Gly Tyr Ile Val Gly Ala Asn Ile Glu Thr
1               5                   10                  15

Tyr Leu Leu Glu Lys
            20

<210> SEQ ID NO 28
<211> LENGTH: 19
<212> TYPE: PRT
<213> ORGANISM: Homo sapiens
```

```
<400> SEQUENCE: 28

Leu Gln Gln Leu Phe Asn His Thr Met Phe Ile Leu Glu Gln Glu Glu
1               5                   10                  15

Tyr Gln Arg

<210> SEQ ID NO 29
<211> LENGTH: 21
<212> TYPE: PRT
<213> ORGANISM: Homo sapiens

<400> SEQUENCE: 29

Asp Phe Ser Ala Leu Glu Ser Gln Leu Gln Asp Thr Gln Glu Leu Leu
1               5                   10                  15

Gln Glu Glu Asn Arg
            20

<210> SEQ ID NO 30
<211> LENGTH: 27
<212> TYPE: PRT
<213> ORGANISM: Homo sapiens

<400> SEQUENCE: 30

Ala Leu Glu Gln Gln Val Glu Glu Met Lys Thr Gln Leu Glu Glu Leu
1               5                   10                  15

Glu Asp Glu Leu Gln Ala Thr Glu Asp Ala Lys
            20                  25
```